(12) United States Patent
Tsukamoto et al.

(10) Patent No.: US 6,586,623 B2
(45) Date of Patent: Jul. 1, 2003

(54) THIOL-BASED NAALADASE INHIBITORS

(75) Inventors: Takashi Tsukamoto, Ellicott City, MD (US); Pavel Majer, Sykesville, MD (US); Doris Stoermer, Baltimore, MD (US); Barbara S. Slusher, Kingsville, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 10/046,917

(22) Filed: Jan. 17, 2002

(65) Prior Publication Data
US 2003/0105088 A1 Jun. 5, 2003

Related U.S. Application Data
(60) Provisional application No. 60/261,754, filed on Jan. 17, 2001, and provisional application No. 60/342,772, filed on Dec. 28, 2001.

(51) Int. Cl.⁷ ..................... C07C 321/06; C07C 323/04; C07C 317/14
(52) U.S. Cl. ................. 562/426; 562/429; 562/431; 562/432
(58) Field of Search ................. 562/426, 437, 562/432, 429, 431

(56) References Cited

FOREIGN PATENT DOCUMENTS

| WO | WO 98/53812 | * 12/1998 | .......... A61K/31/34 |
|---|---|---|---|
| WO | WO 00/01668 A2 | 1/2000 | |
| WO | WO 01/91738 A2 | 12/2001 | |
| WO | WO 01/92273 A2 | 12/2001 | |
| WO | WO 01/92274 A2 | 12/2001 | |

OTHER PUBLICATIONS

Suh et al., "Zn(II)–Chelating Inhibitors of Carboxypeptidase A", *Bioorganic & Medicinal Chemistry Letters*, Mar. 16, 1995, pp. 585–588, vol. 5, No. 6, Elsevier Science Ltd., Amsterdam, NL.

* cited by examiner

*Primary Examiner*—Brian Davis
(74) *Attorney, Agent, or Firm*—Foley & Lardner

(57) ABSTRACT

This invention relates to new compounds, pharmaceutical compositions and diagnostic kits comprising such compounds, and methods of using such compounds for inhibiting NAALADase enzyme activity, detecting diseases where NAALADase levels are altered, effecting neuronal activity, effecting TGF-β activity, inhibiting angiogenesis, and treating glutamate abnormalities, diabetic neuropathy, pain, compulsive disorders, prostate diseases, cancers and glaucoma.

25 Claims, 45 Drawing Sheets

TGF-β1 in Dialysate from Rats Treated with Compound C During Ischemia and Reperfusion Dragging Hind Limbs in SOD Transgenic Mice at 210 Days Righting Reflex in SOD Transgenic Mice at 210 Days NAALADase Inhibition Reverses Motor Nerve Conduction Deficit in Well-Established Diabetes Compound D Reverses Sensory Nerve Conduction Velocity Deficit in Established Diabetes

THIOL-BASED NAALADASE INHIBITORS

This application claims the benefit of U.S. Provisional Application No. 60/261,754, filed Jan. 17, 2001, and U.S. Provisional Application No. 60/342,772, filed Dec. 28, 2001, the entire contents of which applications are herein incorporated by reference.

This invention relates to new compounds, pharmaceutical compositions and diagnostic kits comprising such compounds, and methods of using such compounds for inhibiting NAALADase enzyme activity, detecting diseases where NAALADase levels are altered, effecting neuronal activity, effecting TGF-β activity, inhibiting angiogenesis, and treating glutamate abnormalities, diabetic neuropathy, pain, compulsive disorders, prostate diseases, cancers and glaucoma.

The NAALADase enzyme, also known as prostate specific membrane antigen ("PSM" or "PSMA") and human glutamate carboxypeptidase II ("GCP II"), catalyzes the hydrolysis of the neuropeptide N-acetyl-aspartyl-glutamate ("NAAG") to N-acetyl-aspartate ("NAA") and glutamate. Based upon amino acid sequence homology, NAALADase has been assigned to the M28 family of peptidases.

Studies suggest NAALADase inhibitors may be effective in treating ischemia, spinal cord injury, demyelinating diseases, Parkinson's disease, Amyotrophic Lateral Sclerosis ("ALS"), alcohol dependence, nicotine dependence, cocaine dependence, cancer, diabetic neuropathy, pain and schizophrenia, and in inhibiting angiogenesis. In view of their broad range of potential applications, a need exists for new NAALADase inhibitors and pharmaceutical compositions comprising such compounds.

SUMMARY OF THE INVENTION

This invention relates to a compound of formula I

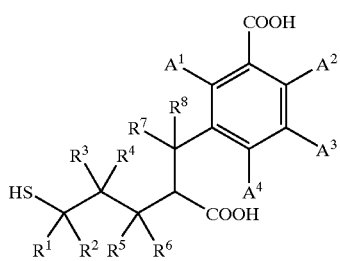

or a pharmaceutically acceptable equivalent of said compound, wherein:
  $R^1$, $R^2$, $R^3$, $R^4$, $R^5$, $R^6$, $R^7$ and $R^8$ are independently hydrogen or $C_1$–$C_3$ alkyl;
  $A^1$, $A^2$, $A^3$ and $A^4$ are independently hydrogen, $C_1$–$C_6$ alkyl, $C_1$–$C_6$ alkoxy, halo, nitro, phenyl, phenoxy, benzyl, benzyloxy or —COOH, or any adjacent two of $A^2$, $A^3$ and $A^4$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

This invention further relates to a compound of formula II

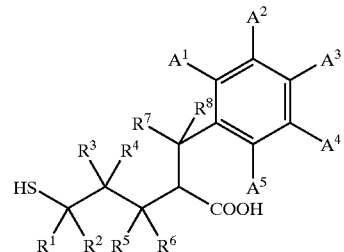

or a pharmaceutically acceptable equivalent of said compound, wherein:
  $R^1$, $R^2$, $R^3$, $R^4$, $R^5$, $R^6$, $R^7$ and $R^8$ are independently hydrogen or $C_1$–$C_3$ alkyl; and
  $A^1$, $A^2$, $A^3$, $A^4$ and $A^5$ are independently hydrogen, $C_1$–$C_6$ alkyl, $C_1$–$C_6$ alkoxy, $C_1$–$C_3$ perhaloalkyl, phenyl, phenoxy, benzyl, benzyloxy, hydroxy, halo, cyano, nitro, —$SO_2R^9$, —(C=O)$NR^9R^{10}$, —(C=O)$NR^9(CH_2)_nCOOH$, —$NR^9$(C=O)$R^{10}$, —$(CH_2)_nCOOH$ or —COOH, or any adjacent two of $A^1$, $A^2$, $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s);
  $R^9$ and $R^{10}$ are independently hydrogen, $C_1$–$C_6$ alkyl, phenyl or benzyl; and
  n is 1–3;
  provided that if $A^1$, $A^3$ and $A^5$ are independently hydrogen, $C_1$–$C_6$ alkyl, $C_1$–$C_6$ alkoxy, halo, nitro, phenyl, phenoxy, benzyl, benzyloxy or —COOH, then neither $A^2$ nor $A^4$ are —COOH; and provided that if any adjacent two of $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s), then $A^2$ is not —COOH.

This invention also relates to a compound of formula III

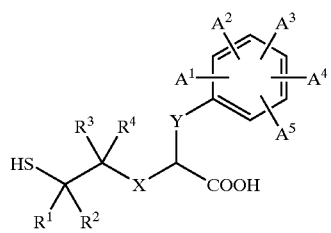

or a pharmaceutically acceptable equivalent of said compound, wherein:
  X and Y are independently —$CR^5R^6$—, —O—, —S— or —NR—, provided that at least one of X and Y is/are —$CR^5R^6$—;
  $A^1$, $A^2$, $A^3$, $A^4$ and $A^5$ are independently hydrogen, $C_1$–$C_9$ alkyl, $C_2$–$C_9$ alkenyl, $C_2$–$C_9$ alkynyl, aryl, heteroaryl, carbocycle, heterocycle, $C_1$–$C_9$ alkoxy, $C_2$–$C_9$ alkenyloxy, phenoxy, benzyloxy, hydroxy, halo, nitro, cyano, isocyano, —$COOR^7$, —$COR^7$, —$NR^7R^8$, —$SR^7$, —$SOR^7$, —$SO_2R^7$, —$SO_2(OR^7)$, —(C=O)$NR^7R^8$, (C=O)$NR^7(CH_2)_nCOOH$, —$NR^7$(C=O)$R^8$ or —$(CH_2)_nCOOH$, or any adjacent two of $A^1$, $A^2$, $A^3$, $A^4$ and $A^5$ form with the benzene ring a fused ring that is saturated or unsaturated, aromatic or non-aromatic, and carbocyclic or heterocyclic, said heterocyclic ring containing 1 or 2 oxygen, nitrogen and/or sulfur heteroatom(s);

n is 1–3;

R, $R^1$, $R^2$, $R^3$, $R^4$, $R^5$, $R^6$, $R^7$ and $R^8$ are independently hydrogen, $C_1$–$C_9$ alkyl, $C_2$–$C_9$ alkenyl, $C_2$–$C_9$ alkynyl, aryl, heteroaryl, carbocycle or heterocycle; and said alkyl, alkenyl, alkynyl, aryl, heteroaryl, carbocycle, heterocycle, alkoxy, alkenyloxy, phenoxy, benzyloxy, and fused ring are independently unsubstituted or substituted with one or more substituent(s);

provided that if $A^1$, $A^2$ and $A^3$ are each hydrogen, and $A^4$ and $A^5$ are each —COOH, then $A^4$ is ortho to $A^5$; and provided that if Y is —$CR^5R^6$—, then at least one of $A^1$, $A^2$, $A^3$, $A^4$ and $A^5$ is/are independently phenoxy, benzyloxy, aryl, heteroaryl, carbocycle or heterocycle that is substituted with one or more substituent(s).

Additionally, this invention relates to method for inhibiting NAALADase enzyme activity, treating a glutamate abnormality, effecting a neuronal activity, treating a prostate disease, treating cancer, inhibiting angiogenesis or effecting a TGF-β activity, comprising administering to a mammal in need of such inhibition, treatment or effect, an effective amount of a compound of formula I, II or III, as described above.

This invention further relates to method for detecting a disease, disorder or condition where NAALADase levels are altered, comprising:

(i) contacting a sample of bodily tissue or fluid with a compound of formula I, II or III, as defined above, wherein said compound binds to any NAALADase in said sample; and (ii) measuring the amount of any NAALADase bound to said sample, wherein the amount of NAALADase is diagnostic for said disease, disorder or condition.

This invention also relates to a method for detecting a disease, disorder or condition where NAALADase levels are altered in an animal or a mammal, comprising:

(i) labeling a compound of formula I, II or III, as defined above, with an imaging reagent;

(ii) administering to said animal or mammal an effective amount of the labeled compound;

(iii) allowing said labeled compound to localize and bind to NAALADase present in said animal or mammal; and (iv) measuring the amount of NAALADase bound to said labeled compound, wherein the amount of NAALADase is diagnostic for said disease, disorder or condition.

Additionally, this invention further relates to a diagnostic kit for detecting a disease, disorder or condition where NAALADase levels are altered, comprising a compound of formula I, II or III, as defined above, labeled with a marker.

Finally, this invention relates to a pharmaceutical composition comprising:

(i) an effective amount of a compound of formula I, II or III, as described above; and (ii) a pharmaceutically acceptable carrier.

DETAILED DESCRIPTION

DEFINITIONS

Figure 1:
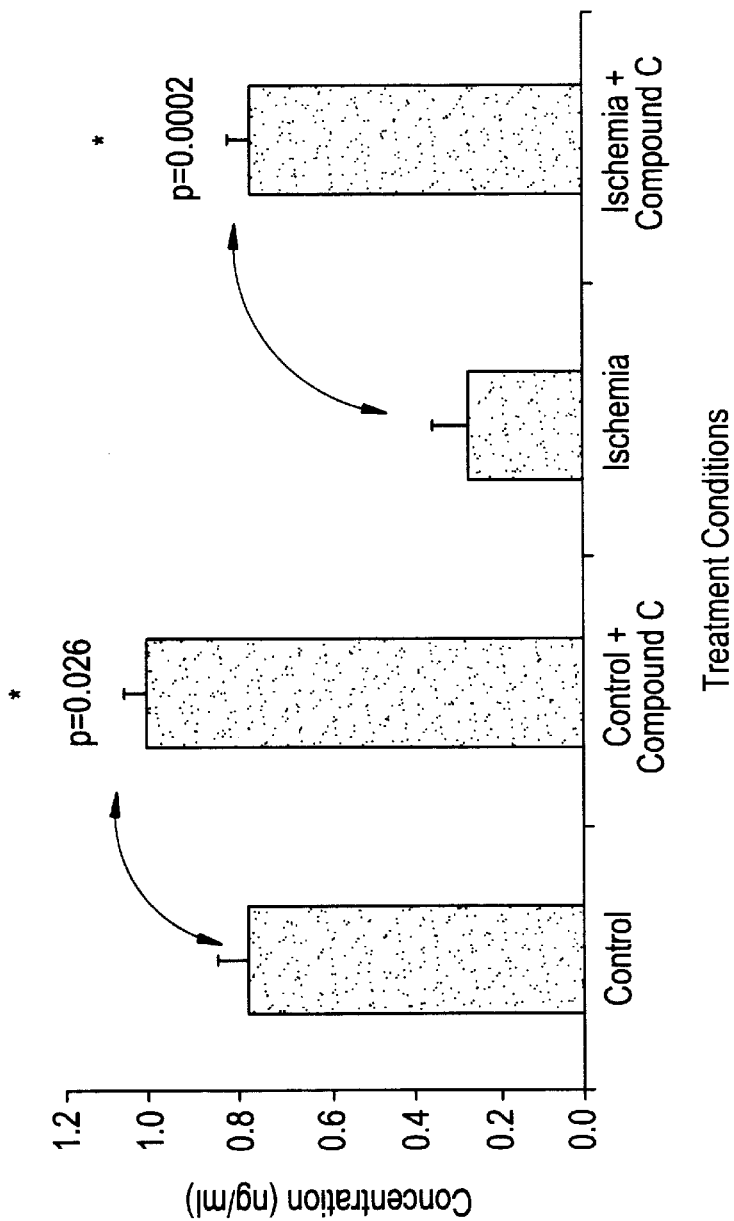
FIG. 1 is a bar graph showing the effect of 2-(phosphonomethyl)pentanedioic acid ("Compound C") on TGF-β1 concentrations in ischemic cell cultures.

"Compound A" refers to 2-[[2,3,4,5,6-pentafluorobenzyl) hydroxyphosphinyl]methyl]pentanedioic acid.

"Compound B" refers to 2-(3-sulfanylpropyl) pentanedioic acid.

"Compound C" refers to 2-(phosphonomethyl) pentanedioic acid (PMPA).

"Compound D" refers to 2-(2-sulfanylethyl)pentanedioic acid.

"Compound E" refers to 3-carboxy-alpha-(3-mercaptopropyl)benzenepropanoic acid.

"Compound F" refers to 3-carboxy-5-(1,1-dimethylethyl)-alpha-(3-mercaptopropyl)benzenepropanoic acid.

"Alkyl" refers to a branched or unbranched saturated hydrocarbon chain comprising a designated number of carbon atoms. For example, $C_1$–$C_9$ alkyl is a straight or branched hydrocarbon chain containing 1 to 9 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, $C_2$–$C_9$ alkenyl is a straight or branched hydrocarbon chain containing 2 to 9 carbon atoms having at least one double bond, and includes but is not limited to substituents such as ethenyl, propenyl, iso-propenyl, butenyl, iso-butenyl, tert-butenyl, n-pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 9 carbon atoms.

"Carbocycle" refers to a hydrocarbon, cyclic moiety having one or more closed ring(s) that is/are alicyclic, aromatic, fused and/or bridged. Examples include cyclopropane, cyclobutane, cyclopentane, cyclohexane, cycloheptane, cyclopentene, cyclohexene, cycloheptene, cycloctene, benzyl, naphthene, anthracene, phenanthracene, biphenyl and pyrene.

"Aryl" refers to an aromatic, hydrocarbon cyclic moiety having one or more closed rings. Examples include, without limitation, phenyl, benzyl, naphthyl, anthracenyl, phenanthracenyl, biphenyl and pyrenyl.

"Heterocycle" refers to a cyclic moiety having one or more closed rings that is/are alicyclic, aromatic, fused and/or bridged, with one or more heteroatoms (for example, sulfur, nitrogen or oxygen) in at least one of the rings. Examples include, without limitation, pyrrolidine, pyrrole, thiazole, thiophene, piperidine, pyridine, isoxazolidine and isoxazole.

"Heteroaryl" refers to an aromatic, cyclic moiety having one or more closed rings with one or more heteroatoms (for example, sulfur, nitrogen or oxygen) in at least one of the rings. Examples include, without limitation, pyrrole, thiophene, pyridine and isoxazole.

"Derivative" refers to a substance produced from another substance either directly or by modification or partial substitution.

"Effective amount" refers to the amount required to produce the desired effect, for example, to inhibit NAALADase enzyme activity and/or angiogenesis, to effect neuronal activity or TGF-β activity, and/or to treat glutamate abnormality, compulsive disorder, prostate disease, cancer or glaucoma.

"Electromagnetic radiation" includes without limitation radiation having the wavelength of $10^{-20}$ to $10^0$ meters. Examples include, without limitation, gamma radiation ($10^{-20}$ to $10^{-13}$ m), X-ray radiation ($10^{-11}$ to $10^{-9}$ m), ultraviolet light (10 nm to 400 nm), visible light (400 nm to 700 nm), infrared radiation (700 nm to 1.0 mm) and microwave radiation (1 mm to 30 cm).

"Halo" refers to at least one fluoro, chloro, bromo or iodo moiety.

"Isosteres" refer to elements, functional groups, substitutents, molecules or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Ideally, isosteric compounds should be isomorphic and able to co-crystallize. Other physical properties that isosteric compounds usually share include boiling point, density, viscosity and thermal conductivity. However, certain properties are usually different: dipolar moments, polarity, polarization, size and shape since the external orbitals may be hybridized differently. The term "isosteres" encompasses "bioisosteres".

"Bioisosteres" are isosteres that, in addition to their physical similarities, share some common biological properties. Typically, bioisosteres interact with the same recognition site or produce broadly similar biological effects.

"Carboxylic acid isosteres" include without limitation direct derivatives such as hydroxamic acids, acyl-cyanamides and acylsulfonamides; planar acidic heterocycles such as tetrazoles, mercaptoazoles, sulfinylazoles, sulfonylazoles, isoxazoles, isothiazoles, hydroxythiadiazoles and hydroxychromes; and nonplanar sulfur- or phosphorus-derived acidic functions such as phosphinates, phosphonates, phosphonamides, sulphonates, sulphonamides, and acylsulphonamides.

"Metabolite" refers to a substance produced by metabolism or by a metabolic process.

"NAAG" refers to N-acetyl-aspartyl-glutamate, an important peptide component of the brain, with levels comparable to the major inhibitor neurotransmitter gamma-aminobutyric acid ("GABA"). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate. In addition, NAAG is an agonist at group II metabotropic glutamate receptors, specifically mGluR3 receptors; when attached to a moiety capable of inhibiting NAALADase, it is expected that metabotropic glutamate receptor ligands will provide potent and specific NAALADase inhibitors.

"NAALADase" refers to N-acetylated α-linked acidic dipeptidase, a membrane bound metallopeptidase which catabolizes NAAG to N-acetylaspartate ("NAA") and glutamate ("GLU"):

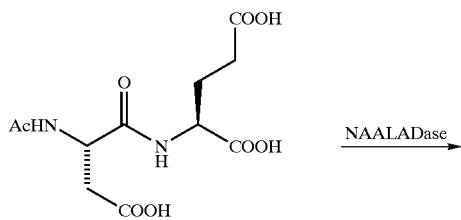

-continued

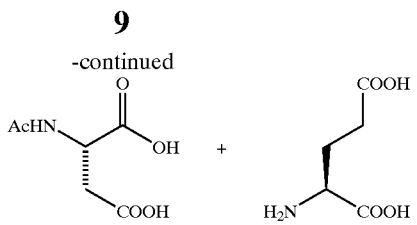

Catabolism of NAAG by NAALADase

NAALADase has been assigned to the M28 peptidase family and is also called PSMA or human GCP II, EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

"Pharmaceutically acceptable equivalent" includes, without limitation, pharmaceutically acceptable salts, hydrates, metabolites, prodrugs and isosteres. Many pharmaceutically acceptable equivalents are expected to have the same or similar in vitro or in vivo activity as the compounds of the invention.

"Pharmaceutically acceptable salt" refers to a salt of the inventive compounds which possesses the desired pharmacological activity and which is neither biologically nor otherwise undesirable. The salt can be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. Basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Prodrug" refers to a derivative of the inventive compounds that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995).

"Radiosensitizer" refers to a low molecular weight compound administered to animals in therapeutically effective amounts to promote the treatment of diseases that are treatable with electromagnetic radiation. Diseases that are treatable with electromagnetic radiation include, without limitation, neoplastic diseases, benign and malignant tumors, and cancerous cells. Electromagnetic radiation treatment of other diseases not listed herein are also contemplated by this invention.

"Inhibition," in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, Ki, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound that is required to cause a 50% inhibition of the target enzyme.

"NAALADase inhibitor" refers to any compound that inhibits NAALADase enzyme activity. Preferably, a NAALADase inhibitor exhibits a $K_i$ of less than 100 $\mu$M, more preferably less than 10 $\mu$M, and even more preferably less than 1 $\mu$M, as determined using any appropriate assay known in the art.

"Isomers" refer to compounds having the same number and kind of atoms, and hence the same molecular weight, but differing in respect to the arrangement or configuration of the atoms.

"Optical isomers" refer to enantiomers or diastereoisomers.

"Stereoisomers" are isomers that differ only in the arrangement of the atoms in space.

"Diastereoisomers" are stereoisomers that are not mirror images of each other. Diastereoisomers occur in compounds having two or more asymmetric carbon atoms; thus, such compounds have $2^n$ optical isomers, where n is the number of asymmetric carbon atoms.

"Enantiomers" are a pair of stereoisomers that are non-superimposable mirror images of each other. Enantiomers result from the presence of one or more asymmetric carbon atoms in the compound (e.g., glyceraldehyde, lactic acid, sugars, tartaric acid, amino acids).

"Enantiomer-enriched" refers to a mixture in which one enantiomer predominates.

"Racemic mixture" means a mixture containing equal amounts of individual enantiomers.

"Non-racemic mixture" is a mixture containing unequal amounts of enantiomers.

"Angiogenesis" refers to the process whereby new capillaries are formed. "Inhibition" of angiogenesis may be measured by many parameters in accordance with this invention and, for instance, may be assessed by delayed appearance of neovascular structures, slowed development of neovascular structures, decreased occurrence of neovascular structures, slowed or decreased severity of angiogenesis-dependent disease effects, arrested angiogenic growth, or regression of previous angiogenic growth. In the extreme, complete inhibition is referred to herein as prevention. In relation to angiogenesis or angiogenic growth, "prevention" refers to no substantial angiogenesis or angiogenic growth if none had previously occurred, or no substantial further angiogenesis or angiogenic growth if growth had previously occurred.

"Angiogenesis-dependent disease" includes, without limitation, rheumatoid arthritis, cardiovascular diseases, neovascular diseases of the eye, peripheral vascular disorders, dermatologic ulcers and cancerous tumor growth, invasion and metastasis.

"Animal" refers to a living organism having sensation and the power of voluntary movement, and which requires for its existence oxygen and organic food. Examples include, without limitation, members of the human, equine, porcine, bovine, murine, canine, or feline species. In the case of a human, an "animal" may also be referred to as a "patient".

"Mammal" refers to a warm-blooded vertebrate animal.

"Anxiety" includes without limitation the unpleasant emotion state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. *Dorland's Illustrated Medical Dictionary*, W.B. Saunders Co., 27th ed. (1988).

"Anxiety Disorder" includes without limitation mental disorders in which anxiety and avoidance behavior predominate. *Dorland's Illustrated Medical Dictionary*, W.B. Saunders Co., 27th ed. (1988). Examples include without limitation panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS. Other anxiety disorders are characterized in *Diagnostic and Statistical Manual of Mental Disorders* (American Psychiatric Association 4th ed. 1994).

"Attention Deficit Disorder" or "ADD" refers to a disorder characterized by developmentally inappropriate inattention and impulsiveness, with or without hyperactivity. Inattention means a failure to finish tasks started, easily distracted, seeming lack of attention, and difficulty concentrating on tasks requiring sustained attention. Impulsiveness means acting before thinking, difficulty taking turns, problems organizing work, and constant shifting from one activity to another. Hyperactivity means difficulty staying seated and sitting still, and running or climbing excessively.

"Cancer" includes, without limitation, ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

"Compulsive disorder" refers to any disorder characterized by irresistible impulsive behavior. Examples of compulsive disorders include without limitation substance dependence, eating disorders, pathological gambling, Attention Deficit Disorder ("ADD"), and Tourette's syndrome.

"Demyelinating disease" refers to any disease involving damage to or removal of the myelin sheath naturally surrounding nerve tissue, such as that defined in U.S. Pat. No. 5,859,046 and International Publication No. WO 98/03178, herein incorporated by reference. Examples include without limitation peripheral demyelinating diseases (such as Guillain-Barré syndrome, peripheral neuropathies and Charcot-Marie Tooth disease) and central demyelinating diseases (such as multiple sclerosis).

"Disease" refers to any deviation from or interruption of the normal structure or function of any part, organ or system (or combinations) of the body that is manifested by a characteristic set of symptoms and signs and whose etiology, pathology, and prognosis may be known or unknown. *Dorland's Illustrated. Medical Dictionary*, (W.B. Saunders Co. 27th ed. 1988).

"Disorder" refers to any derangement or abnormality of function; a morbid physical or mental state. *Dorland's Illustrated Medical Dictionary*,(W.B. Saunders Co. 27th ed. 1988).

"Drug dependence" refers to a psychologic addiction or a physical tolerance to a drug. Tolerance means a need to increase the dose progressively in order to produce the effect originally achieved by smaller amounts.

"Eating disorder" refers to compulsive overeating, obesity or severe obesity. obesity means body weight of 20% over standard height-weight tables. Severe obesity means over 100% overweight.

"Glaucoma" includes without limitation chronic (idiopathic) open-angle glaucomas (e.g., high-pressure, normal-pressure); pupillary block glaucomas (e.g., acute angle-closure, subacute angle-closure, chronic angle-closure, combined-mechanism); developmental glaucomas (e.g., congenital (infantile), juvenile, Anxenfeld-Rieger syndrome, Peters' anomaly, Aniridia); glaucomas associated with other ocular disorders (e.g., glaucomas associated with disorders of the corneal endothelium, iris, ciliary body, lens, retina, choroid and vitreous); glaucomas associated with elevated episcleral venous pressure (e.g., systemic diseases with associated elevated intraocular pressure and glaucoma, corticosteroid-induced glaucoma); glaucomas associated with inflammation and trauma (e.g., glaucomas associated with keratitis, episcleritis, scleritis, uveitis, ocular trauma and hemorrhage); glaucomas following intraocular surgery (e.g., ciliary block (malignant) glaucoma, glaucomas in aphakia and pseudophakia, glaucomas associated with corneal surgery, glaucomas associated with vitreoretinal surgery).

"Glutamate abnormality" refers to any disease, disorder, or condition in which glutamate is implicated, including pathological conditions involving elevated levels of glutamate. Examples of glutamate abnormalities include, without limitation, compulsive disorder, spinal cord injury, epilepsy, stroke, ischemia, demyelinating disease, Alzheimer's disease, Parkinson's disease, ALS, Huntington's disease, schizophrenia, pain, peripheral neuropathy (including but not limited to diabetic neuropathy), traumatic brain injury, neuronal insult, inflammatory disease, anxiety, anxiety disorder, memory impairment and glaucoma.

"Ischemia" refers to localized tissue anemia due to obstruction of the inflow of arterial blood. Global ischemia occurs when blood flow ceases for a period of time, as may result from cardiac arrest. Focal ischemia occurs when a portion of the body, such as the brain, is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin ($B_1$, thiamine and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Mental disorder" refers to any clinically significant behavioral or psychological syndrome characterized by the presence of distressing symptoms or significant impairment of functioning. Mental disorders are assumed to result from some psychological or organic dysfunction of the individual; the concept does not include disturbances that are essentially conflicts between the individual and society (social deviance).

"Metastasis" refers to "[t]he ability of cells of a cancer to disseminate and form new foci of growth at noncontiguous sites (i.e., to form metastases)." See Hill, R. P, "Metastasis", *The Basic Science of Oncology*, Tannock et al., Eds., McGraw-Hill, New York, pp. 178–195 (1992), herein incorporated by reference. "The transition from in situ tumor growth to metastatic disease is defined by the ability of tumor cells of the primary site to invade local tissues and to cross tissue barriers . . . To initiate the metastatic process, carcinoma cells must first penetrate the epithelial basement membrane and then invade the interstitial stroma. . . . For distant metastases, intravasation requires tumor cell invasion of the subendothelial basement membrane that must also be negotiated during tumor cell extravasation . . . The development of malignancy is also associated with tumor-induced angiogenesis [which] not only allows for expansion of the primary tumors, but also permits easy access to the vascular compartment due to defects in the basement membranes of newly formed vessels." See Aznavoorian et al., *Cancer* (1993) 71:1368–1383, herein incorporated by reference.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination processes, epilepsy, cognitive disorder, glutamate abnormality and secondary effects thereof.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuropathy" refers to any disease or malfunction of the nerves. Neuropathy includes, without limitation, peripheral neuropathy, diabetic neuropathy, autonomic peuropathy and mononeuropathy. Peripheral neuropathy may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barré syndrome, diabetes including type I and type II diabetes), chemicals (for example, toxins, lead, dapsone, vitamins, paclitaxel chemotherapy, HAART therapy) and physical injuries to a particular nerve or nerve plexus (for example, trauma, compression, constriction).

"Neuroprotective" refers to the effect of reducing, arresting or ameliorating nervous insult, and protecting, resuscitating or reviving nervous tissue that has suffered nervous insult.

"Pain" refers to localized sensations of discomfort, distress or agony, resulting from the stimulation of specialized nerve endings. It serves as a protective mechanism insofar as it induces the sufferer to remove or withdraw from the source. *Dorland's Illustrated Medical Dictionary*,(W.B. Saunders Co. 27th ed. 1988). Examples of pain include, without limitation, acute, chronic, cancer, burn, incisional, inflammatory, neuropathic and back pain.

"Neuropathic pain" refers to a condition of pain associated with a nerve injury. Depending on the particular syndrome, the pain may be due to alterations of the brain or spinal cord or may be due to abnormalities in the nerve itself. Neuropathic pain may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barré syndrome, diabetes including type I and type II diabetes), chemicals (for example, toxins, lead, dapsone, vitamins, paclitaxel chemotherapy, HAART therapy) and physical injuries to a particular nerve or nerve plexus (for example, trauma, compression, constriction).

"Pathological gambling" refers to a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Prostate disease" refers to any disease affecting the prostate. Examples of prostate disease include without limitation prostate cancer such as adenocarcinoma and metastatic cancers of the prostate; and conditions characterized by abnormal growth of prostatic epithelial cells such as benign prostatic hyperplasia.

"Schizophrenia" refers to a mental disorder or group of mental disorders characterized by disturbances in form and content of thought (loosening of associations, delusions, hallucinations), mood (blunted, flattened, inappropriate affect), sense of self and relationship to the external world (loss of ego boundaries, dereistic thinking, and autistic withdrawal), and behavior (bizarre, apparently purposeless, and stereotyped activity or inactivity). Examples of schizophrenia include, without limitation, acute, ambulatory, borderline, catatonic, childhood, disorganized, hebephrenic, latent, nuclear, paranoid, paraphrenic, prepsychotic, process, pseudoneurotic, pseudopsychopathic, reactive, residual, schizo-affective and undifferentiated schizophrenia. *Dorland's Illustrated Medical Dictionary*, (W.B. Saunders Co. 27th ed. 1988).

"TGF-β" refers to transforming growth factor beta. TGF-β is recognized as a prototype of multifunctional growth factors. It regulates various cell and tissue functions, including cell growth and differentiation, angiogenesis, wound healing, immune function, extracellular matrix production, cell chemotaxis, apoptosis and hematopoiesis.

"TGF-β abnormality" refers to any disease, disorder or condition in which TGF-β is implicated, including diseases disorders and conditions characterized by an abnormal level of TGF-β.

"Abnormal level of TGF-β" refers to a measurable variance from normal levels of TGF-β, as determined by one of ordinary skill in the art using known techniques.

"Therapeutic window of opportunity" or "window" refers, in relation to stroke, to the maximal delay between the onset of stroke and the initiation of efficacious therapy.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

Unless otherwise defined in conjunction with specific diseases or disorders, "treating" refers to:
(i) preventing a disease, disorder or condition from occurring in an animal that may be predisposed to the disease, disorder and/or condition but has not yet been diagnosed as having it;
(ii) inhibiting the disease, disorder or condition, i.e., arresting its development; and/or
(iii) relieving the disease, disorder or condition, i.e., causing regression of the disease, disorder and/or condition.

"Treating ALS" refers to:
(i) preventing ALS from occurring in an animal that may be predisposed to ALS but has not yet been diagnosed as having it;
(ii) inhibiting ALS, i.e. arresting its development;
(iii) relieving ALS, i.e. causing regression of the disease, disorder and/or condition;
(iv) delaying onset of ALS or ALS symptom(s);
(v) slowing progression of ALS or ALS symptom(s);
(vi) prolonging survival of an animal suffering from ALS; and/or
(vii) attenuating ALS symptom(s).

"Treating Huntington's disease" refers to:
(i) preventing Huntington's disease from occurring in an animal that may be predisposed to Huntington's disease but has not yet been diagnosed as having it;
(ii) inhibiting or slowing Huntington's disease, e.g. arresting its development;
(iii) relieving Huntington's disease, e.g. causing its regression;
(iv) improving motor coordination in an animal having Huntington's disease; and/or
(v) prolonging the survival of an animal having Huntington's disease.

"Treating substance dependence" refers to preventing relapse; reducing craving; suppressing tolerance; preventing, inhibiting and/or relieving withdrawal; attenuating sensitization; preventing, inhibiting (i.e. arresting development of) and/or relieving (i.e. causing regression of) substance-induced neurotoxicity; and/or preventing, inhibiting and/or relieving fetal alcohol syndrome.

"Craving" refers to a strong desire for a substance and/or a compelling urge and/or an irresistible impulse to use a substance.

"Dependence" refers to a maladaptive pattern of substance use, leading to clinically significant impairment or distress. Dependence is typically characterized by tolerance and/or withdrawal. Substances for which dependence may be developed include, without limitation, depressants (opioids, synthetic narcotics, barbiturates, glutethimide, methyprylon, ethchlorvynol, methaqualone, alcohol); anxiolytics (diazepam, chlordiazepoxide, alprazolam, oxazepam, temazepam); stimulants (amphetamine, methamphetamine, cocaine); and hallucinogens (LSD, mescaline, peyote, marijuana).

"Relapse" refers to a return to substance use after a period of abstinence, often accompanied by reinstatement.

"Reinstatement" refers to a return to a preexisting level of use and dependence in a person who has resumed substance use following a period of abstinence.

"Sensitization" refers to a condition in which the response to a substance increases with repeated use.

"Tolerance" refers to an acquired reaction to a substance characterized by diminished effect with continued use of the same dose and/or a need for increased doses to achieve intoxication or desired effect previously achieved by lower doses. Both physiological and psychosocial factors may contribute to the development of tolerance. With respect to physiological tolerance, metabolic and/or functional tolerance may develop. By increasing the rate of metabolism of the substance, the body may be able to eliminate the substance more readily. Functional tolerance is defined as a decrease in sensitivity of the central nervous system to the substance.

"Withdrawal" refers to a syndrome characterized by untoward physical changes that occur following cessation of or reduction in substance use, or administration of a pharmacologic antagonist.

One of ordinary skill in the art will recognize that there are alternative nomenclatures, nosologies and classification systems for the diseases, disorders and conditions defined above, and that such systems evolve with medical scientific progress.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

COMPOUNDS OF THE INVENTION

This invention relates to compounds of formula I

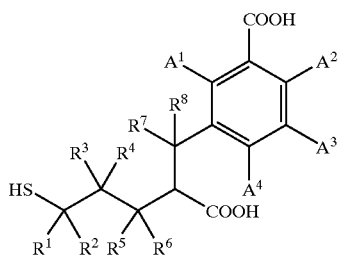

I or a pharmaceutically acceptable equivalent of said compound, wherein:

$R^1$, $R^2$, $R^3$, $R^4$, $R^5$, $R^6$, $R^7$ and $R^8$ are independently hydrogen or $C_1$–$C_3$ alkyl;

$A^1$, $A^2$, $A^3$ and $A^4$ are independently hydrogen, $C_1$–$C_6$ alkyl, $C_1$–$C_6$ alkoxy, halo, nitro, phenyl, phenoxy, benzyl, benzyloxy or —COOH, or any adjacent two of $A^2$, $A^3$ and $A^4$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

In one embodiment, $R^1$, $R^2$, $R^3$, $R^4$, $R^5$, $R^6$, $R^7$ and $R^8$ are independently hydrogen or methyl; and $A^1$, $A^2$, $A^3$ and $A^4$ are independently hydrogen, $C_1$–$C_4$ alkyl, $C_1$–$C_2$ alkoxy, halo, nitro, phenyl, phenoxy, benzyloxy, nitro or —COOH.

In another embodiment, any adjacent two of $A^2$, $A^3$ and $A^4$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

This invention further relates to a compound of formula II

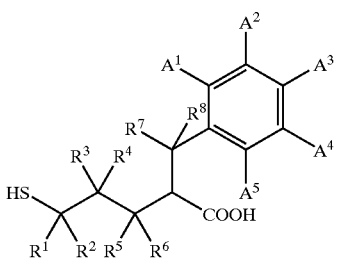

II or a pharmaceutically acceptable equivalent of said compound, wherein:

$R^1$, $R^2$, $R^3$, $R^4$, $R^5$, $R^6$, $R^7$ and $R^8$ are independently hydrogen or $C_1$–$C_3$ alkyl; and $A^1$, $A^2$, $A^3$, $A^4$ and $A^5$ are independently hydrogen, $C_1$–$C_6$ alkyl, $C_1$–$C_6$ alkoxy, $C_1$–$C_3$ perhaloalkyl, phenyl, phenoxy, benzyl, benzyloxy, hydroxy, halo, cyano, nitro, —$SO_2R^9$, —(C=O)$NR^9R^{10}$, —(C=O)$NR^9$($CH_2$)$_n$COOH, —$NR^9$(C=O)$R^{10}$, —($CH_2$)$_n$COOH or —COOH, or any adjacent two of $A^1$, $A^2$, $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s);

$R^9$ and $R^{10}$ are independently hydrogen, $C_1$–$C_6$ alkyl, phenyl or benzyl; and n is 1–3;

provided that if $A^1$, $A^3$ and $A^5$ are independently hydrogen, $C_1$–$C_6$ alkyl, $C_1$–$C_6$ alkoxy, halo, nitro, phenyl, phenoxy, benzyl, benzyloxy or —COOH, then neither $A^2$ nor $A^4$ are —COOH; and provided that if any adjacent two of $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s), then $A^2$ is not —COOH.

In one embodiment, $R^1$, $R^2$, $R^3$, $R^4$, $R^5$, $R^6$, $R^7$ and $R^8$ are each hydrogen; $A^1$, $A^2$, $A^3$, $A^4$ and $A^5$ are independently hydrogen, $C_1$–$C_4$ alkyl, $C_1$–$C_2$ alkoxy, $C_1$–$C_2$ perhaloalkyl, phenyl, phenoxy, hydroxy, halo, cyano, nitro, —$SO_2R^9$, —(C=O)$NR^9R^{10}$, —(C=O)$NR^9$($CH_2$)COOH, —$NR^9$(C=O)$R^{10}$ or —($CH_2$)COOH; and $R^9$ and $R^{10}$ are independently hydrogen, methyl or benzyl.

In another embodiment, any adjacent two of $A^1$, $A^2$, $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

This invention also relates to a compound of formula III

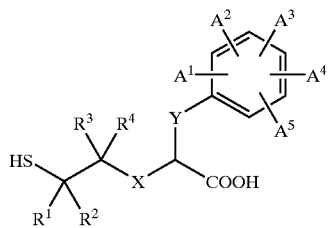

III or a pharmaceutically acceptable equivalent of said compound, wherein:

X and Y are independently —$CR^5R^6$—, —O—, —S— or —NR—, provided that at least one of X and Y is/are —$CR^5R^6$—;

$A^1$, $A^2$, $A^3$, $A^4$ and $A^5$ are independently hydrogen, $C_1$–$C_9$ alkyl, $C_2$–$C_9$ alkenyl, $C_2$–$C_9$ alkynyl, aryl, heteroaryl, carbocycle, heterocycle, $C_1$–$C_9$ alkoxy, $C_2$–$C_9$ alkenyloxy, phenoxy, benzyloxy, hydroxy, halo, nitro, cyano, isocyano, —$COOR^7$, —$COR^7$, —$NR^7R^8$, —$SR^7$, —$SOR^7$, —$SO_2R^7$, —$SO_2(OR^7)$, —(C=O)$NR^7R^8$, —(C=O)$NR^7$($CH_2$)$_n$COOH, —$NR^7$(C=O)$R^8$ or —($CH_2$)$_n$COOH, or any adjacent two of $A^1$, $A^2$, $A^3$, $A^4$ and $A^5$ form with the benzene ring a fused ring that is saturated or unsaturated, aromatic or non-aromatic, and carbocyclic or heterocyclic, said heterocyclic ring containing 1 or 2 oxygen, nitrogen and/or sulfur heteroatom(s);

n is 1–3;

R, $R^1$, $R^2$, $R^3$, $R^4$, $R^5$, $R^6$, $R^7$ and $R^8$ are independently hydrogen, $C_1$–$C_9$ alkyl, $C_2$–$C_9$ alkenyl, $C_2$–$C_9$ alkynyl, aryl, heteroaryl, carbocycle or heterocycle; and said alkyl, alkenyl, alkynyl, aryl, heteroaryl, carbocycle, heterocycle, alkoxy, alkenyloxy, phenoxy, benzyloxy, and fused ring are independently unsubstituted or substituted with one or more substituent(s);

provided that if $A^1$, $A^2$ and $A^3$ are each hydrogen, and $A^4$ and $A^5$ are each —COOH, then $A^4$ is ortho to $A^5$; and provided that if Y is —$CR^5R^6$—, then at least one of $A^1$, $A^2$, $A^3$, $A^4$ and $A^5$ is/are independently phenoxy, benzyloxy, aryl, heteroaryl, carbocycle or heterocycle that is substituted with one or more substituent (s)

In one embodiment, Y is —O—, —S— or —NR—; $A^1$, $A^2$, $A^3$, $A^4$ and $A^5$ are independently hydrogen, $C_1$–$C_4$ alkyl, $C_1$–$C_2$ alkoxy, hydroxy, halo, —COOH, —$COR^7$, —$NR^7$($C$=$O$)$R^8$ or —($CH_2$)COOH; and $R^7$ and $R^8$ are independently hydrogen or methyl.

In another embodiment, Y is —$CR^5R^6$—; $A^1$, $A^2$, $A^3$ and $A^4$ are each hydrogen; and $A^5$ is phenoxy, benzyloxy, aryl, heteroaryl, carbocycle or heterocycle, wherein said phenoxy and benzyloxy are substituted with —COOH, and said aryl, heteroaryl, carbocycle and heterocycle are substituted with one or more substituent(s) selected from the group consisting of cyano and —COOH.

Possible substituents of said alkyl, alkenyl, alkynyl, aryl, heteroaryl, carbocycle, heterocycle, alkoxy, alkenyloxy, phenoxy, benzyloxy, and fused ring include, without limitation, $C_1$–$C_6$ alkyl, $C_2$–$C_6$ alkenyl, $C_2$–$C_6$ alkynyl, $C_1$–$C_6$ alkoxy, $C_2$–$C_6$ alkenyloxy, phenoxy, benzyloxy, hydroxy, carboxy, hydroperoxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitrilo, nitro, nitroso, isonitroso, nitrosamino, imino, nitrosimino, oxo, $C_1$–$C_6$ alkylthio, sulfamino, sulfamoyl, sulfeno, sulfhydryl, sulfinyl, sulfo, sulfonyl, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, disilanyl, siloxy, silyl, silylene and carbocyclic and heterocyclic moieties. Carbocyclic moieties include alicyclic and aromatic structures.

Examples of carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

Representative compounds of the invention are set forth below in TABLE I.

TABLE I

| Compound No. | Structure/Name |
|---|---|
| 1 | 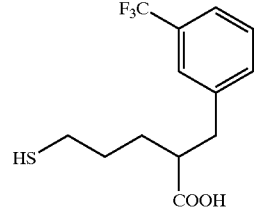<br>alpha-(3-mercaptopropyl)-3-(trifluoromethyl)-benzenepropanoic acid |
| 2 | 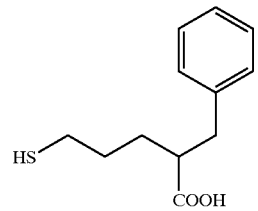<br>alpha-(3-mercaptopropyl)-benzenepropanoic acid |
| 3 | 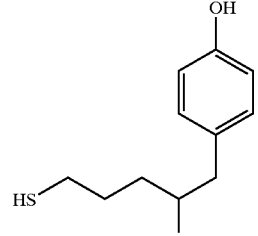<br>4-hydroxy-alpha-(3-mercaptopropyl)-benzenepropanoic acid |
| 4 | 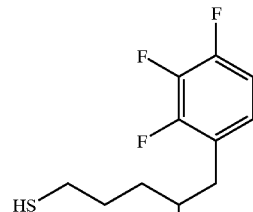<br>2,3,4,5,6-pentafluoro-alpha-(3-mercaptopropyl)-benzenepropanoic acid |
| 5 | 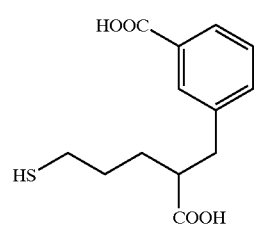<br>3-carboxy-alpha-(3-mercaptopropyl)-benzenepropanoic acid |

TABLE I-continued

| Compound No. | Structure/Name |
|---|---|
| 6 | 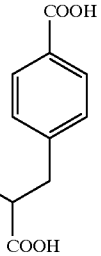<br>4-carboxy-alpha-(3-mercaptopropyl)-benzenepropanoic acid |
| 7 | 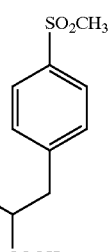<br>alpha-(3-mercaptopropyl)-4-(methylsulfonyl)-benzenepropanoic acid |
| 8 | 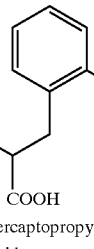<br>2-cyano-alpha-(3-mercaptopropyl)-benzenepropanoic acid |
| 9 | 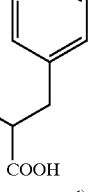<br>5-(2-carboxy-5-mercaptopentyl)-1,3-benzenedicarboxylic acid |
| 10 | 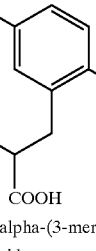<br>5-carboxy-2-chloro-alpha-(3-mercaptopropyl)-benzenepropanoic acid |
| 11 | 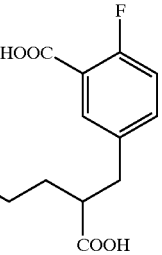<br>3-carboxy-4-fluoro-alpha-(3-mercaptopropyl)-benzenepropanoic acid |
| 12 | 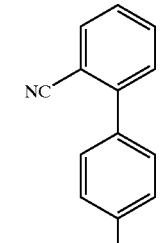<br>4-(2-cyanophenyl)-alpha-(3-mercaptopropyl)-benzenepropanoic acid |
| 13 | 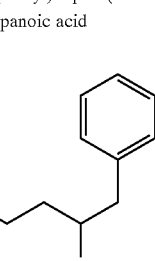<br>2-(aminocarbonyl)-alpha-(3-mercaptopropyl)-benzenepropanoic acid |
| 14 | 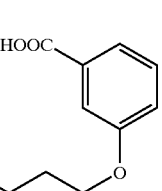<br>3-(1-carboxy-4-mercaptobutoxy)-benzoic acid |
| 15 | 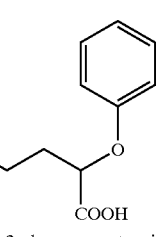<br>5-mercapto-2-phenoxy-pentanoic acid |

TABLE I-continued

| Compound No. | Structure/Name |
|---|---|
| 16 | 2-(3,5-dimethoxyphenoxy)-5-mercapto-pentanoic acid |
| 17 | alpha-(3-mercaptopropyl)-2,5-dimethoxy-benzenepropanoic acid |
| 18 | alpha-(3-mercaptopropyl)-3-phenoxy-benzenepropanoic acid |
| 19 | 2-(3-hydroxyphenoxy)-5-mercapto-pentanoic acid |
| 20 | 3-(1-carboxy-4-mercaptobutoxy)-benzeneacetic acid |
| 21 | 4-(1-carboxy-4-mercaptobutoxy)-benzeneacetic acid |
| 22 | alpha-(3-mercaptopropyl)-4-phenyl-benzenepropanoic acid |
| 23 | 2-(3-acetylphenoxy)-5-mercapto-pentanoic acid |
| 24 | 2-[3-(acetylamino)phenoxy]-5-mercapto-pentanoic acid |

TABLE I-continued

| Compound No. | Structure/Name |
|---|---|
| 25 | 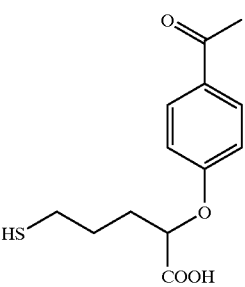<br>2-(4-acetylphenoxy)-5-mercaptopentanoic acid |
| 26 | 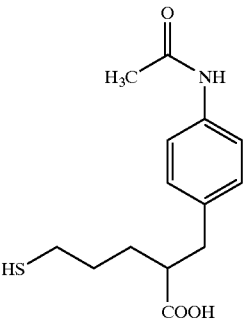<br>4-(acetylamino)-alpha-(3-mercaptopropyl)-benzenepropanoic acid |
| 27 | 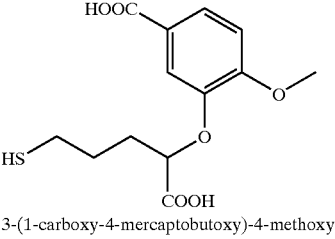<br>3-(1-carboxy-4-mercaptobutoxy)-4-methoxy-benzoic acid |
| 28 | 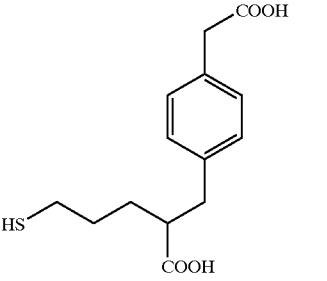<br>4-(carboxymethyl)-alpha-(3-mercaptopropyl)-benzenepropanoic acid |
| 29 | 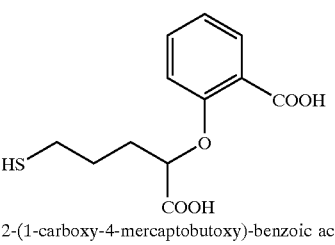<br>2-(1-carboxy-4-mercaptobutoxy)-benzoic acid |
| 30 | 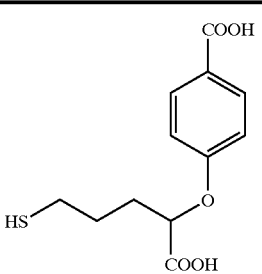<br>4-(1-carboxy-4-mercaptobutoxy)-benzoic acid |
| 31 | 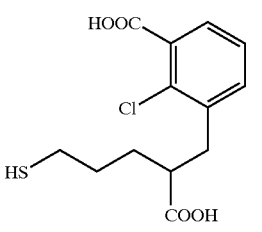<br>3-carboxy-2-chloro-alpha-(3-mercaptopropyl)-benzenepropanoic acid |
| 32 | 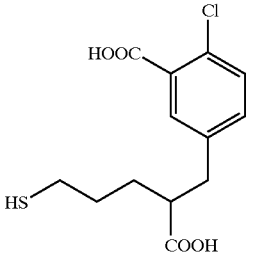<br>3-carboxy-4-chloro-alpha-(3-mercaptopropyl)-benzenepropanoic acid |
| 33 | 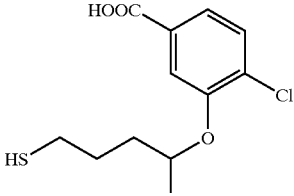<br>3-(1-carboxy-4-mercaptobutoxy)-4-chloro-benzoic acid |
| 34 | 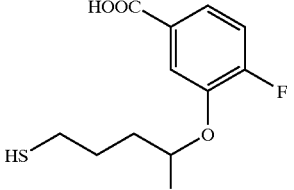<br>3-(1-carboxy-4-mercaptobutoxy)-4-fluoro-benzoic acid |

TABLE I-continued

| Compound No. | Structure/Name |
|---|---|
| 35 | 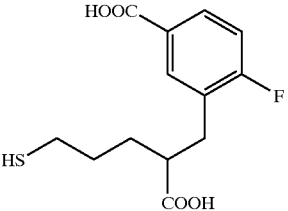<br>5-carboxy-2-fluoro-alpha-(3-mercaptopropyl)-benzenepropanoic acid |
| 36 | 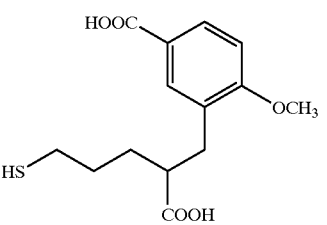<br>5-carboxy-alpha-(3-mercaptopropyl)-2-methoxy-benzenepropanoic acid |
| 37 | 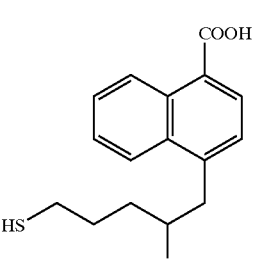<br>4-carboxy-alpha-(3-mercaptopropyl)-1-naphthalenepropanoic acid |
| 38 | 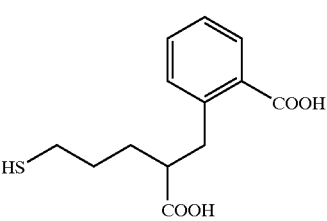<br>2-carboxy-alpha-(3-mercaptopropyl)-benzenepropanoic acid |
| 39 | 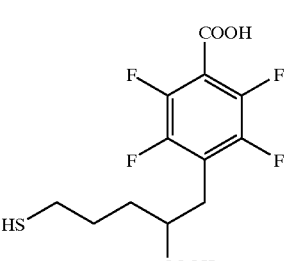<br>4-carboxy-2,3,5,6-tetrafluoro-alpha-(3-mercaptopropyl)-benzenepropanoic acid |
| 40 | 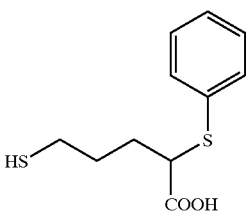<br>5-mercapto-2-(phenylthio)-pentanoic acid |
| 41 | 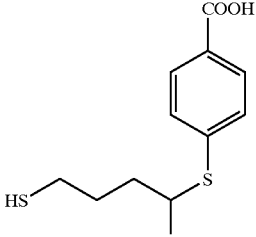<br>3-[1-carboxy-4-mercaptobutyl)thio]-benzoic acid |
| 42 | 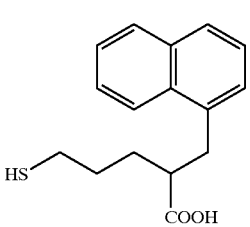<br>alpha-(3-mercaptopropyl)-2-naphthalenepropanoic acid |
| 43 | 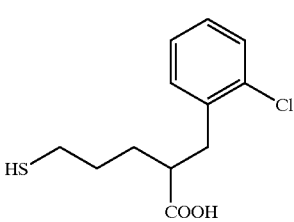<br>2-chloro-alpha-(3-mercaptopropyl)-benzenepropanoic acid |
| 44 | 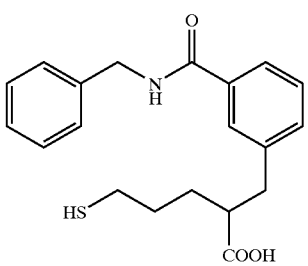<br>alpha-(3-mercaptopropyl)-3-[[(phenylmethyl)amino]carbonyl]-benzenepropanoic acid |

TABLE I-continued

| Compound No. | Structure/Name |
|---|---|
| 45 | 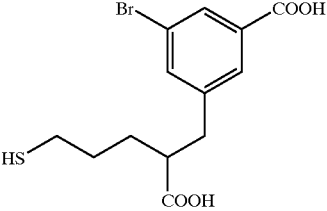<br>3-bromo-5-carboxy-alpha-(3-mercaptopropyl)-benzenepropanoic acid |
| 46 | 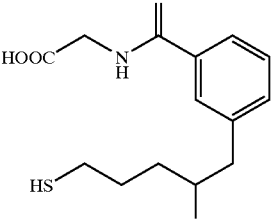<br>3-[[(carboxymethyl)amino]carbonyl]-alpha-(3-mercaptopropyl)-benzenepropanoic acid |
| 47 | 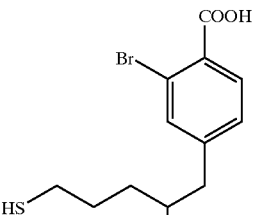<br>3-bromo-4-carboxy-alpha-(3-mercaptopropyl)-benzenepropanoic acid |
| 48 | 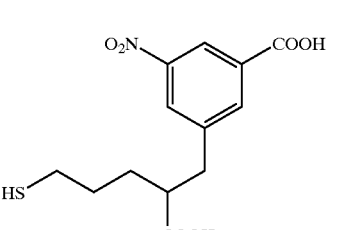<br>3-carboxy-alpha-(3-mercaptopropyl)-5-nitro-benzenepropanoic acid |
| 49 | 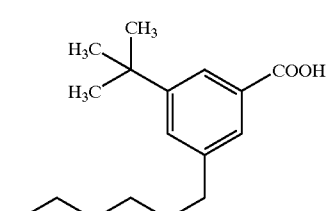<br>3-carboxy-5-(1,1-dimethylethyl)-alpha-(3-mercaptopropyl)-benzenepropanoic acid |
| 50 | 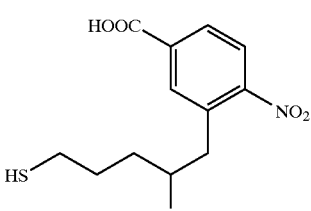<br>5-carboxy-alpha-(3-mercaptopropyl)-2-nitro-benzenepropanoic acid |
| 51 | 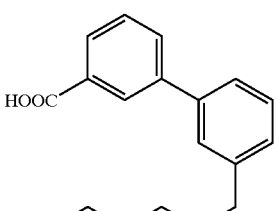<br>3'-(2-carboxy-5-mercaptopentyl)-[1,1'-biphenyl]-3-carboxylic acid |
| 52 | 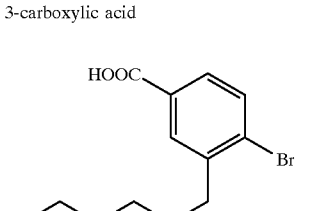<br>2-bromo-5-carboxy-alpha-(3-mercaptopropyl)-benzenepropanoic acid |
| 53 | 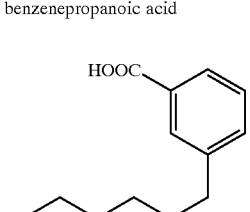<br>(+)-3-carboxy-alpha-(3-mercaptopropyl)-benzenepropanoic acid |
| 54 | 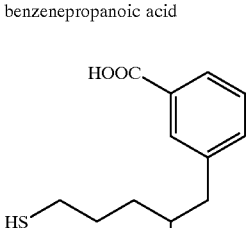<br>(−)-3-carboxy-alpha-(3-mercaptopropyl)-benzenepropanoic acid |

TABLE I-continued

| Compound No. | Structure/Name |
|---|---|
| 55 | 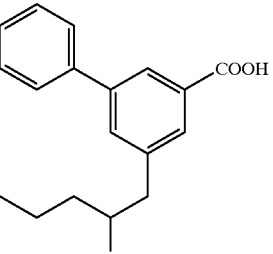<br>5-(2-carboxy-5-mercaptopentyl)-[1,1'-biphenyl]-3-carboxylic acid |
| 56 | 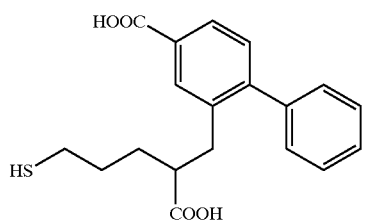<br>2-(2-carboxy-5-mercaptopentyl)-[1,1'-biphenyl]-4-carboxylic acid |
| 57 | 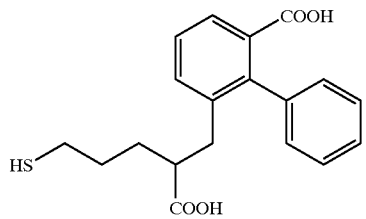<br>6-(2-carboxy-5-mercaptopentyl)-[1,1'-biphenyl]-2-carboxylic acid |
| 58 | 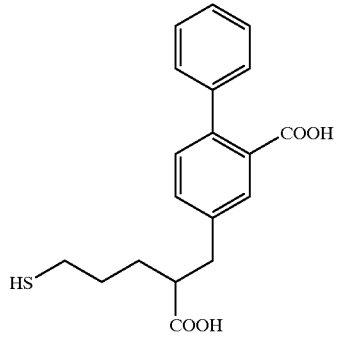<br>4-(2-carboxy-5-mercaptopentyl)-[1,1'-biphenyl]-2-carboxylic acid |
| 59 | 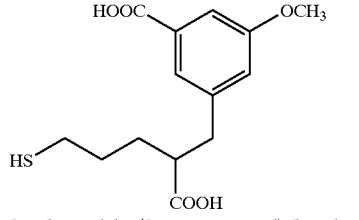<br>3-carboxy-alpha-(3-mercaptopropyl)-5-methoxy-benzenepropanoic acid |
| 60 | 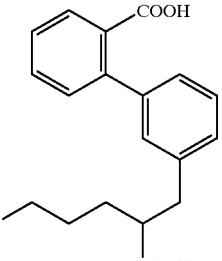<br>3'-(2-carboxy-5-mercaptopentyl)-[1,1'-biphenyl]-2-carboxylic acid |
| 61 | 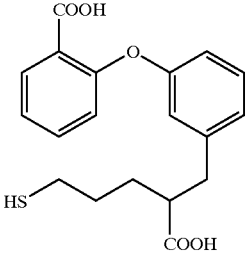<br>3-(2-carboxyphenoxy)-alpha-(3-mercaptopropyl)-benzenepropanoic acid |
| 62 | 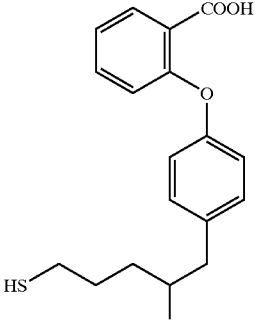<br>4-(2-carboxyphenoxy)-alpha-(3-mercaptopropyl)-benzenepropanoic acid |
| 63 | 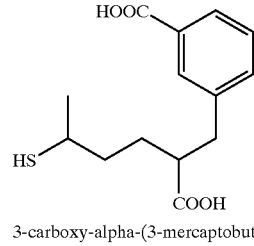<br>3-carboxy-alpha-(3-mercaptobutyl)-benzenepropanoic acid |

TABLE I-continued

| Compound No. | Structure/Name |
|---|---|
| 64 | 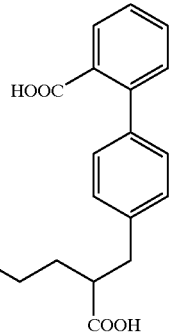<br>4'-(2-carboxy-5-mercaptopropyl)-[1,1'-biphenyl]-2-carboxylic acid |
| 65 | 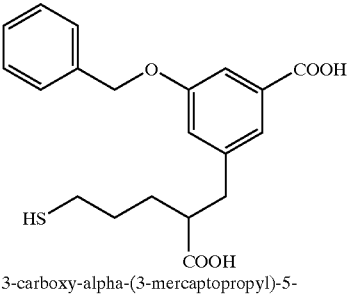<br>3-carboxy-alpha-(3-mercaptopropyl)-5-(phenylmethoxy)-benzenepropanoic acid |
| 66 | 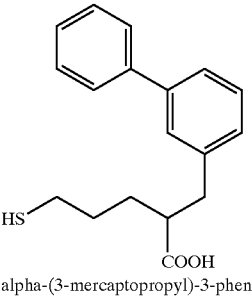<br>alpha-(3-mercaptopropyl)-3-phenyl-benzenepropanoic acid |
| 67 | 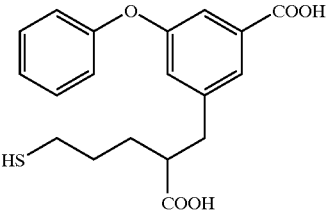<br>3-carboxy-alpha-(3-mercaptopropyl)-5-phenoxy-benzenepropanoic acid |
| 68 | 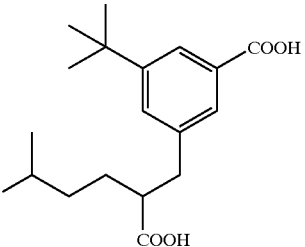<br>3-carboxy-5-(1,1-dimethylethyl)-alpha-(3-mercaptobutyl)-benzenepropanoic acid |
| 69 | 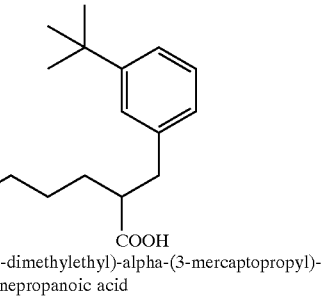<br>3-(1,1-dimethylethyl)-alpha-(3-mercaptopropyl)-benzenepropanoic acid |
| 70 | 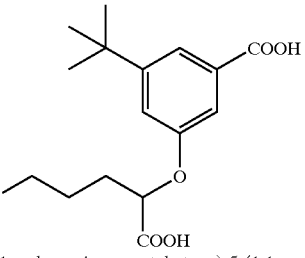<br>3-(1-carboxy-4-mercaptobutoxy)-5-(1,1-dimethylethyl)-benzoic acid |
| 71 | 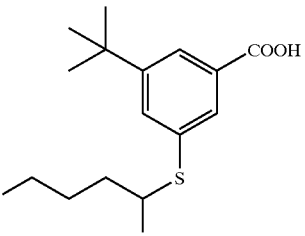<br>3-[(1-carboxy-4-mercaptobutyl)thio-5-(1,1-dimethylethyl)-benzoic acid |
| 72 | 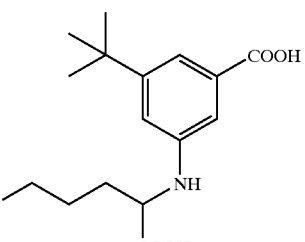<br>3-[(1-carboxy-4-mercaptobutyl)amino]-5-(1,1-dimethylethyl)-benzoic acid |

The inventive compounds possess one or more asymmetric carbon center(s) and are thus capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base and then separation of the mixture of diastereoisomers by crystallization followed by liberation of the optically active bases from these salts. Examples of useful acids include tartaric, diacetyltartaric, dibenzoyltartaric, ditoluoyltartaric and camphorsulfonic acids.

A different process for separating optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means, such as chromatography, distillation, crystallization or sublimation, and then hydrolyzed to deliver the enantiomerically pure compound. In some cases, hydrolysis to the parent optically active drug prior to dosing the patient is unnecessary since the compound can behave as a prodrug. The optically active compounds of the invention can likewise be obtained by utilizing optically active starting materials.

It is understood that the inventive compounds encompass optical isomers as well as racemic and non-racemic mixtures.

METHODS OF THE INVENTION

Methods for Inhibiting NAALADase Enzyme Activity

This invention relates to a method for inhibiting NAALADase enzyme activity in an animal or a mammal, comprising administering to said animal or mammal an effective amount of a compound of the invention, as defined above.

Methods for Treating Glutamate Abnormalities

This invention further relates to a method for treating a glutamate abnormality in an animal or a mammal, comprising administering to said animal or mammal an effective amount of a compound of the invention, as defined above.

Glutamate abnormalities to be treated may be selected from the group consisting of compulsive disorder, stroke, ischemia, demyelinating disease, Parkinson's disease, ALS, Huntington's disease, schizophrenia, pain, anxiety, anxiety disorder, memory impairment and glaucoma. Preferably, the compulsive disorder is alcohol, nicotine or cocaine dependence.

Stroke patients often experience a significant temporal delay between the onset of ischemia and the initiation of therapy. Thus, there is a need for neuroprotectants with a long therapeutic window of opportunity. It is expected that the inventive compounds have a therapeutic window of opportunity of at least 1 hour. Accordingly, when the glutamate abnormality is stroke, the compound of the invention may be administered to said animal or mammal for up to 60 minutes, 120 minutes or more following onset of stroke.

Without being bound to any particular mechanism of action, preferred compounds of the invention are expected to be those that block glutamate release pre-synaptically without interacting with post-synaptic glutamate receptors. Such compounds would be devoid of the behavioral toxicities associated with post-synaptic glutamate antagonists.

Methods for Effecting Neuronal Activities

This invention further relates to a method for effecting a neuronal activity in an animal or a mammal, comprising administering to said animal or mammal an effective amount of a compound of the invention, as defined above.

The neuronal activity that is effected by the inventive method may be stimulation of damaged neurons, promotion of neuronal regeneration, prevention of neurodegeneration or treatment of a neurological disorder.

Examples of neurological disorders that are treatable by the inventive methods include without limitation: trigeminal neuralgia; glossopharyngeal neuralgia; Bell's Palsy; myasthenia gravis; muscular dystrophy; ALS; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; diabetic neuropathy; pain; Alzheimer's disease; and Parkinson's disease.

The inventive method is particularly useful for treating a neurological disorder selected from the group consisting of peripheral neuropathy caused by physical injury or disease state, diabetic neuropathy, pain, traumatic brain injury, physical damage to spinal cord, stroke associated with brain damage, demyelinating disease and neurological disorder relating to neurodegeneration.

When the neurological disorder is pain, the compound of the invention is preferably administered in combination with an effective amount of morphine.

Examples of neurological disorders relating to neurodegeneration include Alzheimer's disease, Parkinson's disease, and ALS.

Methods for Treating Prostate Diseases

This invention further relates to a method for treating a prostate disease in an animal or a mammal, comprising administering to said animal or mammal an effective amount of a compound of the invention, as defined above.

Methods for Treating Cancers

This invention further relates to a method for treating cancer in an animal or a mammal, comprising administering to said animal or mammal an effective amount of a compound of the invention, as defined above.

Preferred cancers to be treated are those in tissues where NAALADase resides, including without limitation the brain, kidney and testis.

Methods for Inhibiting Angiogenesis

This invention further relates to a method for inhibiting angiogenesis in an animal or a mammal, comprising administering to said animal or mammal an effective amount of a compound of the invention, as defined above.

Angiogenesis may be necessary for fertility or metastasis of cancer tumors, or may be related to an angiogenic-dependent disease. Thus, the inventive methods may also be useful for treating an angiogenic-dependent disease including, without limitation, rheumatoid arthritis, cardiovascular diseases, neovascular diseases of the eye, peripheral vascular disorders, dermatologic ulcers and cancerous tumor growth, invasion or metastasis.

Methods for Effecting TGF-β Activity

This invention further relates to a method for effecting a TGF-β activity in an animal or a mammal, comprising administering to said animal or mammal an effective amount of a compound of the invention, as defined above.

Said effecting a TGF-β activity includes increasing, reducing or regulating TGF-β levels, and treating TGF-β abnormalities. Examples of TGF-β abnormalities to be treated include neurodegenerative disorders, extra-cellular matrix formation disorders, cell-growth related diseases, infectious diseases, immune related diseases, epithelial tissue scarring, collagen vascular diseases, fibroproliferative disorders, connective tissue disorders, inflammation, inflammatory diseases, respiratory distress syndrome, infertility and diabetes.

Typical neurodegenerative disorders to be treated include neural tissue damage resulting from ischemia reperfusion injury, myelination and neurodegeneration.

Typical cell-growth related disorders to be treated include those affecting kidney cells, hematopoietic cells, lymphocytes, epithelial cells and endothelial cells.

Typical infectious diseases to be treated include those caused by a macrophage pathogen, particularly a macrophage pathogen selected from the group consisting of bacteria, yeast, fungi, viruses, protozoa, *Trypanosoma cruzi*, *Histoplasma capsulatum*, *Candida albicans*, *Candida parapsilosis*, *Cryptococcus neoformans*, Salmonella, Pneumocystis, Toxoplasma, Listeria, Mycobacteria, Rickettsia and Leishmania. Mycobacteria include without limitation *Mycobacterium tuberculosis* and *Mycobacterium leprae*. Toxoplasma includes without limitation *Toxoplasma gondii*. Rickettsia includes without limitation *R. prowazekii*, *R. coronii* and *R. tsutsugamushi*.

Other examples of infectious diseases to be treated include single or multiple cutaneous lesions, mucosal disease, Chagas' disease, acquired immunodeficiency-syndrome (AIDS), toxoplasmosis, leishmaniasis, trypanosomiasis, shistosomiasis, cryptosporidiosis, *Mycobacterium avium* infections, *Pneumocystis carinii* pneumonia and leprosy.

Typical immune related diseases to be treated include autoimmune disorders; impaired immune function; and immunosuppression associated with an infectious disease, particularly, trypanosomal infection, viral infection, human immunosuppression virus, human T cell lymphotropic virus (HTLV-1), lymphocytic choriomeningitis virus or hepatitis.

Typical collagen vascular diseases to be treated include progressive systemic sclerosis ("PSS"), polymyositis, scleroderma, dermatomyositis, eosinophilic fascitis, morphea, Raynaud's syndrome, interstitial pulmonary fibrosis, scleroderma and systemic. lupus erythematosus.

Typical fibroproliferative disorders to be treated include diabetic nephropathy, kidney disease, proliferative vitreoretinopathy, liver cirrhosis, biliary fibrosis, and myelofibrosis. Especially preferred kidney diseases include mesangial proliferative glomerulonephritis, crescentic glomerulonephritis, diabetic neuropathy, renal interstitial fibrosis, renal fibrosis in transplant patients receiving cyclosporin, and HIV-associated nephropathy.

Typical connective tissue disorders to be treated include scleroderma, myelofibrosis, and hepatic, intraocular and pulmonary fibrosis.

Typical inflammatory diseases to be treated are associated with PSS, polymyositis, scleroderma, dermatomyositis, eosinophilic fascitis, morphea, Raynaud's syndrome, interstitial pulmonary fibrosis, scleroderma, systemic lupus erythematosus, diabetic nephropathy, kidney disease, proliferative vitreoretinopathy, liver cirrhosis, biliary fibrosis, myelofibrosis, mesangial proliferative glomerulonephritis, crescentic glomerulonephritis, diabetic neuropathy, renal interstitial fibrosis, renal fibrosis in transplant patients receiving cyclosporin, or HIV-associated nephropathy.

Without being limited to any particular mechanism of action, preferred compounds of this invention treat inflammatory diseases by regulating TGF-β and/or inhibiting myeloperoxidase.

Other uses associated with the inventive compounds, TGF-β regulating properties include:

stimulating growth of tissue, glands or organs, particularly growth that would enhance milk, production or weight gain;

stimulating cell proliferation, particularly proliferation of fibroblasts, mesenchymal cells or epithelial cells;

inhibiting cell growth, particularly of epithelial cells, endothelial cells, T and B lymphocytes and thymocytes;

inhibiting expression of adipose, skeletal muscle and hematopoietic phenotypes, neoplasms, non-cytocidal viral or other pathogenic infections and autoimmune disorders;

mediating disease resistance and susceptibility;

suppressing cellular immune response;

inhibiting scar tissue formation, preferably in skin or other epithelial tissue that has been damaged by wounds resulting from accidental injury, surgical operations, trauma-induced lacerations or other trauma, or wounds involving the peritoneum for which the excessive connective tissue formation is abdominal adhesions;

increasing the effectiveness of a vaccine, particularly a vaccine for an allergy towards, for example, dust or hayfever; and inhibiting polyp formation.

Diagnostic Methods and Kits

The inventive compounds are useful for in vitro and in vivo diagnostic methods for detecting diseases, disorders and conditions where NAALADase levels are altered including, without limitation, neurological disorders, glutamate abnormalities, diabetic neuropathy, pain, compulsive disorders, prostate diseases, cancers, TGF-β abnormalities and glaucoma.

Accordingly, this invention also relates to a method for detecting a disease, disorder or condition where NAALADase levels are altered, comprising:

(i) contacting a sample of bodily tissue or fluid with a compound of the invention, as defined above, wherein said compound binds to any NAALADase in said sample; and (ii) measuring the amount of any NAALADase bound to said sample, wherein the amount of NAALADase is diagnostic for said disease, disorder or condition.

Examples of bodily tissues and fluids include, without limitation, prostate tissue, ejaculate, seminal vesicle fluid, prostatic fluid, urine, blood, saliva, tears, sweat, lymph and sputum.

The compound may be labeled with a marker using techniques known in the art. Useful markers include, without limitation, enzymatic markers and imaging reagents. Examples of imaging reagents include radiolabels such as $^{131}$I, $^{111}$In, $^{123}$I, $^{99}$Tc, $^{32}$P $^{125}$I, $^{3}$H and $^{14}$C; fluorescent labels such as fluorescein and rhodamine; and chemiluminescers such as luciferin.

The amount of NAALADase can be measured using techniques known in the art including, without limitation, assays (such as immunometric, calorimetric, densitometric, spectrographic and chromatographic assays) and imaging techniques (such as magnetic resonance spectroscopy ("MRS"), magnetic resonance imaging ("MRI"), single-photon emission computed tomography ("SPECT") and positron emission tomography ("PET")).

This invention further relates to a diagnostic kit for detecting a disease, disorder or condition where NAALA-Dase levels are altered, comprising a compound of the invention, as defined above, labeled with a marker. The kit may further comprise buffering agents, agents for reducing background interference, control reagents and/or apparatus for conducting the test.

This invention further relates to a method for detecting a disease, disorder or condition where NAALADase levels are altered in an animal or a mammal, comprising:

(i) labeling a compound of the invention, as defined above, with an imaging reagent;

(ii) administering to said animal or mammal an effective amount of the labeled compound;

(iii) allowing said labeled compound to localize and bind to NAALADase present in said animal or mammal; and (iv) measuring the amount of NAALADase bound to said labeled: compound, wherein the amount of NAALA-Dase is diagnostic for said disease, disorder or condition.

The amount of NAALADase can be measured in vivo using known imaging techniques, as described above.

Incorporation by Reference

The relationship between NAALADase inhibitors and glutamate, and the effectiveness of NAALADase inhibitors in treating and detecting various diseases, disorders and conditions have been discussed in U.S. Pat. Nos. 5,672,592, 5,795,877, 5,804,602, 5,824,662, 5,863,536, 5,977,090, 5,981,209, 6,011,021, 6,017,903, 6,025,344, 6,025,345, 6,046,180, 6,228,888 and 6,265,609; International Publications Nos. WO 00/01668 and WO 00/38785; and other references generally known in the art. The present inventors hereby incorporate by reference, as though set forth herein in full, the entire contents of the aforementioned patents, patent applications and publications, particularly their discussions, figures and data regarding the effectiveness of NAALADase inhibitors in inhibiting angiogenesis, in effecting TGF-β activity, in diagnosing diseases, and in treating ischemia, spinal cord injury, demyelinating diseases, Parkinson's disease, ALS, alcohol dependence, nicotine dependence, cocaine dependence, prostate disease, cancer, diabetic neuropathy, pain, schizophrenia, anxiety, anxiety disorder and memory impairment. The present inventors have discovered that the inventive compounds are effective NAALADase inhibitors. Thus, the inventive compounds are expected to have the same uses as the NAALADase inhibitors disclosed in the patents, patent applications and publications incorporated by reference.

PHARMACEUTICAL COMPOSITIONS OF THE INVENTION

This invention also relates to a pharmaceutical composition comprising:

(i) an effective amount of a compound of the invention; and (ii) a pharmaceutically acceptable carrier.

Preferably, the compound of the invention is present in an effective amount for inhibiting NAALADase enzyme activity or angiogenesis, effecting a neuronal activity or TGF-P activity, or treating a glutamate abnormality, compulsive disorder, prostate disease, cancer or glaucoma in an animal or a mammal.

Route of Administration

The inventive compounds and compositions may be administered locally or systemically by any means known to an ordinarily skilled artisan. For example, the inventive compounds and compositions may be administered orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intraarterial, intramuscular, intraperitoneal, intrathecal, intraventricular, intrasternal, intracranial or intraosseous injection and infusion techniques. The exact administration protocol will vary depending upon various factors including the age, body weight, general health, sex and diet of the patient; the determination of specific administration procedures would be routine to an ordinarily skilled artisan.

To be effective therapeutically as central nervous system targets, the inventive compounds and compositions should readily penetrate the blood-brain barrier when peripherally administered. Compounds that cannot penetrate the blood-brain barrier can be effectively administered by an intraventricular route or by other methods recognized in the art. See, for example, U.S. Pat. Nos. 5,846,565, 5,651,986 and 5,626,862.

Dosage

The inventive compounds and compositions may be administered by a single dose, multiple discrete doses or continuous infusion. Pump means, particularly subcutaneous pump means, are preferred for continuous infusion.

Dose levels on the order of about 0.001 to about 10,000 mg/kg of the active ingredient compound are useful in the treatment of the above conditions, with preferred levels being about 0.1 to about 1,000 mg/kg, and more preferred levels being about 1 to about 100 mg/kg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Administration Regimen

Any administration regimen well known to an ordinarily skilled artisan for regulating the timing and sequence of drug delivery can be used and repeated as necessary to effect treatment. Such regimen may include pretreatment and/or co-administration with additional therapeutic agents.

Co-Administration With Other Treatments

The inventive compounds and compositions may be used alone or in combination with one or more additional agent(s) for simultaneous, separate or sequential use.

The additional agent(s) may be any therapeutic agent(s) known to an ordinarily skilled artisan, including without limitation: one or more compound(s) of the invention; steroids, for example, hydrocortisones such as methylprednisolone; anti-inflammatory or anti-immune drugs, such as methotrexate, azathioprine, cyclophosphamide or cyclosporin A; interferon-β; antibodies, such as anti-CD4 antibodies; agents which can reduce the risk of a second ischemic event, such as ticlopidine; chemotherapeutic agents; immunotherapeutic compositions; electromagnetic radiosensitizers; and morphine.

The inventive compounds and compositions can be co-administered with one or more therapeutic agents either together in a single formulation, or separately in individual formulations designed for optimal release rates of their respective active agent. Each formulation may contain from about 0.01% to about 99.99% by weight, preferably from about 3.5% to about 60% by weight, of a compound of this invention, as well as one or more pharmaceutically acceptable carriers.

Preparation of Compounds

The inventive compounds can be readily prepared by standard techniques of organic chemistry, utilizing the general synthetic pathways depicted below in SCHEMES I, II, and III. Precursor compounds are either commercially available or may be prepared by methods known to a person of skill in the art.

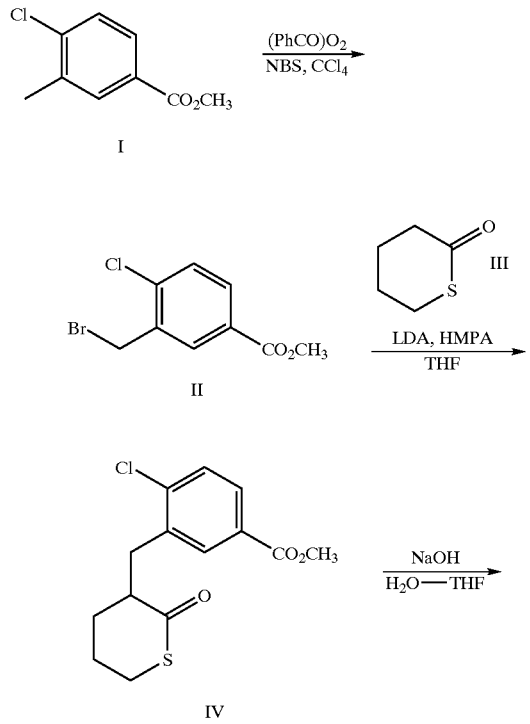

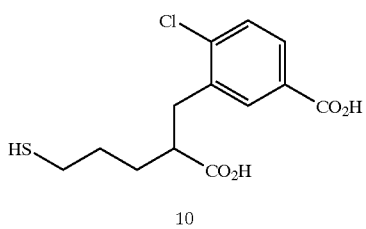

SCHEME II

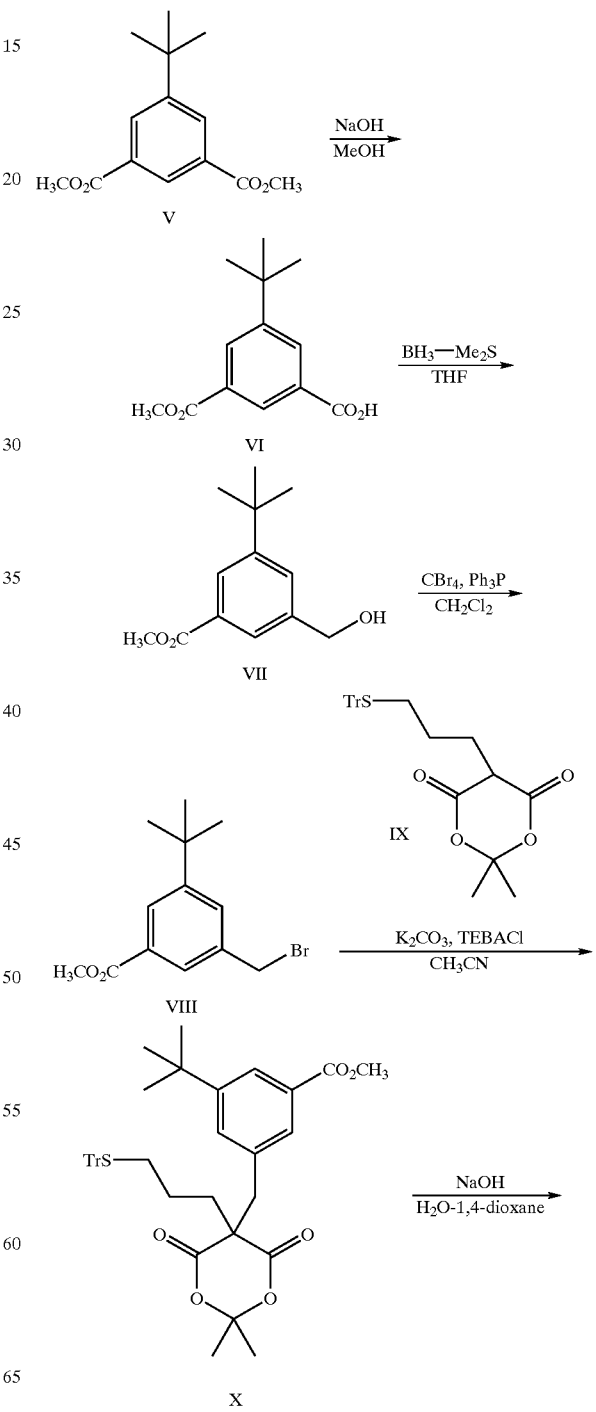

-continued

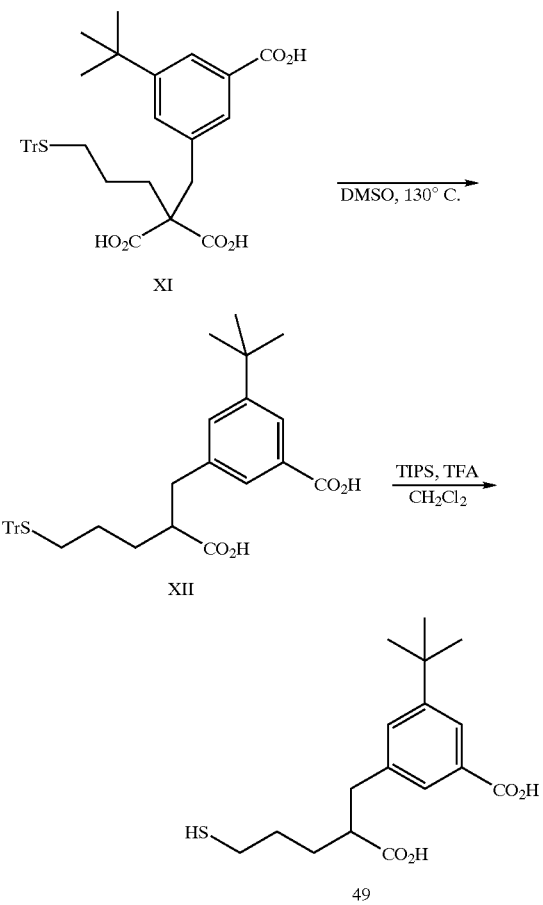

EXAMPLES

The following examples are illustrative of this invention and are not intended to be limitations thereon. Unless otherwise indicated, all percentages are based upon 100% by weight of the final composition.

Example 1

Preparation of 5-Carboxy-2-chloro-alpha-(3-mercaptopropyl)-benzenepropanoic Acid 10
(Scheme I)

Methyl 3-Bromomethyl-4-chlorobenzoate II

To a suspension of methyl 4-chloro-3-methylbenzoate I (19.9 g, 108 mmol) and N-bromosuccinimide (NBS, 20.2 g, 114 mmol) in carbon tetrachloride (500 mL) was added benzoyl peroxide (1.30 g, 5.4 mmol), and the mixture was stirred at 90° C. overnight. The mixture was then cooled and the white precipitate was removed by filtration. The filtrate was concentrated and the resulting solid was re-crystallized from ethyl acetate to give methyl 3-bromomethy-4-chlorobenzoate II (15.0 g, 57 mmol, 53%) as a white solid: $^1$H NMR (CDCl$_3$) δ 3.95 (s, 3H), 4.63 (s, 2H), 7.49 (d, J=8.3 Hz, 1H), 7.94 (dd, J=2.1, 8.3 Hz, 1H), 8.15 (d, J=2.1 Hz, 1H).

3-(2-Chloro-5-methoxycarbonylbenzyl)-tetrahydrothiopyrane-2-one IV

To a solution of lithium diisopropylamide (2.0 M solution, 3.3 mL, 6.6 mmol) in THF (25 mL) was added tetrahydrothiopyran-2-one III (0.731 g, 6.3 mmol) at −40° C., and the mixture was stirred at −40° C. for 45 minutes. A solution of methyl 3-bromomethy-4-chlorobenzoate II (1.67 g, 6.3 mmol) in THF (10 mL) was then dropwise added to the mixture at −40° C. Subsequently, hexamethylphosphoramide (0.20 g, 1.4 mmol) was added to the mixture at −40° C., and the reaction mixture was stirred at −40° C. for 4 hours. A saturated ammonium chloride solution (30 mL) was added to the reaction mixture, and the organic solvent was removed under reduced pressure. The mixture was then partitioned between ether (150 mL) and H$_2$O (150 mL). The organic layer was washed with brine, dried over MgSO$_4$, and concentrated. The crude material was chromatographed on silica gel using EtOAc/hexanes to afford 3-(2-chloro-5-methoxycarbonylbenzyl)-tetrahydrothio-pyrane-2-one IV (0.60 g, 2.0 mmol, 32%) as a white solid: $^1$H NMR (CDCl$_3$) δ 1.65–1.75 (m, 1H), 1.90–2.05 (m, 2H), 2.05–2.15 (m, 2H), 2.74 (dd, J=9.4, 13.9 Hz, 1H), 2.85–3.00 (m, 1H), 3.10–3.20 (m, 2H), 3.58 (dd, J=4.7, 13.9 Hz, 1H), 3.92 (s, 3H), 7.44 (d, J=8.3 Hz, 1H), 7.85 (dd, J=8.3, 2.1 Hz, 1H), 7.91 (d, J=2.1 Hz, 1H).

5-Carboxy-2-chloro-alpha-(3-mercaptopropyl)benzenepropanoic Acid 10

A solution of 3-(2-Chloro-5-methoxycarbonylbenzyl)-tetrahydrothiopyrane-2-one IV (9.26 g, 31.0 mmol) in THF (70 mL) was purged for 15 minutes with nitrogen. A degassed aqueous sodium hydroxide solution (2.2 M, 70 mL, 154 mmol) was added to the solution and the mixture was stirred at room temperature under nitrogen overnight. The reaction mixture was washed with ether, acidified by 3N HCl at 0° C., and extracted with ether. The extract was dried over MgSO$_4$ and concentrated to afford 5-carboxy-2-chloro-alpha-(3-mercaptopropyl)benzenepropanoic acid 10 (8.42 g, 27.8 mmol, 90%) as a white solid: $^1$H NMR (CD$_3$OD) δ 1.50–1.80 (m, 4H), 2.35–2.50 (m, 2H), 2.65–2.75 (m, 1H), 2.91 (dd, J=6.2, 13.8 Hz, 1H), 2.96 (dd, J=8.8, 13.8 Hz, 1 H), 7.39 (d, J=8.3 Hz, 1H), 7.76 (dd, J=2.0, 8.3 Hz, 1H), 7.86 (d, J=2.0 Hz, 1H); $^{13}$C NMR (CD$_3$OD) δ 25.1, 32.5, 33.2, 37.4, 46.8, 130.8, 131.2, 134.0, 139.1, 140.5, 169.2, 178.9. Anal.

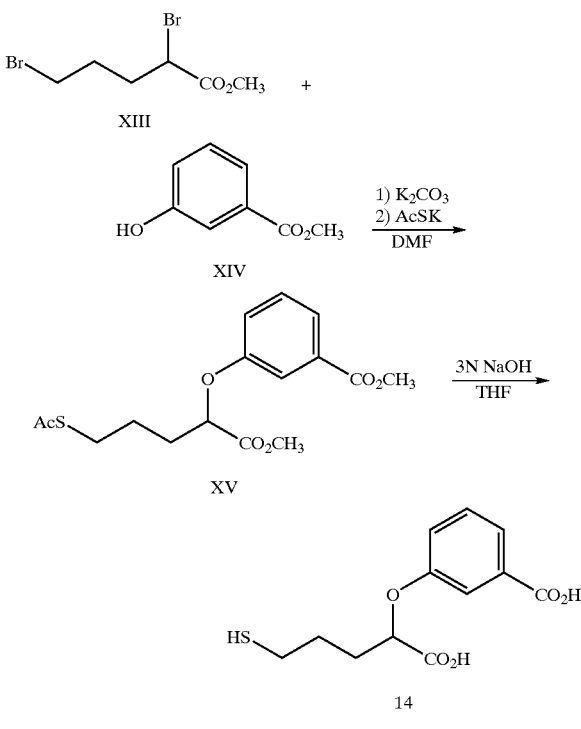

Calcd for C$_{13}$H$_{15}$ClO$_4$S: C, 51.57; H, 4.99; S, 10.59; Cl, 11.71. Found: C, 51.59; H, 4.94; S, 10.43; Cl, 11.80.

Example 2

Preparation of 3-Carboxy-5-(1,1-dimethylethyl)-alpha-(3-mercaptopropyl)-benzenepropanoic Acid 49 (Scheme II)

Methyl 5-tert-Butylhydrogenisophthalate VI

To a solution of dimethyl 5-tert-butylisophthalate V (23.0 g, 92 mmol) in methanol (150 mL) was added a solution of sodium hydroxide (3.68 g, 92 mmol) in H$_2$O (10 mL) at 25° C., and the mixture was stirred at 25° C. for 3 hours. The organic solvent was removed under reduced pressure and the residual solid was suspended in an aqueous sulfuric acid solution (1.0 M). The suspension was filtered and the precipitate was washed with H$_2$O, dried under vacuum, and crystallized from hexanes/ethyl acetate to afford methyl 5-tert-butylhydrogenisophthalate VI (16.3 g, 69.0 mmol, 75%) as a white solid: $^1$H NMR (CDCl$_3$) δ 1.45 (s, 9H), 3.9 (s, 3H), 8.5 (s, 1H), 8.7 (s, 1H), 8.8 (s, 1H); $^{13}$C NMR (CDCl$_3$) δ 31.3 (3C), 35.2, 52.5, 128.8, 129.7, 130.7, 131.1, 131.6, 132.0, 166.7, 171.5.

Methyl 3-tert-Butyl-5-hydroxymethylbenzoate VII

Borane-dimethyl sulfide complex (7.23 mL, 76.2 mmol) was slowly added to a solution of methyl 5-tert-butylhydrogenisophthalate VI (12.0 g, 50.8 mmol) in THF (100 ml) over the period of 20 minutes at room temperature. The mixture was stirred for 1.5 hours at room temperature and then refluxed for 1 additional hour. The reaction mixture was then cooled and the unreacted borane was decomposed with methanol (10 mL). The solvents were removed under reduced. pressure and the residue was dissolved in ethyl acetate. The organic solution was washed with a saturated NaHCO$_3$ solution, dried over MgSO$_4$, and purified by a silica gel column chromatography (hexane/ethyl acetate) to afford methyl 3-tert-butyl-5-hydroxymethylbenzoate VII (10.0 g, 45.0 mmol, 90%) as a white solid: $^1$H NMR (CDCl$_3$) δ 1.45 (s, 9H), 3.9 (s, 3H), 4.7 (s, 2H), 7.6 (s, 1H), 7.8 (s, 1H), 8.0 (s, 1H); $^{13}$C NMR (CDCl$_3$) δ 31.4 (3C), 35.0, 52.3, 65.3, 125.5, 126.1, 128.8, 130.3, 141.0, 152.1, 167.5.

Methyl 3-Bromomethyl-5-tert-butylbenzoate VIII

To a solution of methyl 3-tert-butyl-5-hydroxymethylbenzoate VII (9.50 g, 42.7 mmol) and carbon tetrabromide (17.25 g, 52.0 mmol) in dichloromethane (50 mL) was slowly added triphenylphosphine (13.6 g, 52.0 mmol) over the period of 20 minutes, and the mixture was stirred at room temperature for 25 minutes. The reaction mixture was concentrated under reduced pressure and the residue was suspended in ethyl acetate. The precipitate was removed by filtration and the filtrate was concentrated. The crude material was purified by a silica gel chromatography (hexanes/ethyl acetate, 4:1), and the product was re-crystallized form ethyl acetate/hexanes to afford methyl 3-bromomethyl-5-tert-butylbenzoate VIII (12.0 g, 42.1 mmol, 99%) as a white solid: $^1$H NMR (CDCl$_3$) δ 1.45 (s, 9H), 3.7 (s, 3H), 4.4 (s, 2H), 7.6 (s, 1H), 7.8 (s, 1H), 8.0 (s, 1H); $^{13}$C NMR (CDCl$_3$) δ 31.3 (3C), 33.2, 36.0, 52.3, 126.9, 127.5, 130.6, 130.7, 137.9, 152.4, 167.0.

5-(3-tert-Butyl-5-methoxycarbonyl-benzyl)-2,2-dimethyl-5-[3-[(triphenylmethyl)thio]propyl]-[1,3]dioxane-4,6-dione X A solution of methyl 3-bromomethyl-5-tert-butylbenzoate (10.3 g, 36.1 mmol), 2,2-dimethyl-5-[3-[(triphenylmethyl)-thio]propyl]-[1,3]dioxane-4,6-dione IX (13.8 g, 30.0 mmol), and benzyltriethylammonium chloride (6.38 g, 30 mmol) in acetonitrile (90 mL) was added potassium carbonate (4.35 g, 30 mmol) at 25° C., and the reaction mixture was stirred at 60° C. overnight (the synthesis of compound IX was previously described in International Publication No. WO 00/01668). The solvent was removed under reduced pressure and the residue was partitioned between ethyl acetate and a 10% aqueous KHSO$_4$ solution. The organic layer was dried over MgSO$_4$, concentrated. The crude material was recrystallized from ethyl acetate/hexane mixture to afford 5-(3-tert-butyl-5-methoxycarbonyl-benzyl)-2,2-dimethyl-5-[3-[(triphenyl-methyl)thio]propyl]-[1,3]dioxane-4,6-dione X (14.0 g, 79%) as a white solid: $^1$H NMR (CDCl$_3$) δ 0.7 (s, 3H), 1.3 (s, 9H), 1.2–1.3 (m, 2H), 1.5 (s, 3H), 2.0 (m, 2H), 2.2 (m, 2H), 3.3 (s, 2H), 3.8 (s, 3H), 7.2–7.4 (m, 16H), 7.6 (s, 1H), 7.8 (s, 1H); 13C NMR (CDCl$_3$) δ 24.8, 29.1, 29.4, 31.2, 31.4, 34.9, 40.3, 43.7, 52.3, 57.3, 66.8, 105.8, 126.0, 126.8, 128.0, 128.5, 129.6, 130.5, 132.3, 135.3, 144.8, 152.4, 167.1, 168.5.

2-(3-tert-Butyl-5-methoxycarbonyl-benzyl)-2-[3-[(triphenylmethyl)thio]propyl]-malonic Acid XI To a solution of 5-(3-tert-butyl-5-methoxycarbonyl-benzyl)-2,2-dimethyl-5-[3-[(triphenylmethyl)thio]propyl]-[1,3]dioxane-4,6-dione X (11 g, 16.5 mmol) in 1,4-dioxane (15 ml) was added a solution of sodium hydroxide (4.63 g, 115.5 mmol) in H$_2$O (15 mL) at 25° C., and the mixture was stirred at 100° C. for 1 hour. The solvent was removed under reduced pressure and the residue was partitioned between ethyl acetate and a 10% aqueous KHSO$_4$ solution. The organic layer was dried over MgSO$_4$, concentrated. The crude material was recrystallized from ethyl acetate/hexane mixture to afford 2-(3-tert-butyl-5-methoxycarbonyl-benzyl)-2-[3-[(triphenyl-methyl)thio]propyl]malonic acid XI (9.0 g, 90%) as a white solid: $^1$H NMR (CD$_3$OD) δ 1.4 (s, 9H), 1.4 (m, 2H), 1.6 (m, 2H), 2.1 (t, J=8.0 Hz, 2H), 3.2 (s, 2H), 7.1–7.4 (m, 16H), 7.7 (s, 1H), 7.9 (s, 1H); $^{13}$C NMR (CD$_3$OD) δ 24.8, 31.8 (3C), 32.4, 33.3, 35.6, 39.0, 59.5, 67.7, 126.2., 127.7, 128.9, 129.6, 130.7, 131.5, 132.9; 137.8, 146.2, 152.6, 170.1, 174.5.

2-(3-tert-Butyl-5-methoxycarbonyl-benzyl)-5-[(triphenylmethyl)thio]pentanoic Acid XII A solution of 2-(3-tert-butyl-5-methoxycarbonyl-benzyl)-2-[3-[(triphenylmethyl)thio]propyl]-malonic acid XI (6.71 g, 11 mmol) in DMSO (10 ml) was stirred at 130° C. for 1.5 hours. The solvent was removed under reduced pressure and water was added to the residual oil. The precipitate was filtered off, washed with water, and dried under vacuum to afford 2-(3-tert-butyl-5-methoxycarbonyl-benzyl)-5-[(triphenylmethyl)thio]-pentanoic acid XII (5.86 g, 10.3 mmol, 94%) as a white solid: $^1$H NMR (CD$_3$OD) δ 1.3 (s, 9H), 1.3–1.5 (m, 4H), 2.1 (m, 2H), 2.4 (m, 1H), 2.7 (m, 1H), 2.8 (m, 1H), 7.1–7.4 (m, 16H), 7.7 (s, 1H), 7.9 (s, 1H); $^{13}$C NMR (CD$_3$OD) 627.4, 31.7 (3C), 32.3, 32.7, 35.6, 39.2, 48.4, 67.7, 125.7, 127.7, 128.6, 128.9, 130.8, 131.6, .132.0, 140.8, 146.3, 152.7, 170.3, 178.8.

3-Carboxy-5-(1,1-dimethylethyl)-alpha-(3-mercaptopropyl)-benzenepropanoic Acid 49

To a solution of 2-(3-tert-butyl-5-methoxycarbonyl-benzyl)-5-[(triphenylmethyl)thio]pentanoic acid XII (5.5 g, 9.7 mmol) in dichloromethane (30 mL) were added triisopropylsilane (2.4 mL, 11.6 mmol) and trifluoroacetic acid (10 mL), and the mixture was stirred at room temperature for 10 minutes. The solvent was removed under reduced pressure and the crude material was purified by silica gel chromatography (1% AcOH in Hexanes/EtOAc, 4:1) to afford 3-carboxy-5-(1,1-dimethylethyl)-alpha-(3-mercaptopropyl)-benzenepropanoic acid 49 (1.7 g, 5.3 mmol, 55%) as a white solid: $^1$H NMR (CD$_3$OD) δ 1.3 (s, 9H), 1.5–1.8 (m, 4H), 2.4 (m, 2H), 2.6–2.7 (m, 1H), 2.8–2.9 (m, 1H), 2.9–3.0 (m, 1H), 7.5 (s, 1H), 7.7 (s, 1H), 7.8 (s, 1H); $^{13}$C NMR (CD$_3$OD) δ 24.8, 31.7 (3C), 31.9, 32.9, 35.6, 39.5, 48.6, 125.7, 128.5, 131.6, 132.0, 140.9, 152.8, 170.3, 179.0. Anal. Calcd for C$_{17}$H$_{24}$O$_4$S: C, 62.93; H, 7.46; S, 9.88. Found: C, 63.02; H, 7.36; S, 9.82.

Example 3

Preparation of 3-(1-Carboxy-4-mercaptobutoxy)-benzoic Acid 14 (Scheme III)

Methyl 3-(4-Acetylthio-1-methoxycarbonyl-butoxy)-benzoate XV

To a solution of methyl 2,5-dibromopentanoate XIII (22.00 g, 80.3 mmol) and methyl 3-hydroxybenzoate XIV (10.18 g, 66.9 mmol) in DMF (80 mL) was added K$_2$CO$_3$ (12.94 g, 93.7 mmol) at room temperature. The mixture was stirred at room temperature under N$_2$ for 12 hours, then heated at 70° C. for 1 h. Potassium thioacetate (22.93 g, 200.8 mmol) was added to the mixture, which was heated at 70° C. for 2 hours. The mixture was allowed to cool to room temperature and was diluted with EtOAc (1000 mL). The mixture was washed with H$_2$O (3×300 mL) and brine (2×300 mL). The organic layer was dried over MgSO$_4$, filtered and concentrated. The crude product was purified by flash chromatography (gradient elution: 10% to 20% EtOAc/hexanes) to afford methyl 3-(4-acetylthio-1-methoxycarbonyl-butoxy)-benzoate XV (8.40 g, 24.7 mmol, 37%) as a yellow oil: R$_f$ 0.26 (hexanes/EtOAc, 4:1): $^1$H NMR (CDCl$_3$) δ 1.73–1.88 (m, 2H), 2.01–2.08 (m, 2H), 2.32 (s, 3H), 2.93 (t, J=7.2 Hz, 2H), 3.75 (s, 3H), 3.89 (s, 3H), 4.69 (t, J=6.2 Hz, 1H), 7.07 (dm, J=8.0 Hz, 1H), 7.33 (t, J=7.9 Hz, 1H), 7.50 (m, 1H), 7.65 (dm, J=7.7 Hz, 1H); $^{13}$C NMR (CDCl$_3$) δ 25.3, 28.3, 30.5, 31.4, 52.1, 52.2, 75.8, 115.4, 120.0, 122.8, 129.5, 131.4, 157.5, 166.4, 171.3, 195.4.

3-(1-Carboxy-4-mercaptobutoxy)-benzoic Acid 14

A solution of methyl 3-(4-acetylthio-1-methoxy-carbonylbutoxy)benzoate XV (8.00 g, 23.5 mmol) in THF (60 mL) was deoxygenated by bubbling N$_2$ through the solution for 1 hour. To the solution was added deoxygenated 3 N NaOH (47 mL, 141 mmol) and the mixture was stirred for 24 hours at room temperature under N$_2$. The mixture was acidified with 1 N HCl and extracted with EtOAc (3×300 mL). The organic extracts were washed with water (300 mL) and brine (300 mL), dried over MgSO$_4$, filtered, and concentrated. The residual oil was dissolved in ether and the solution was concentrated to afford 3-(1-carboxy-4-mercaptobutoxy)-benzoic acid 14 (4.40 g, 16.3 mmol, 69%) as a white solid: $^1$H NMR (CDCl$_3$) δ 1.40 (t, J=7.9 Hz, 1H), 1.83–1.99 (m, 2H), 2.11–2.22 (m, 2H), 2.63 (m, 2H), 4.76 (dd, J=7.3, 5.0 Hz, 1H), 7.23 (m, 1H), 7.38 (t, J=7.8 Hz, 1H), 7.49 (m, 1H), 7.72 (d, J=7.7 Hz, 1H); $^{13}$C NMR (CDCl$_3$) δ 24.1, 29.6, 31.2, 75.5, 114.8, 122.1, 123.9, 129.9, 130.5, 157.6, 171.8, 177.1. Anal. Calcd for C$_{12}$H$_{14}$O$_5$S: C, 53.32; H, 5.22; S, 11.86. Found: C, 53.04; H, 5.38; S, 11.58.

Example 4

Preparation of (+)-3-Carboxy-α-(3-mercaptopropyl)-benzenepropanoic Acid 53 and (−)-3-Carboxy-α-(3-mercaptopropyl)-benzenepropanoic Acid 54

A solution of racemic 3-carboxy-α-(3-mercaptopropyl)-benzenepropanoic acid (2.70 g, 10.1 mmol) was divided into multiple samples of equal volume, and each of them was passed through a CHIRAPAK AD column (250 mm×21 mm id) using carbon dioxide/methanol (77/23, v/v) as eluent at a flow rate of 25 mL/min, at 25° C. The first eluting peak (detected by UV at 290 nm) from each run was combined and concentrated to afford (+)-3-carboxy-α-(3-mercaptopropyl)-benzenepropanoic acid 53 (1.02 g, 38%) as a colorless oil: [α]$^{25}$D=+15.5 (c=1.1, CH3CN). (−)-3-carboxy-α-(3-mercaptopropyl)-benzenepropanoic acid 54 (1.08 g. 40%) was obtained likewise from the second peaks as a colorless oil: [α]$^{25}$D=−13.4 (c=1.1, CH$_3$CN).

Example 5

In Vitro Inhibition of NAALADase Activity

Various compounds of this invention were tested for in vitro inhibition of NAALADase activity, and the results are provided below in TABLE II.

TABLE II

| In Vitro Inhibition of NAALADase Activity | |
|---|---|
| Compound No. | IC$_{50}$ |
| 1 | 4000 |
| 2 | 2270 |
| 3 | 2140 |
| 4 | 1000 |
| 5 | 17 |
| 6 | 59 |
| 7 | 211 |
| 8 | 450 |
| 9 | 2.55 |
| 10 | 2.09 |
| 11 | 12 |
| 12 | 316 |
| 13 | 3950 |
| 14 | 16.3 |
| 15 | 555 |
| 16 | 16,100 |
| 17 | 566 |
| 18 | 308 |
| 19 | 846 |
| 20 | 64 |
| 21 | 82 |
| 22 | 229 |
| 23 | 2900 |
| 24 | 27700 |
| 25 | 29.8 |
| 26 | 2200 |
| 27 | 287 |
| 28 | 809 |
| 29 | 4600 |
| 30 | 192 |
| 31 | 1200 |
| 32 | 175 |
| 33 | 118 |
| 34 | 400 |
| 35 | 6.33 |
| 36 | 26 |
| 37 | 316 |
| 38 | 1700 |
| 39 | 660 |
| 40 | 297 |
| 41 | 24 |
| 42 | 1130 |
| 43 | 1350 |
| 44 | 1130 |
| 45 | 2.5 |
| 46 | 286 |
| 47 | 146 |
| 48 | 3 |
| 49 | 0.05 |
| 50 | 8.25 |
| 51 | 1.83 |
| 52 | 3.33 |
| 53 | 7 |
| 54 | 33.3 |
| 56 | 19 |
| 57 | 70 |
| 58 | 18 |

TABLE II-continued

In Vitro Inhibition of NAALADase Activity

| Compound No. | IC$_{50}$ |
|---|---|
| 59 | 13 |
| 60 | 184 |
| 61 | 49 |
| 62 | 3590 |
| 63 | 30 |
| 64 | 87 |
| 66 | 181 |
| 67 | 5 |
| 68 | 1 |

Protocol for Assaying In Vitro Inhibition of NAALADase Activity

The following were combined in assay tubes: 100 μL of 10 mM CoCl$_2$, 250 μL of 200 mM Tris chloride, 100 μL tissue, 100 μL of 10 mM NAALADase inhibitor in Bakers H$_2$O, and Bakers H$_2$O to make a total volume of 950 μL. Each assay tube was then incubated for 10 minutes in a 37EC water bath. 50 μL of 3-H-NAAG was then added to each assay tube and incubated for an additional 15 minutes in a 37EC water bath. The assay was stopped by adding 1.0 ml of 0.1 M sodium phosphate.

Glutamate released by the action of the NAALADase enzyme was separated from the assay solution using an anion exchange resin. The resin was equilibrated to 25EC, 2.0 ml of the resin was added to a Pasteur pipette pre-loaded with a single glass bead, and each column was washed twice with distilled H$_2$O. A column was placed over a scintillation vial and 200 μL of an assay sample was loaded onto the column. After draining, glutamate was eluted using two 1.0 ml washes of 1 M formic acid. After addition of 10 ml of scintillation cocktail, each sample was counted for 2 minutes on a scintillation counter.

Example 6

In Vitro Assay on Ischemia

To example the in vitro effect of the inventive compounds on ischemia, cortical cell cultures were treated with various compounds of this invention during an ischemic insult utilizing potassium cyanide and 2-deoxyglucose, and for one hour thereafter. For a description of the experimental method used, see Vornov et al., *J. Neurochem.*, Vol. 65, No. 4, pp. 681–1691 (1995). The results are provided below in TABLE III. Neuroprotective effect is expressed as EC$_{50}$, the centration of the compound, which is required to cause a 50% reduction in glutamate toxicity following an ischemic insult.

TABLE III

| Compound No. | EC$_{50}$ |
|---|---|
| 5 | 6.5 |
| 6 | 17.8 |
| 7 | 1060 |
| 8 | 133 |
| 9 | 104 |
| 10 | 7.7 |
| 11 | 15.4 |
| 12 | 188 |
| 13 | 10,000 |

TABLE III-continued

| Compound No. | EC$_{50}$ |
|---|---|
| 14 | 16 |
| 15 | 1,000 |
| 16 | 267 |
| 17 | 1400 |
| 18 | 230 |
| 20 | 39.3 |
| 21 | 11.6 |
| 23 | 21 |
| 26 | 1800 |
| 27 | 155 |
| 28 | 48 |
| 30 | 399 |
| 31 | 31 |
| 32 | 7 |
| 33 | 110 |
| 34 | 346 |
| 35 | 23 |
| 36 | 74.9 |
| 37 | 215 |
| 38 | 762 |
| 39 | 290 |
| 40 | 452 |
| 41 | 409 |
| 42 | 265 |
| 43 | 452 |
| 45 | 2 |
| 46 | 544 |
| 47 | 119 |
| 48 | 2.4 |
| 50 | 26 |
| 55 | 1 |
| 56 | 11 |
| 57 | 21 |
| 58 | 16 |

Example 7

Effect of NAALADase Inhibition on TGF-β in In Vitro Ischemia Model

Figure 2:
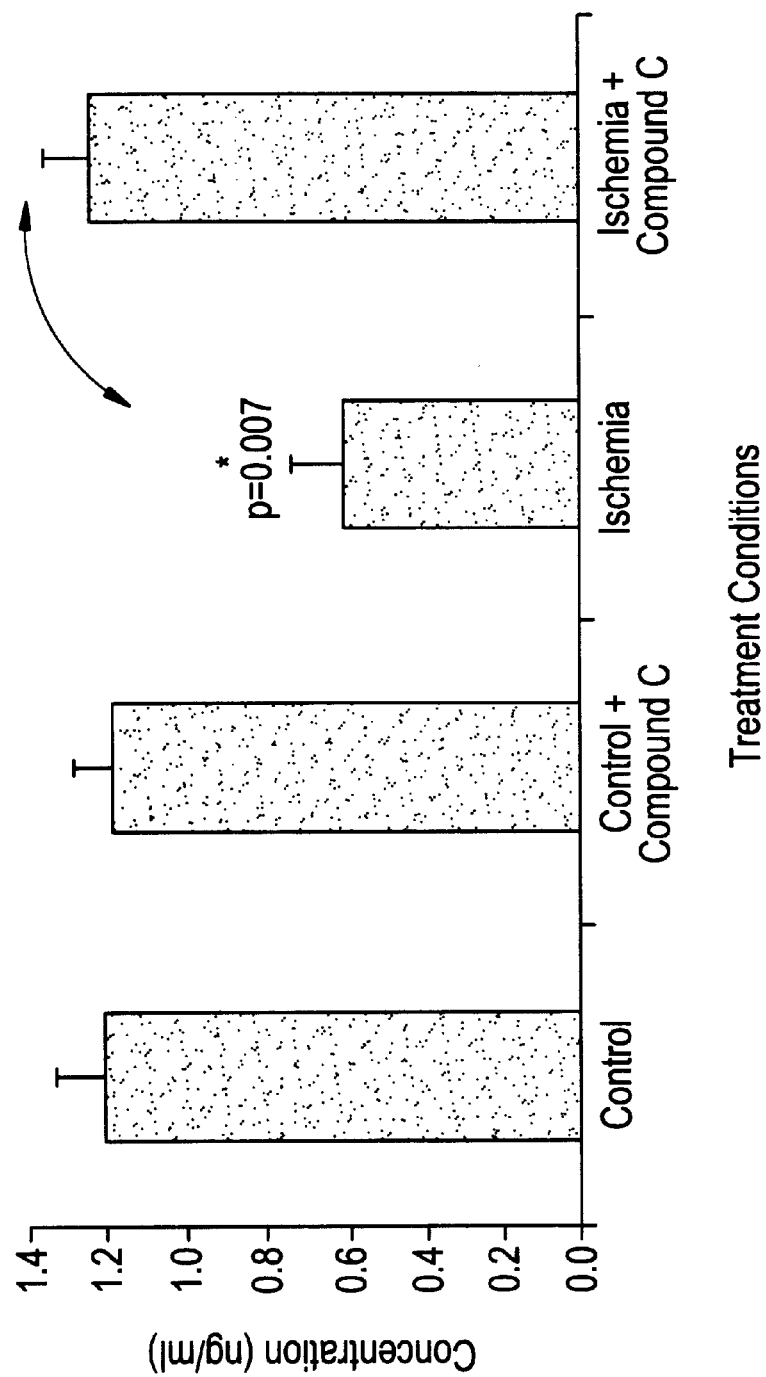
FIG. 2 is a bar graph showing the effect of Compound C on TGF-β2 concentrations in ischemic cell cultures.

A NAALADase inhibitor, Compound C, was added to ischemic cell cultures to determine its effect on TGF-β levels during stroke. The experimental data, set forth in FIGS. 1 and 2, show increased concentrations of TGF-β1 (FIG. 1) and TGF-β2 (FIG. 2) in ischemic cell cultures treated with Compound C. The results indicate that NAALADase inhibition promotes the release of endogenous TGF-β's from glial cells, which in turn provides neuroprotection for neighboring neurons.

Figure 3:
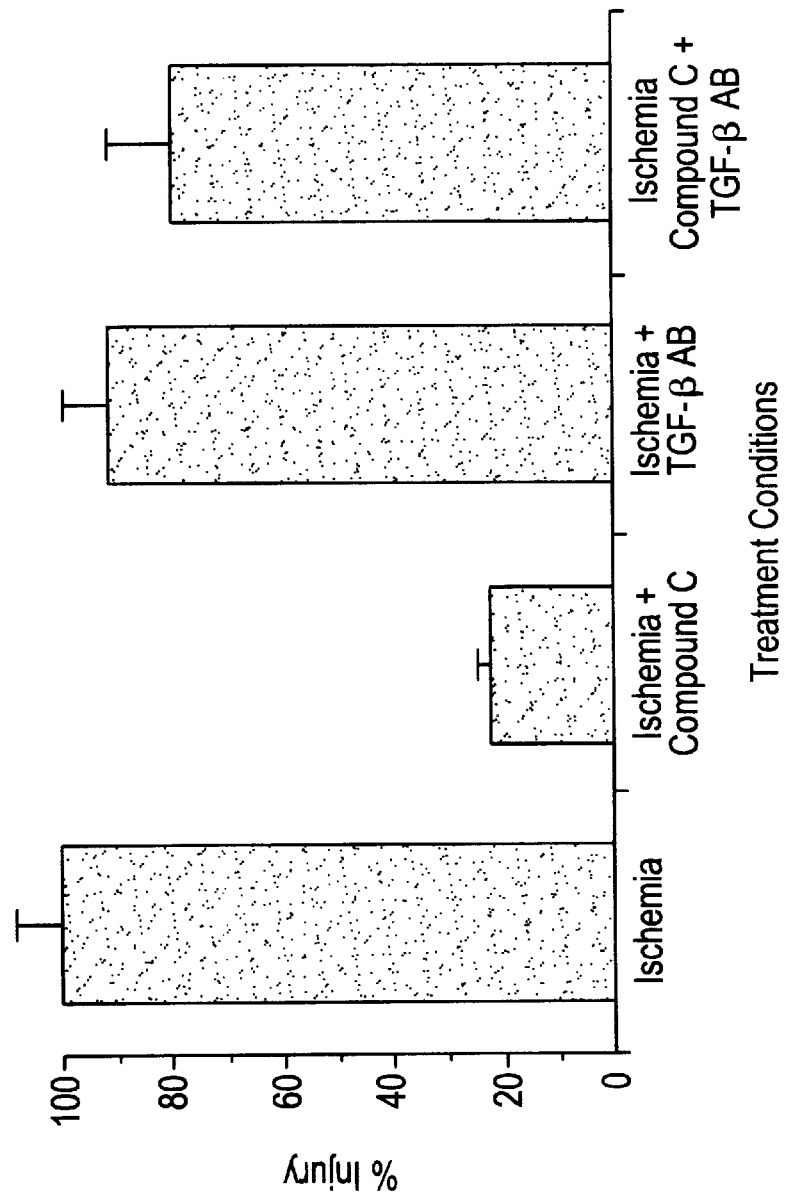
FIG. 3 is a bar graph showing the reversal of the neuroprotective effect of Compound C by TGF-β neutralizing antibodies in ischemic cell cultures.
Figure 4:
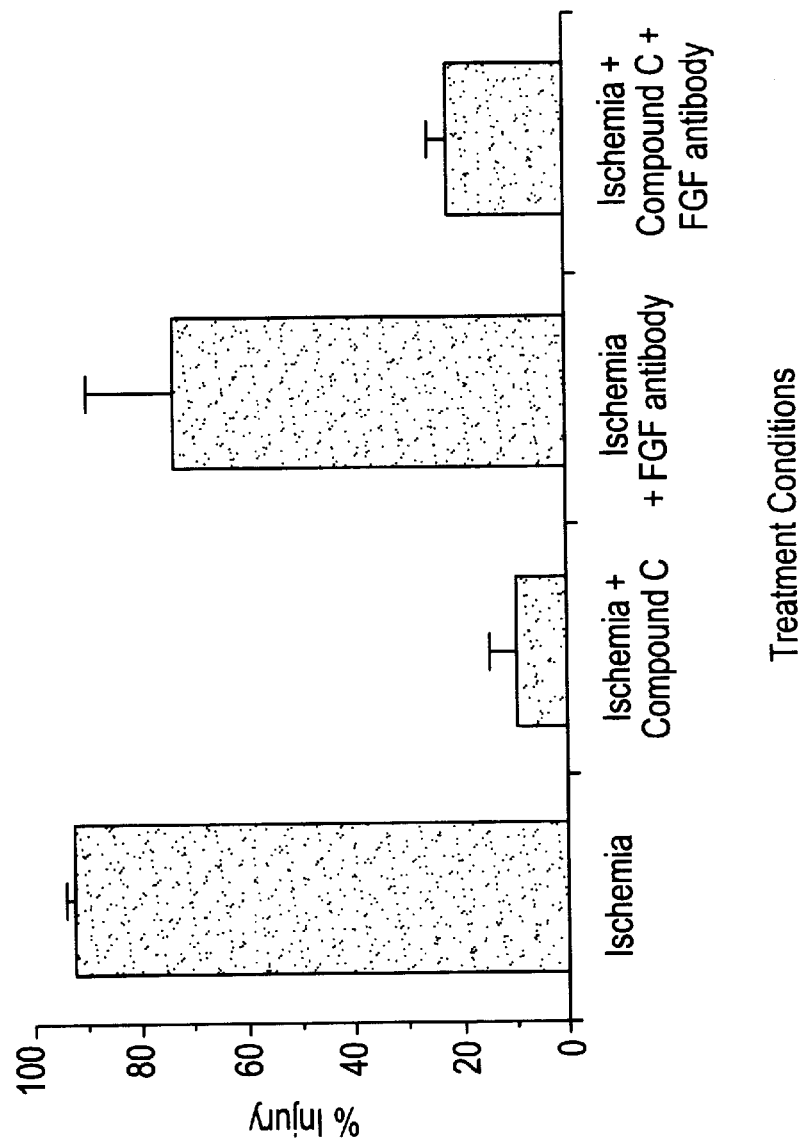
FIG. 4 is a bar graph showing the non-reversal of the neuroprotective effect of Compound C by FGF neutralizing antibodies in ischemic cell cultures.

TGF-β neutralizing antibodies were then added to the ischemic cell cultures. FIG. 3 shows that the TGF-P neutralizing antibodies blocked the neuroprotective effect of Compound C in the in vitro ischemia model. By contrast, FIG. 4 shows that the addition of another growth factor antibody, FGF antibody, did not block the neuroprotective effect of Compound C. The results indicate that NAALADase inhibition specifically affects TGF-β levels during stroke.

Example 8

Effect of NAALADase Inhibition on TGF-β in In Vivo Ischemia Model

Figure 6:
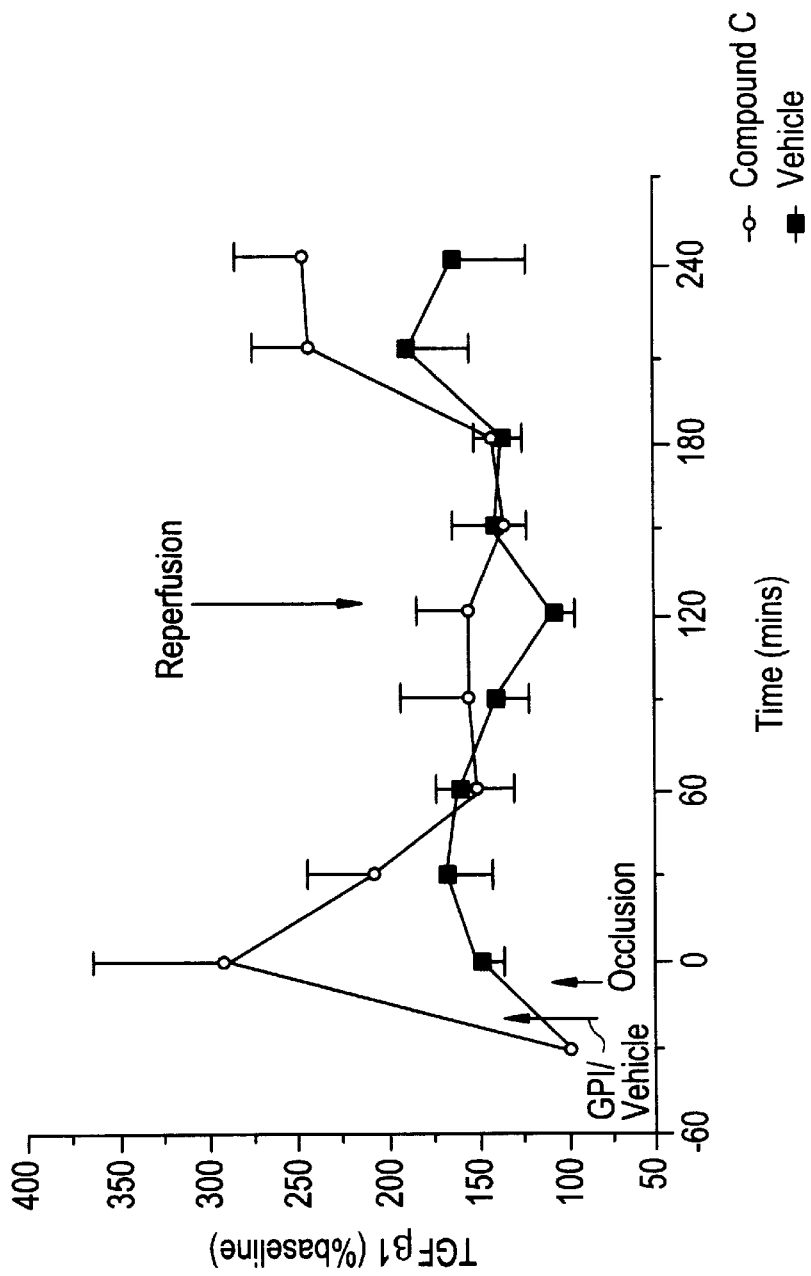
FIG. 6 is a bar graph showing the effect of Compound C on TGF-β1 levels during occlusion and reperfusion in rats subjected to MCAO.

The effect of TGF-β neutralizing antibodies on the neuroprotective effect of Compound C was also studied in rats following MCAO. FIG. 6 shows that treatment of MCAO rats with Compound C caused a significant rise in TGF-β1 levels during both occlusion and reperfusion, as assessed by microdialysis. The results indicate that NAALADase inhibition provides neuroprotection, at least in part, by regulating endogenous TGF-β's.

Figure 5:
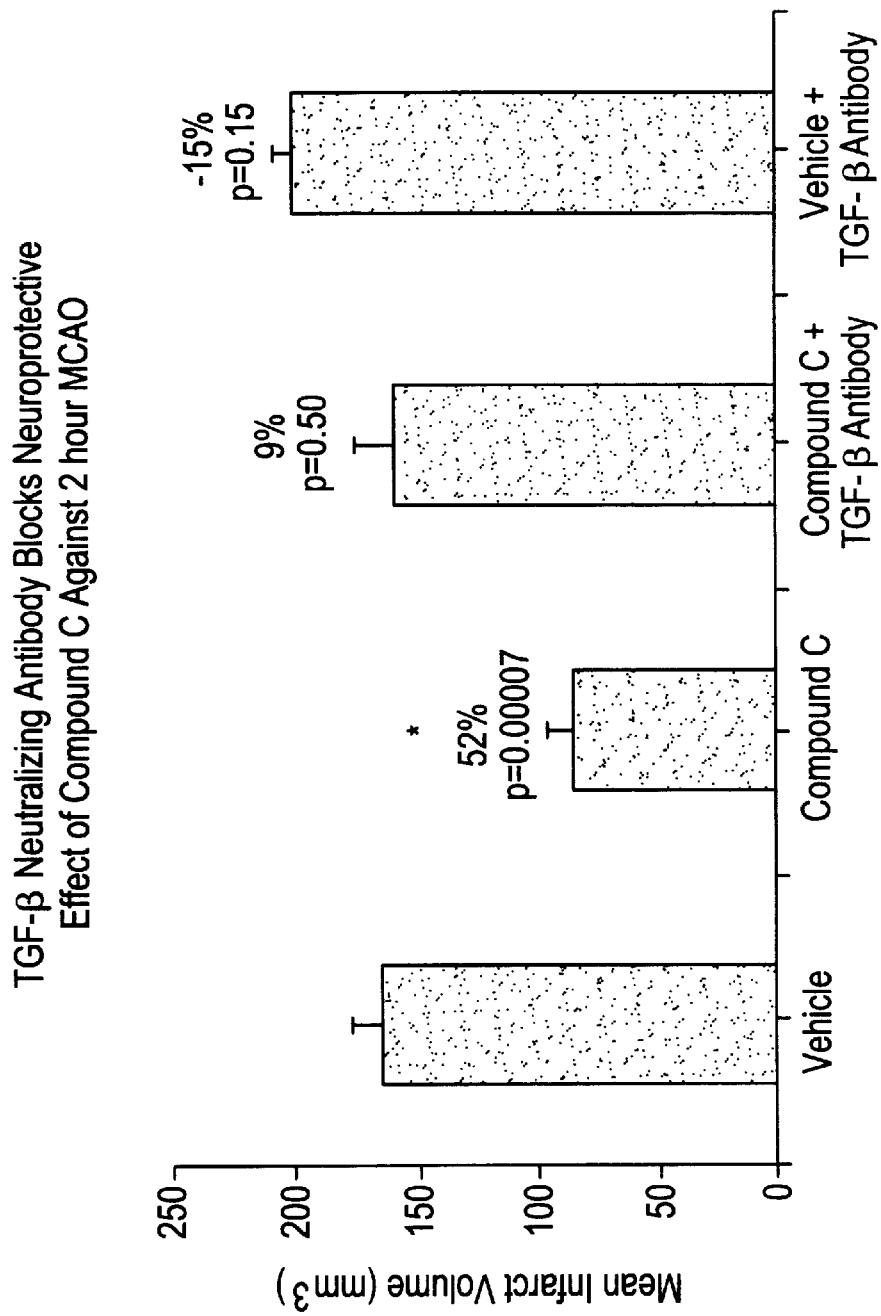
FIG. 5 is a bar graph showing the reversal of the neuroprotective effect of Compound C by TGF-β neutralizing antibodies in rats subjected to middle cerebral artery occlusion ("MCAO").

Additionally, FIG. 5 shows that TGF-β neutralizing antibodies significantly attenuated the neuroprotective effect of Compound C in vivo. One of ordinary skill in the art can appreciate that the regulation of TGF-β's by NAALADase inhibitors may have implications not only in stroke, but also in other diseases, disorders and conditions including, without limitation, neurological diseases, psychiatric diseases, demyelinating diseases, prostate cancer, inflammation, diabetes and angiogenesis.

Example 9

In Vivo Assay of NAALADase Inhibitors on Neuropathic Pain in STZ Model

Figure 7A:
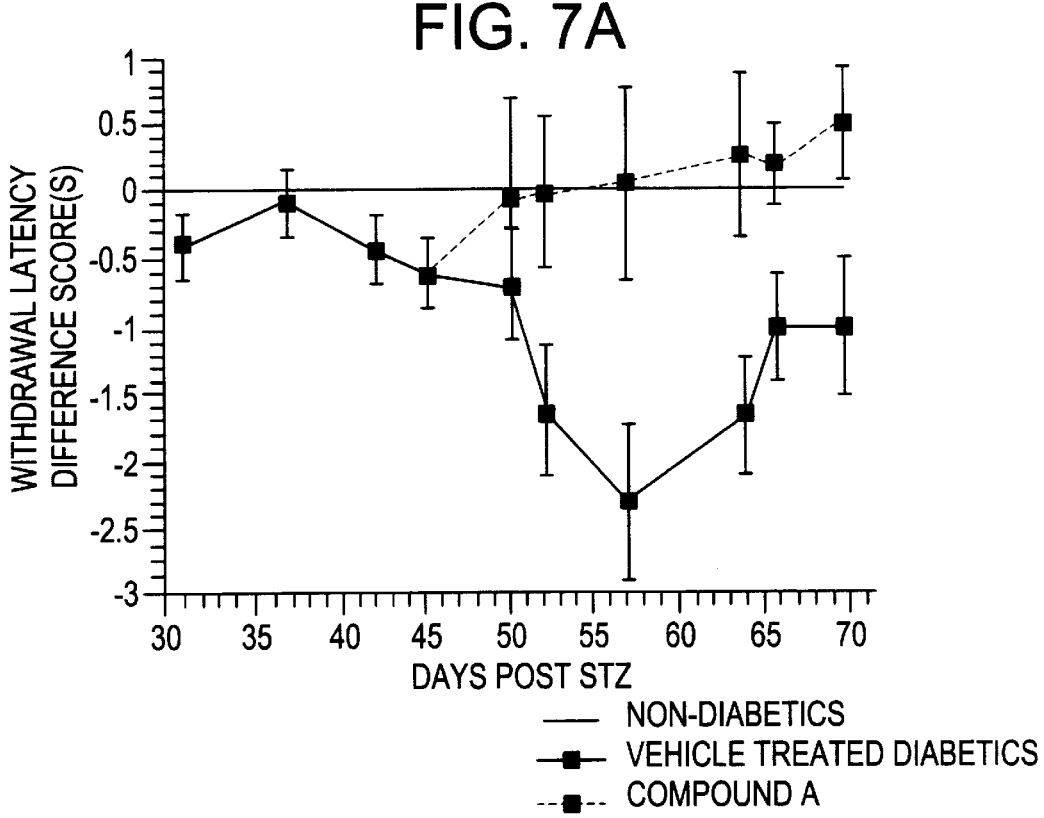
FIG. 7A is a bar graph plotting the withdrawal latency difference scores of non-diabetic rats and STZ-diabetic rats treated with a vehicle or 2-[[2,3,4,5,6-pentafluorobenzyl)hydroxyphosphinyl]methyl]pentanedioic acid ("Compound A"), against the days following administration with streptozotocin ("STZ").
Figure 7B:
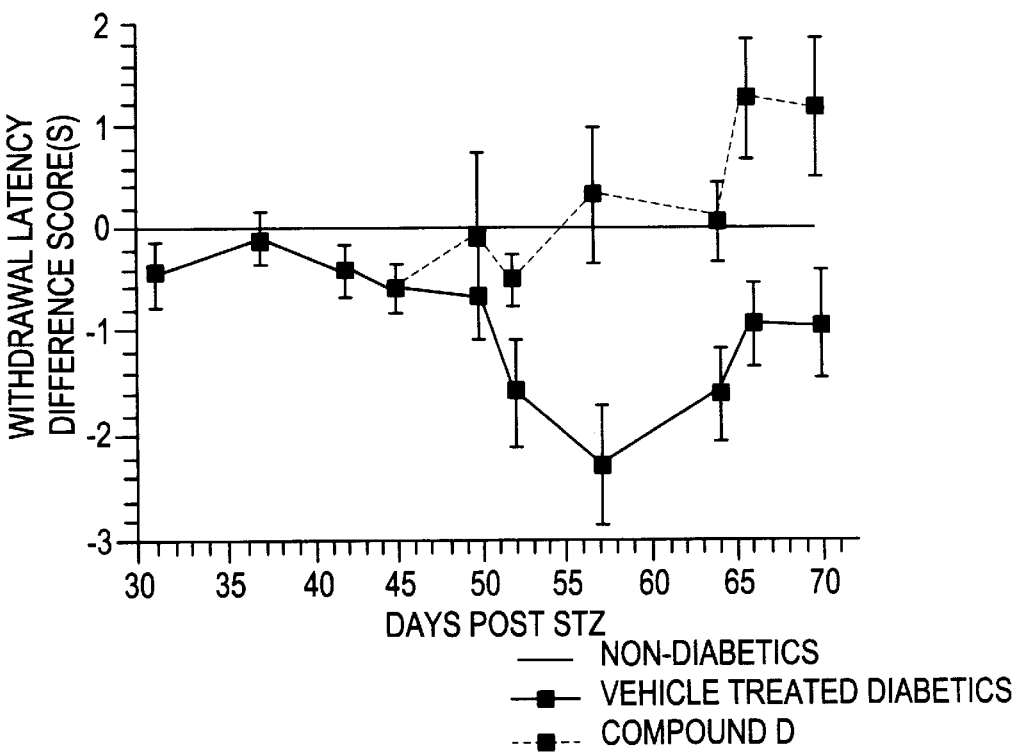
FIG. 7B is a bar graph plotting the withdrawal latency difference scores of non-diabetic rats and STZ-diabetic rats treated with a vehicle or 2-(2-sulfanylethyl)pentanedioic acid ("Compound D"), against the days following administration with STZ.

Male Sprague-Dawley rats (200–225 g) were rendered diabetic by intravenous administration of streptozotocin ("STZ", 70 mg/kg in phosphate buffered saline). Diabetic animals were divided into five groups: one group receiving Compound A (10 mg/kg or 1 mg/kg), Compound D (10 mg/kg or 1 mg/kg) or vehicle. Another group of animals (non-STZ treated) served as non-diabetic controls. Drug/vehicle treatment was started in diabetic animals 45 days post-STZ administration. STZ-induced diabetic rats were tested for sensitivity to a heat source as soon as blood glucose levels rose to 320 mg/dl or above (30 days post STZ). The rats were then acclimated to a Hargreaves apparatus and thermal nociception was monitored using an infrared heat source directed into the dorsal surface of the hindpaw, and the time taken for the animal to remove its paw noted to the nearest 0.1 seconds (see Hargreaves et al., supra, for detailed experimental method). The intensity of the beam source was adjusted such that the mean latency for control animals (non-STZ treated) was approximately 10 seconds. Each animal was tested 8 times and the mean difference score (between mean non-diabetic control latency and mean diabetic latency) are graphically presented in FIGS. 7A and 7B. Diabetic rats displayed a hyperalgesia (shorter response latency) compared to non-diabetic controls, starting 30 days post STZ treatment and progressively worsening in vehicle treated rats. This hyperalgesic response was completely reversed in diabetic rats receiving treatment with Compound D or A (10 mg/kg i.p. daily). Thus, the results show that NAALADase inhibition attenuates neuropathic pain.

Example 10

In Vivo Assay of NAALADase Inhibitors on Neuropathic Pain in CCI Model

Sciatic nerve ligation, consisting of 4 ligatures tied loosely around the sciatic nerve at 1 mm intervals proximal to the nerve trifurcation, was performed on rats. Following sciatic nerve ligation, the rats exhibited a thermal hyperalgesia and allodynia. The rats were habituated to a Hargreaves apparatus. An infrared heat source was directed onto the dorsal surface of each rat's hindpaws and the time taken for the rat to withdraw its paws was noted. The difference in scores between the latency of the response for the paw on the operated side versus the paw on the unoperated control side was determined.

Compound 49

Figure 13:
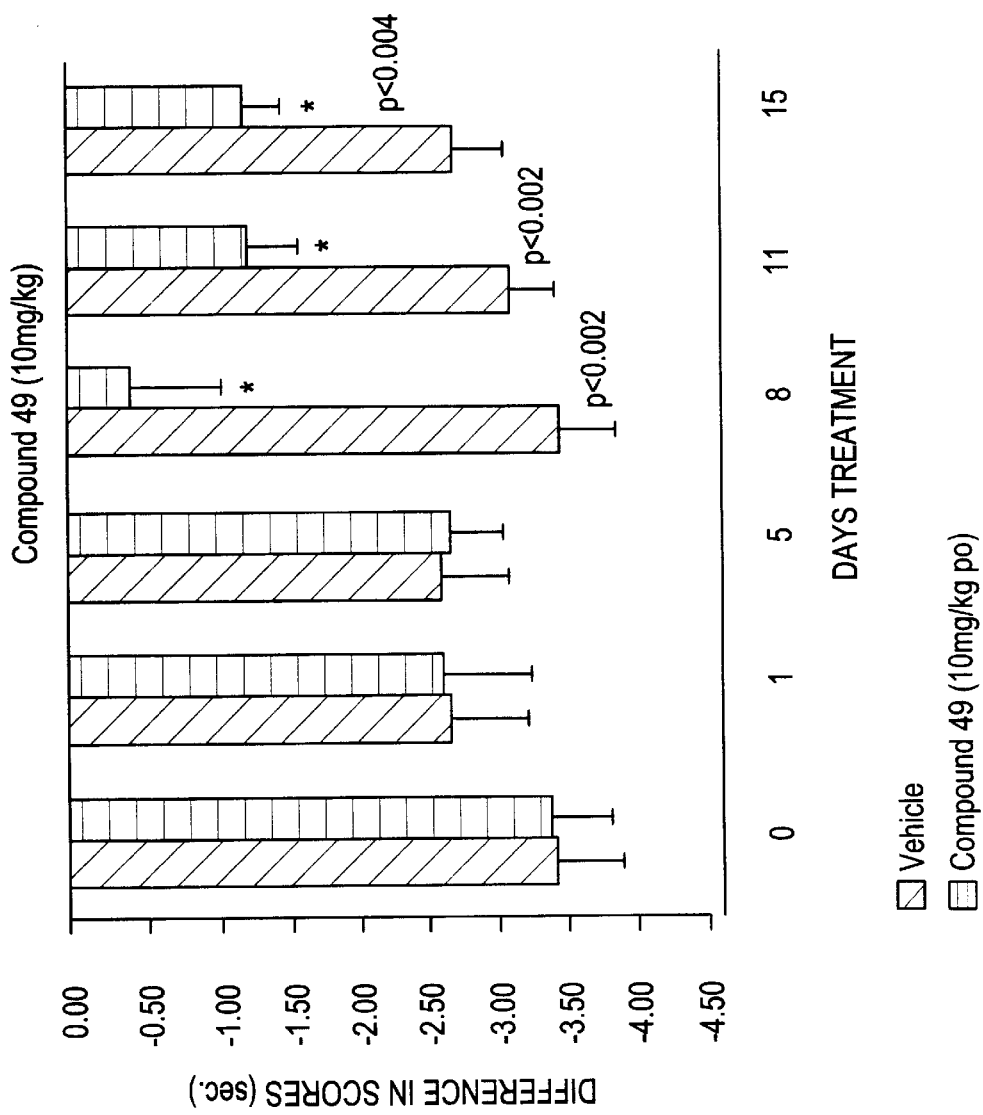
FIG. 13 is a bar graph plotting the withdrawal latency differences in scores of chronic constrictive injury-induced rats treated with a vehicle or 10 mg/kg 3-carboxy-5-(1,1-dimethylethyl)-alpha-(3-mercaptopropyl)-benzenepropanoic acid ("Compound 49"), against the days following treatment.
Figure 14:
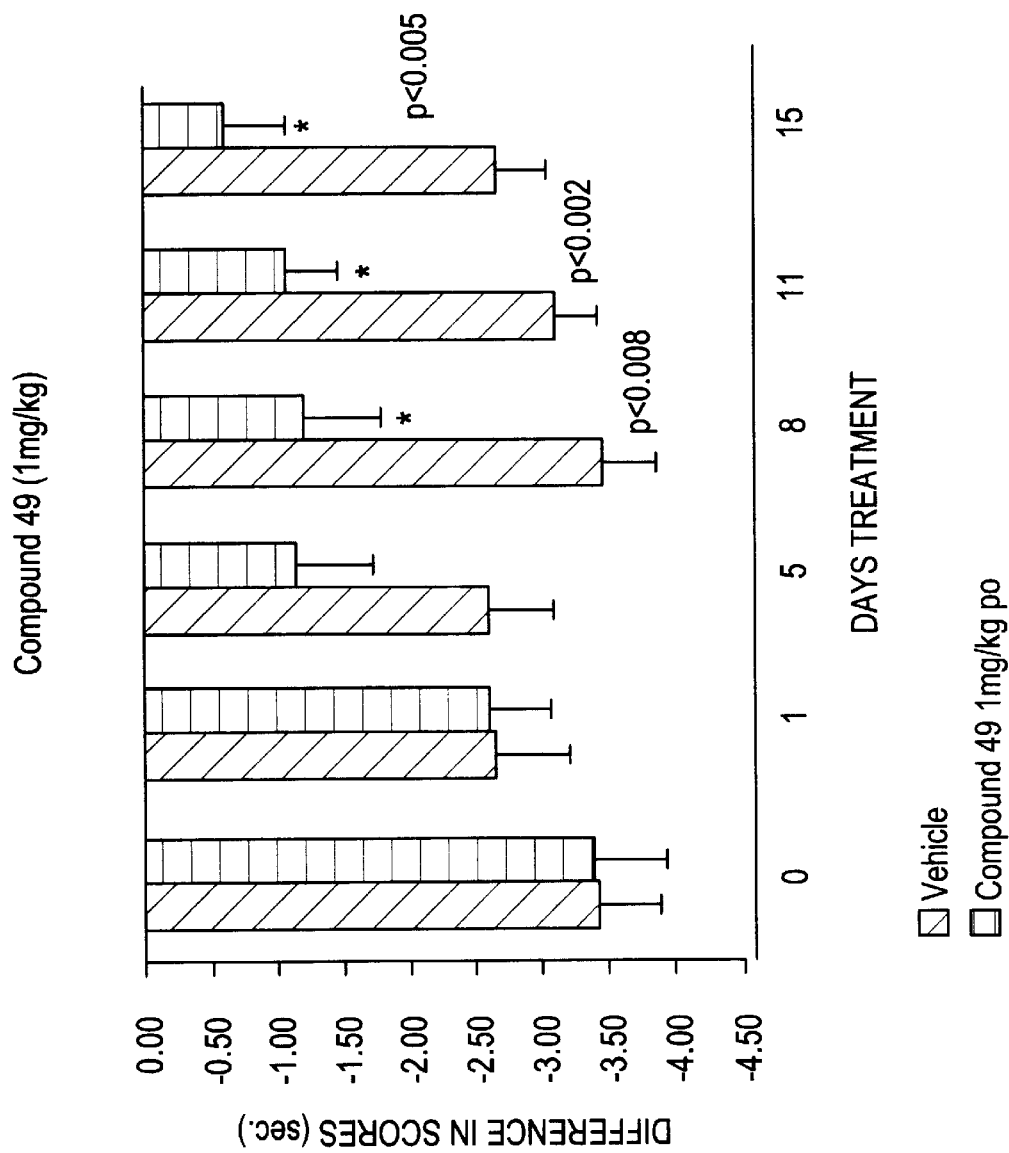
FIG. 14 is a bar graph plotting the withdrawal latency differences in scores of chronic constrictive injury-induced rats treated with a vehicle or 1 mg/kg Compound 49, against the days following treatment.
Figure 15:
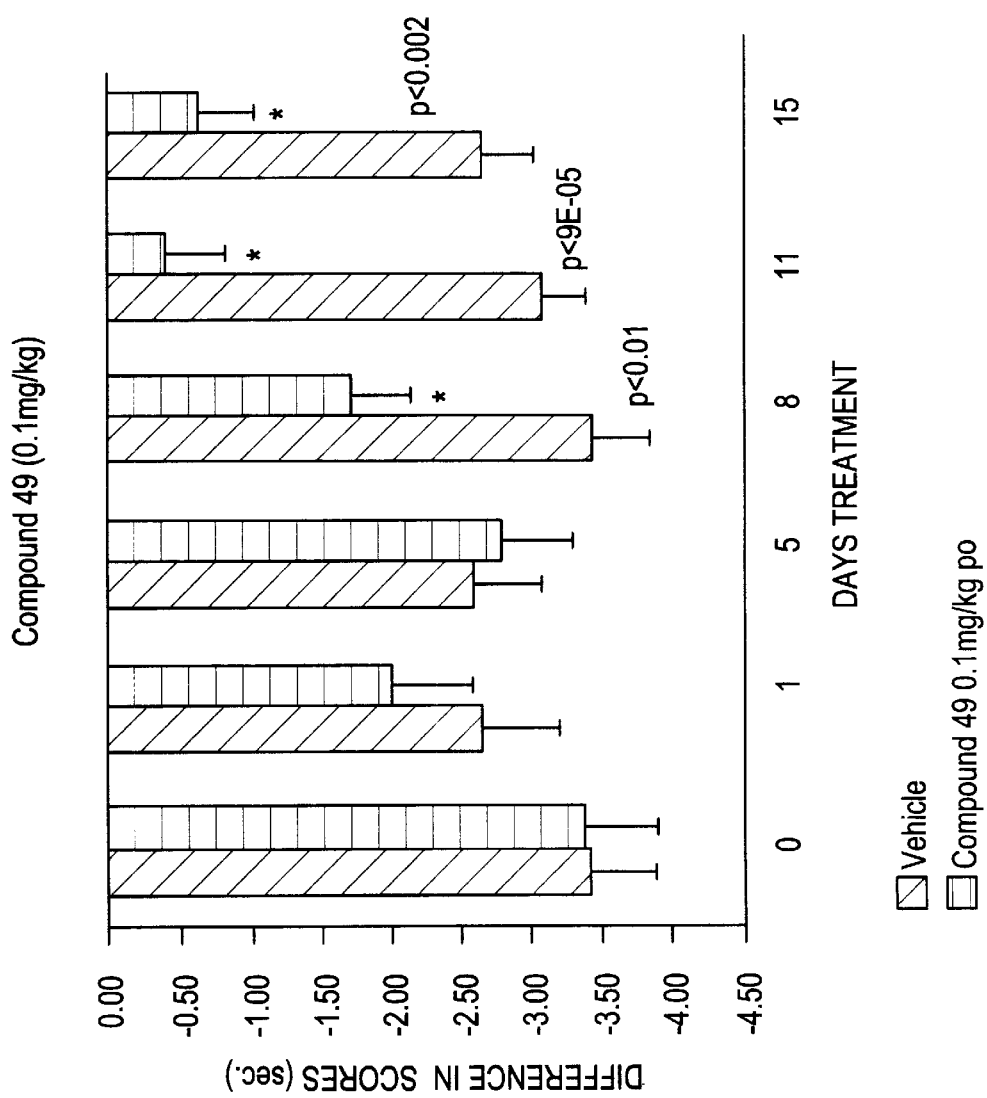
FIG. 15 is a bar graph plotting the withdrawal latency differences in scores of chronic constrictive injury-induced rats treated with a vehicle or 0.1 mg/kg Compound 49, against the days following treatment.
Figure 16:
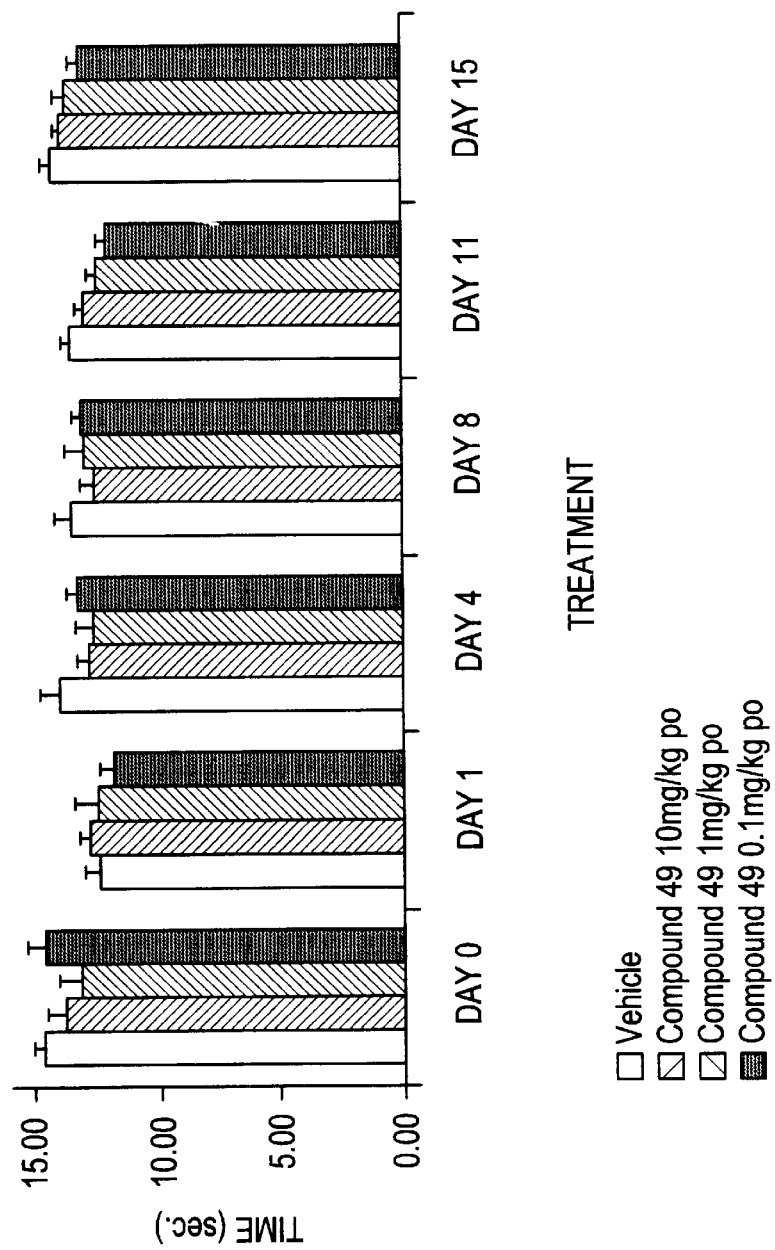
FIG. 16 is a bar graph plotting the withdrawal latency of chronic constrictive injury-induced rats treated with a vehicle or 10, 1 or 0.1 mg/kg Compound 49, against the days following treatment.
Figure 17:
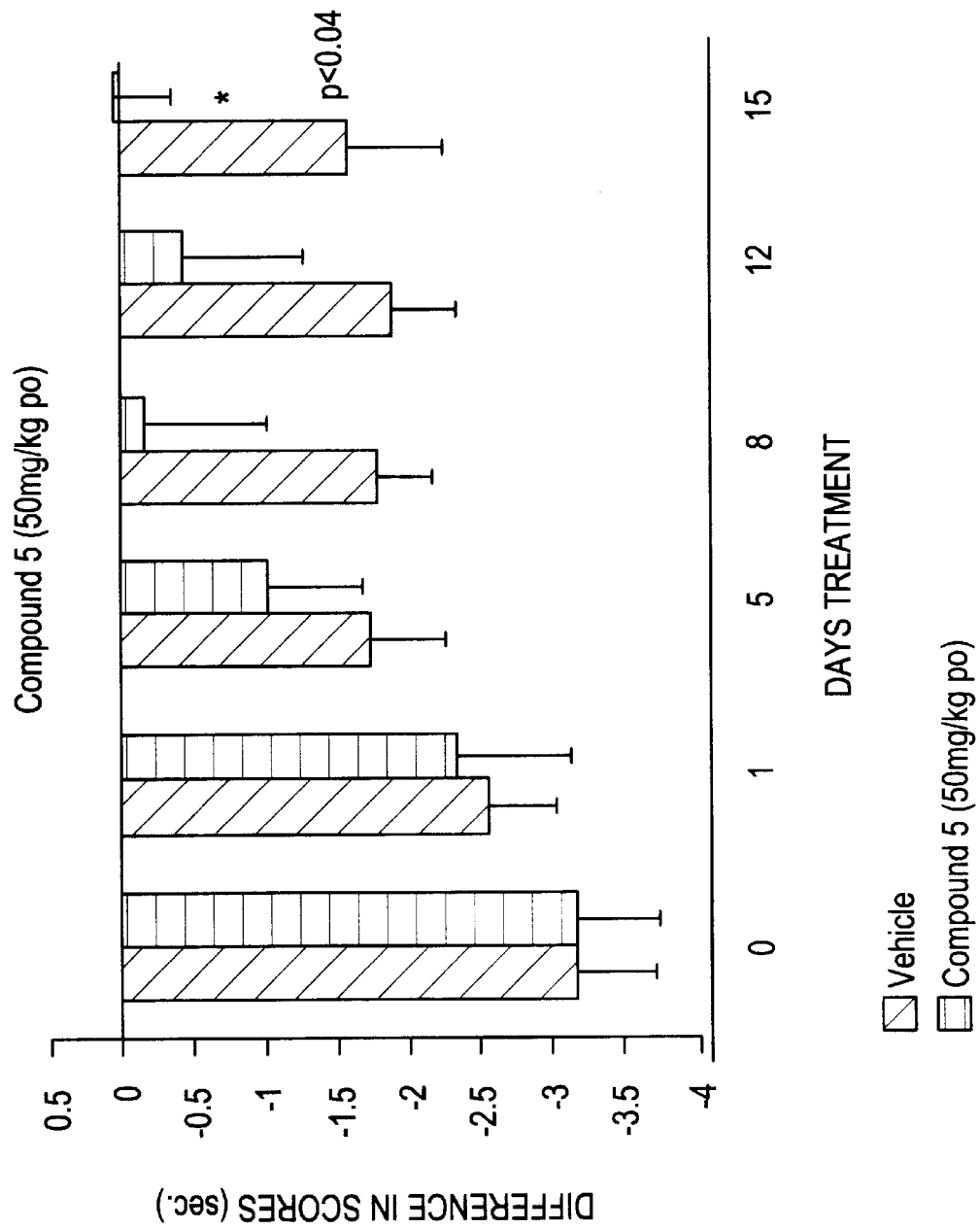
FIG. 17 is a bar graph plotting the withdrawal latency differences in scores of chronic constrictive injury-induced rats treated with a vehicle or 50 mg/kg 3-carboxy-alpha-(3-mercaptopropyl)-benzenepropanoic acid ("Compound 5"), against the days following treatment.
Figure 18:
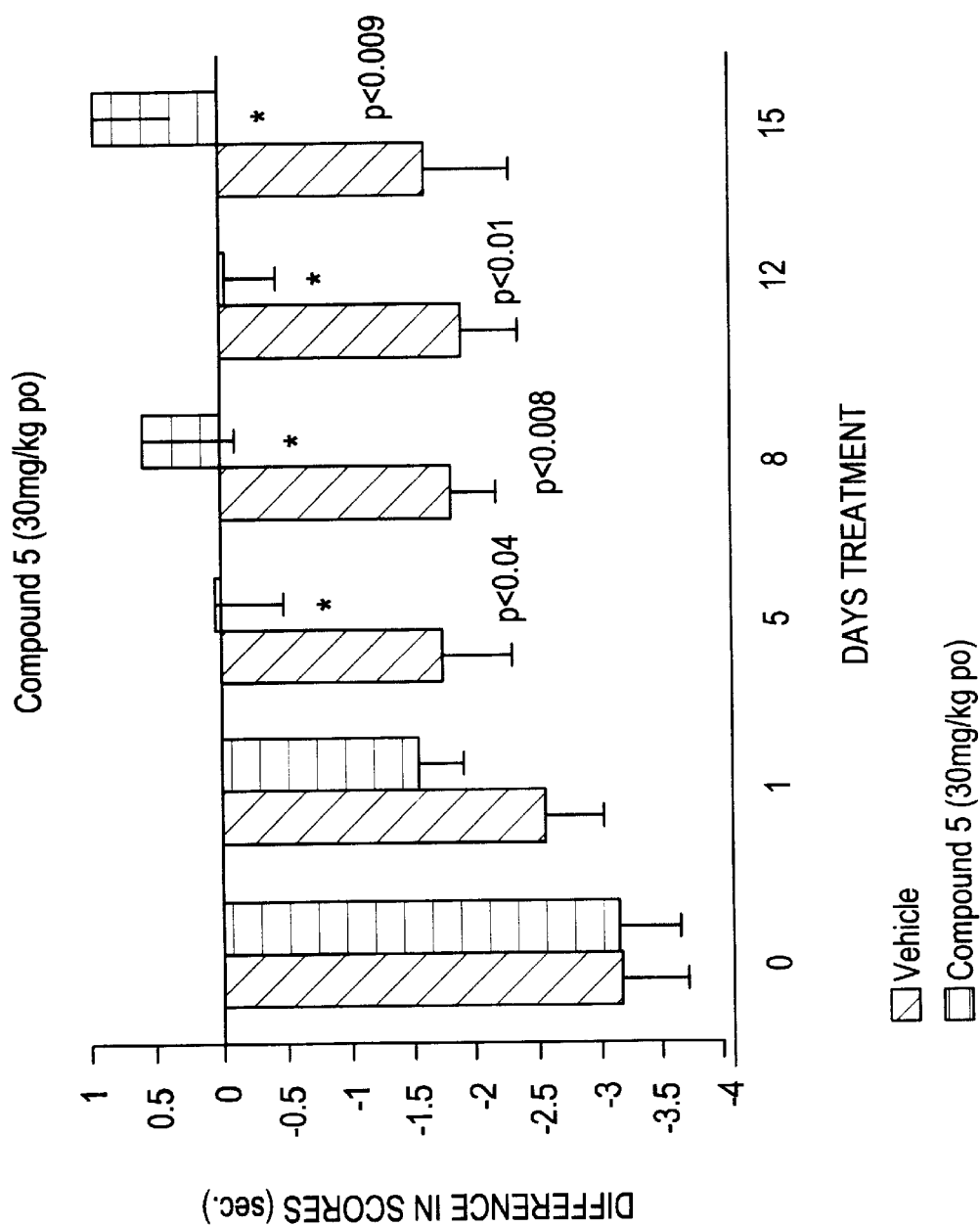
FIG. 18 is a bar graph plotting the withdrawal latency differences in scores of chronic constrictive injury-induced rats treated with a vehicle or 30 mg/kg Compound 5, against the days following treatment.
Figure 19:
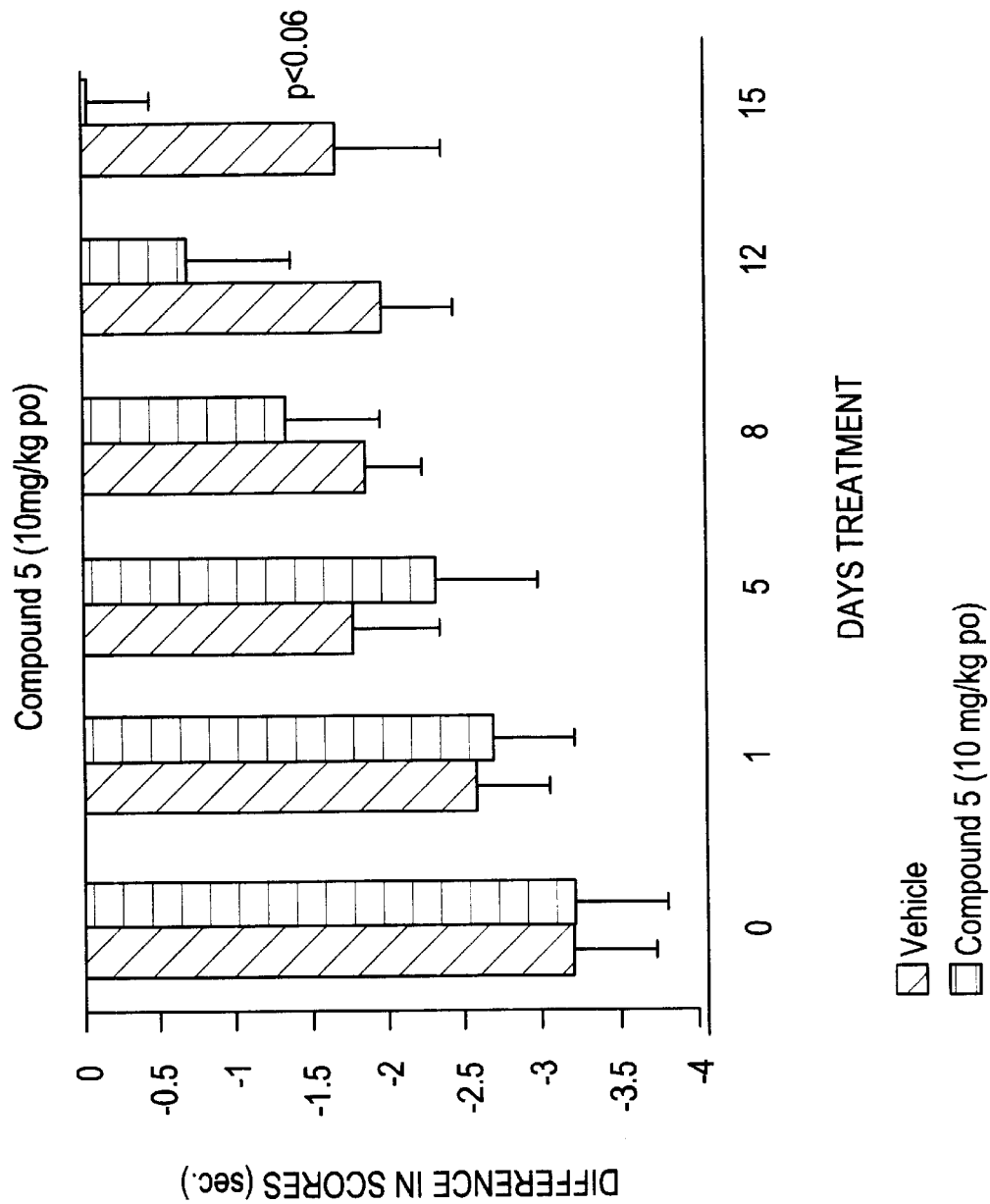
FIG. 19 is a bar graph plotting the withdrawal latency differences in scores of chronic constrictive injury-induced rats treated with a vehicle or 10 mg/kg Compound 5, against the days following treatment.
Figure 20:
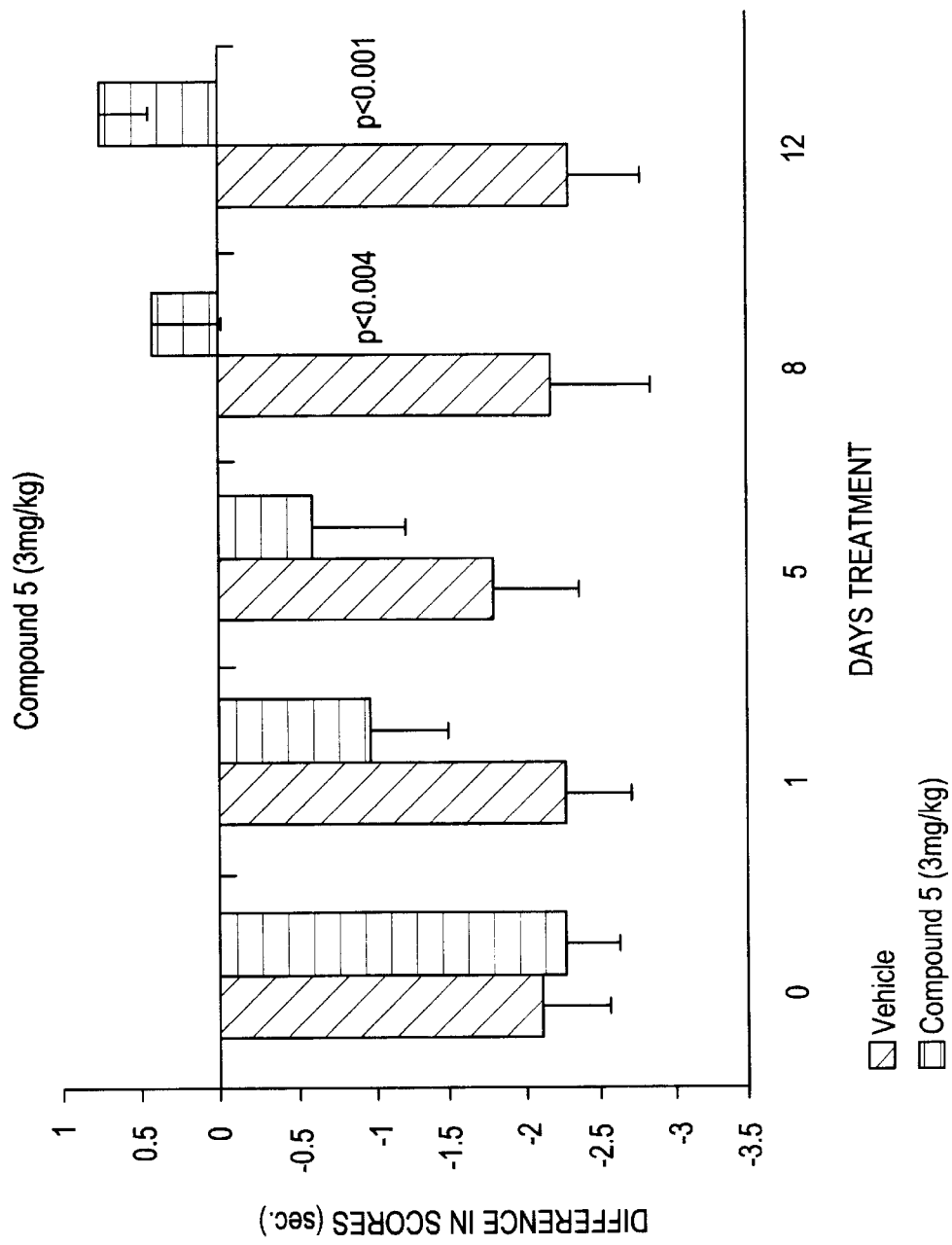
FIG. 20 is a bar graph plotting the withdrawal latency differences in scores of chronic constrictive injury-induced rats treated with a vehicle or 3 mg/kg Compound 5, against the days following treatment.
Figure 21:
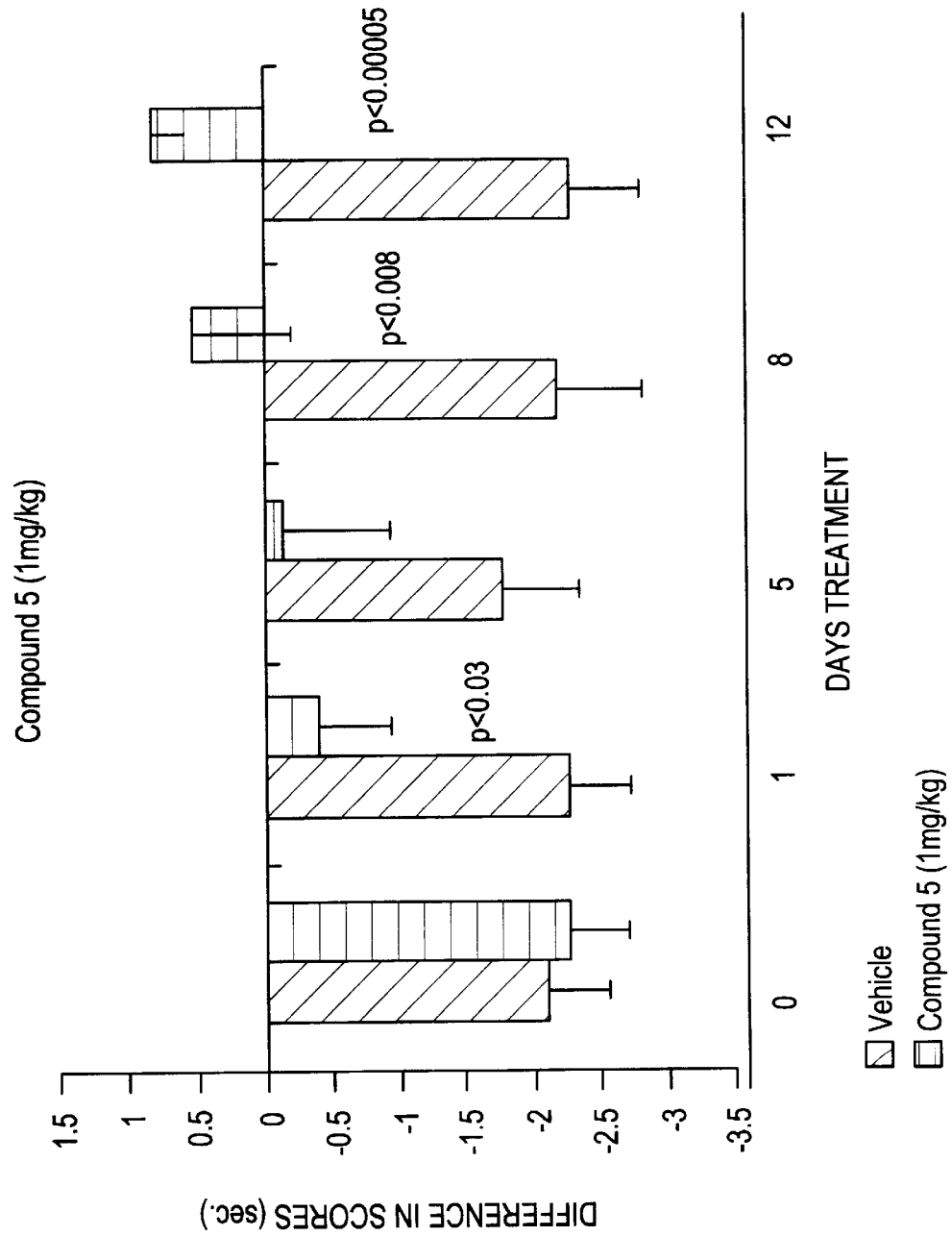
FIG. 21 is a bar graph plotting the withdrawal latency differences in scores of chronic constrictive injury-induced rats treated with a vehicle or 1 mg/kg Compound 5, against the days following treatment.
Figure 22:
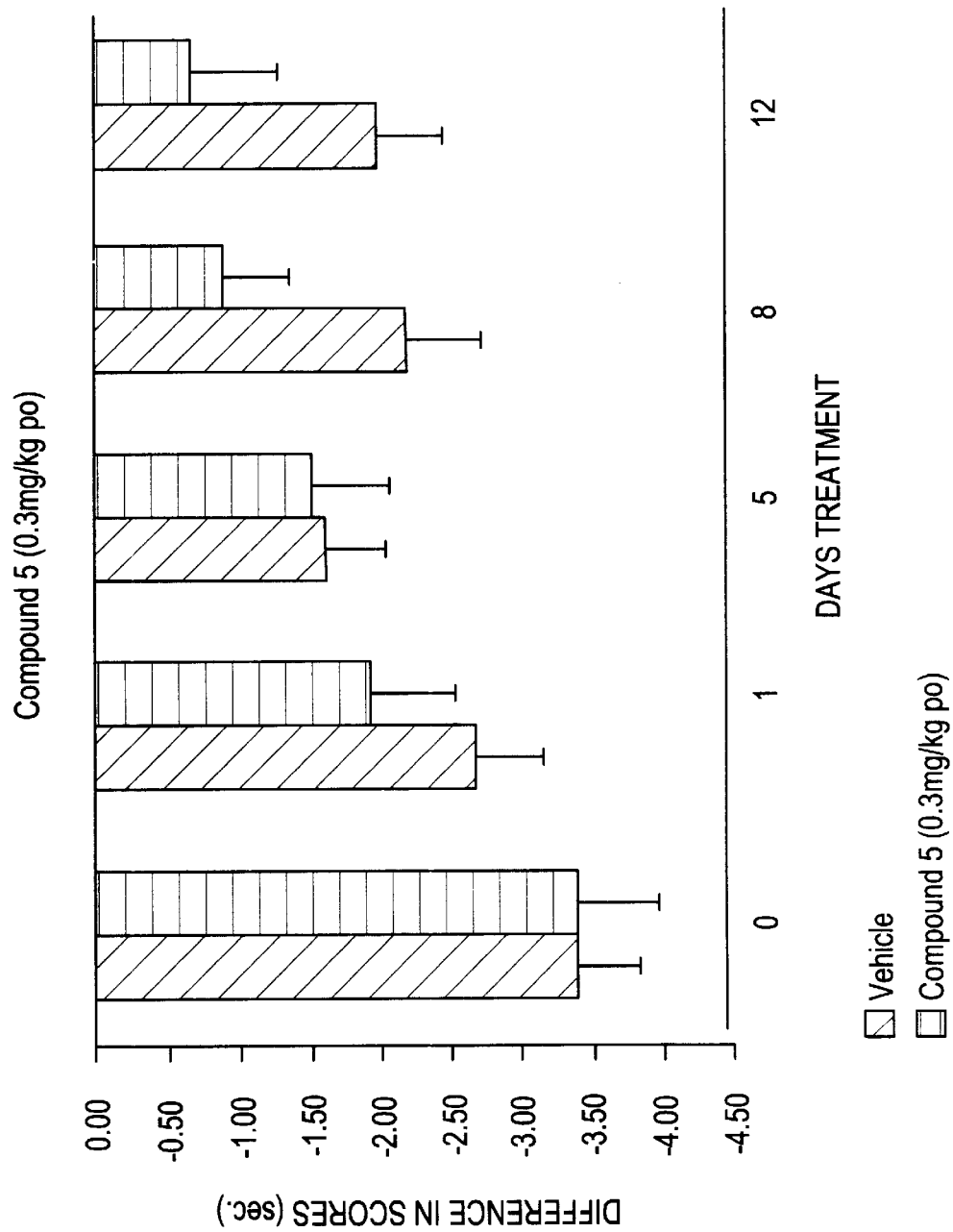
FIG. 22 is a bar graph plotting the withdrawal latency differences in scores, of chronic constrictive injury-induced rats treated with a vehicle or 0.3 mg/kg Compound 5, against the days following treatment.

The rats were treated with either Compound 49 (10, 1 or 0.1 mg/kg) or a vehicle for 15 days after sciatic nerve ligation. Thermal pain responses were measured at days 0, 1, 5, 8, 11 and 15. The differences in scores for the rats treated with a vehicle and the rats treated with Compound 49 are graphically presented in FIGS. 13–15. The results show that treatment with Compound 49 normalized the difference in scores between the operated and unoperated paws compared to the continued hyperalgesic vehicle-treated rats. The time taken for the rats to withdraw its paw on the unoperated (sham) side are graphically presented in FIG. 16. The rats exhibited approximately equal withdrawal latencies on the sham side regardless of treatment.

Compound 5

Figure 23:
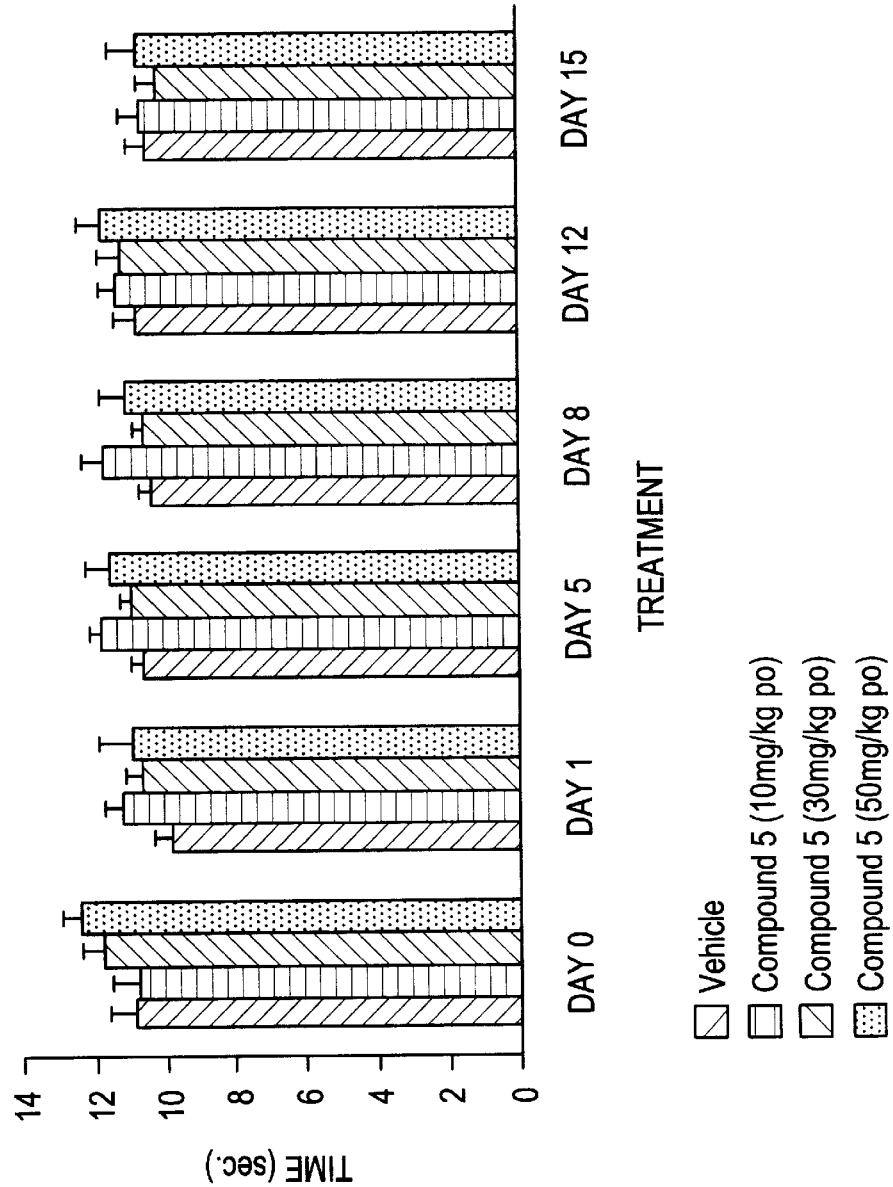
FIG. 23 is a bar graph plotting the withdrawal latency of chronic constrictive injury-induced rats treated with a vehicle or 10, 30 or 50 mg/kg Compound 5, against the days following treatment.
Figure 24:
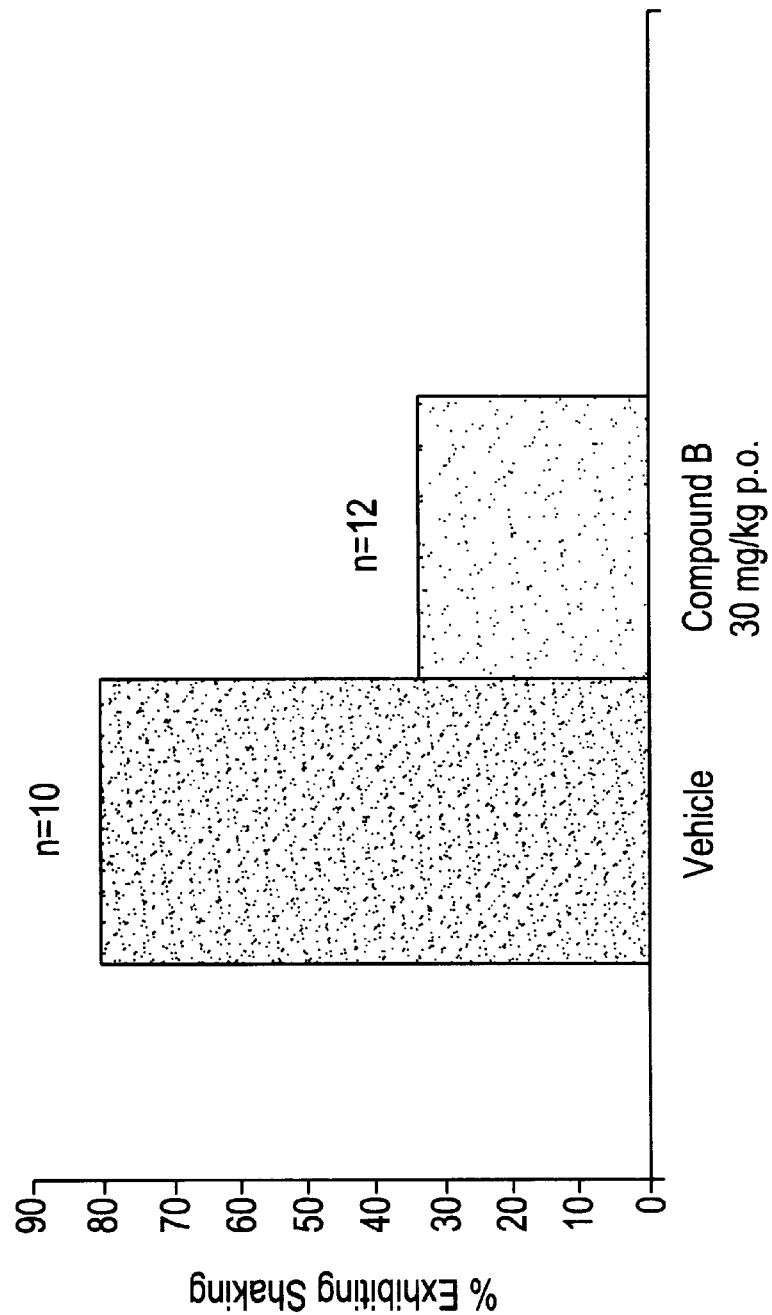
FIG. 24 is a bar graph plotting the percent of transgenic mice at 210 days of age that exhibited limb shaking after treatment with 2-(3-sulfanylpropyl)pentanedioic acid ("Compound B") or a vehicle.
Figure 25:
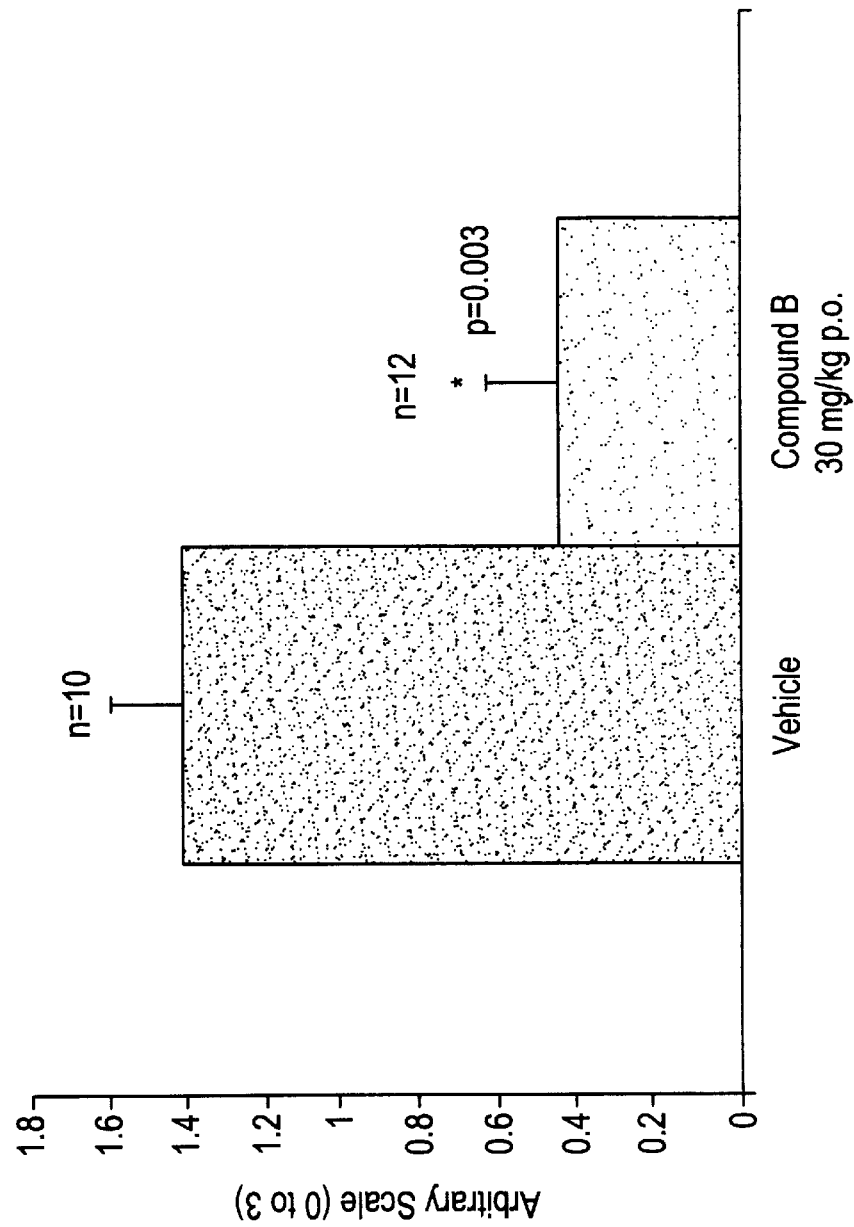
FIG. 25 is a bar graph plotting the gait, measured on an arbitrary scale ranging from 0 to 3, of transgenic mice at 210 days of age after treatment with Compound B or a vehicle.
Figure 26:
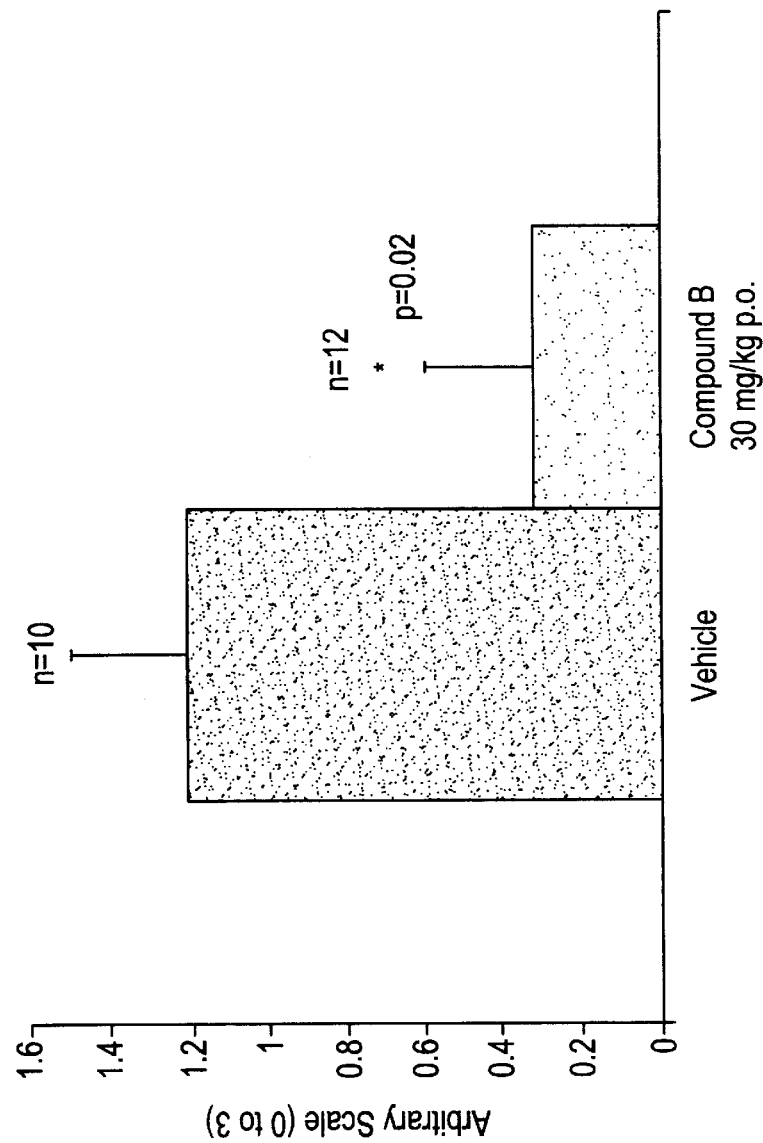
FIG. 26 is a bar graph plotting hind limbs dragging, measured on an arbitrary scale ranging from 0 to 3, of transgenic mice at 210 days of age after treatment with Compound B or a vehicle.
Figure 27:
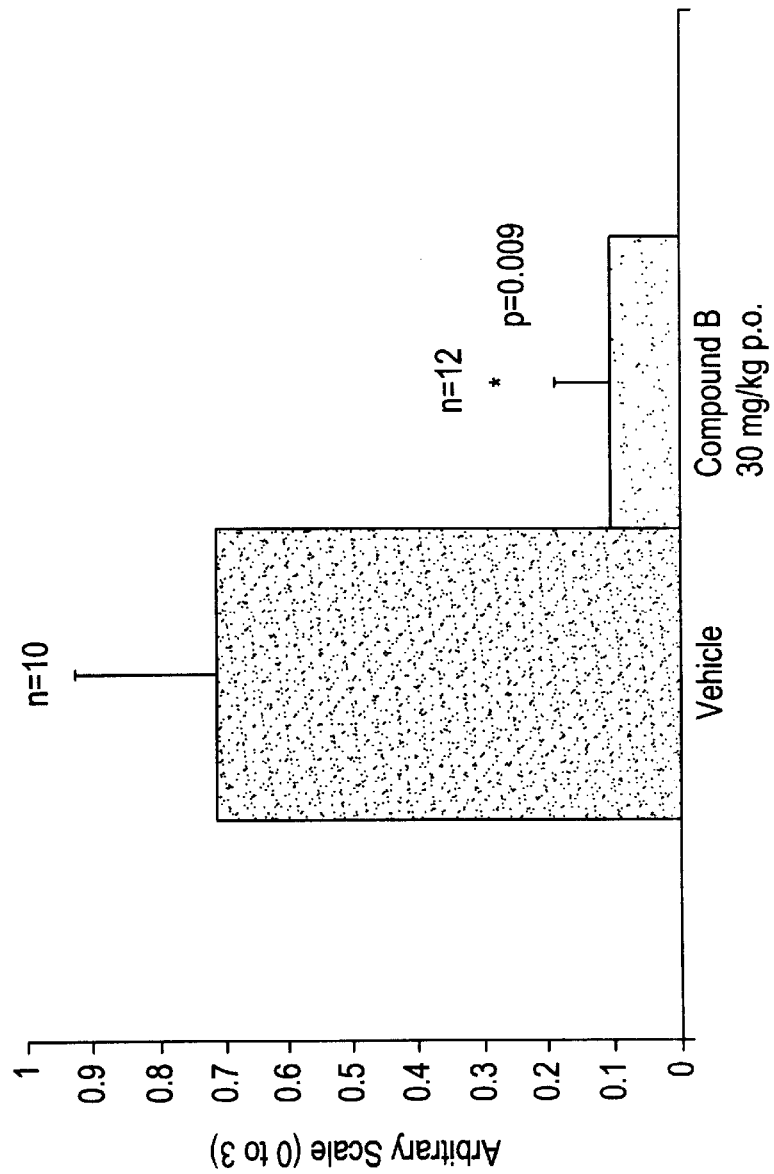
FIG. 27 is a bar graph plotting the crossing of limbs, measured on an arbitrary scale ranging from 0 to 3, of transgenic mice at 210 days of age after treatment with Compound B or a vehicle.
Figure 28:
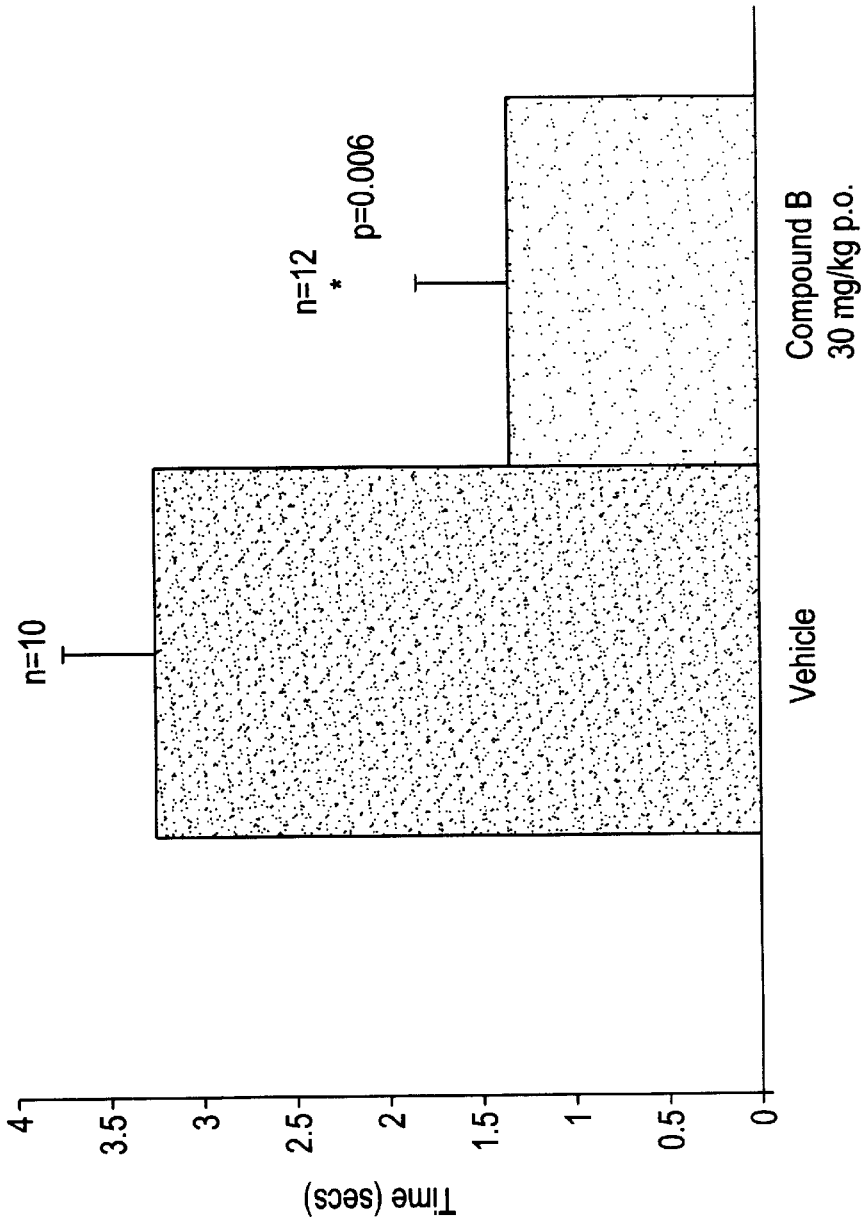
FIG. 28 is a bar graph plotting the righting reflex of transgenic mice, measured by the time (seconds) it took the mice to right themselves when placed on their sides, at 210 days of age after treatment with Compound B or a vehicle.
Figure 29:
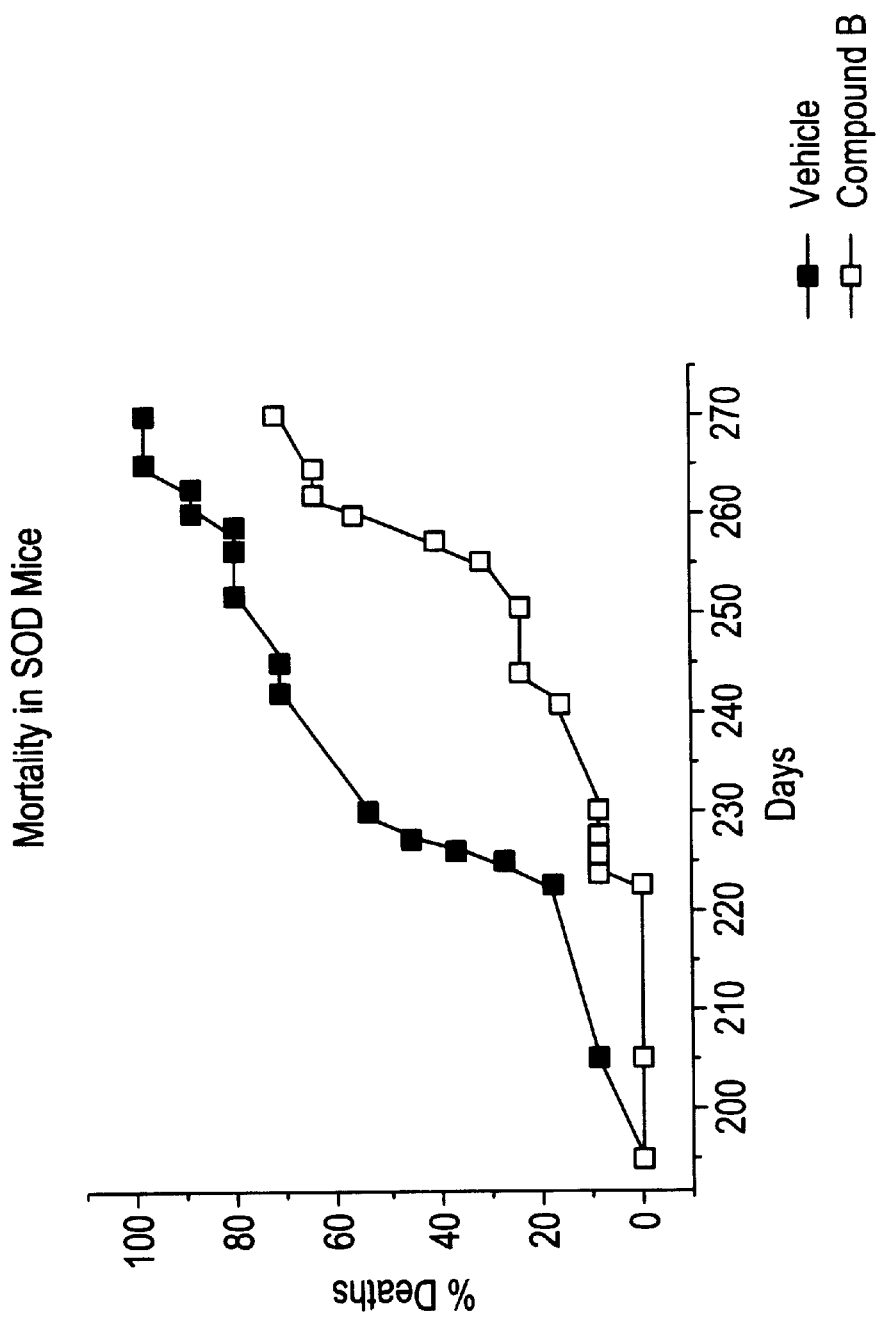
FIG. 29 is a graph plotting the percent of transgenic mice treated with Compound B or a vehicle that died against the age of the mice (days).
Figure 30:
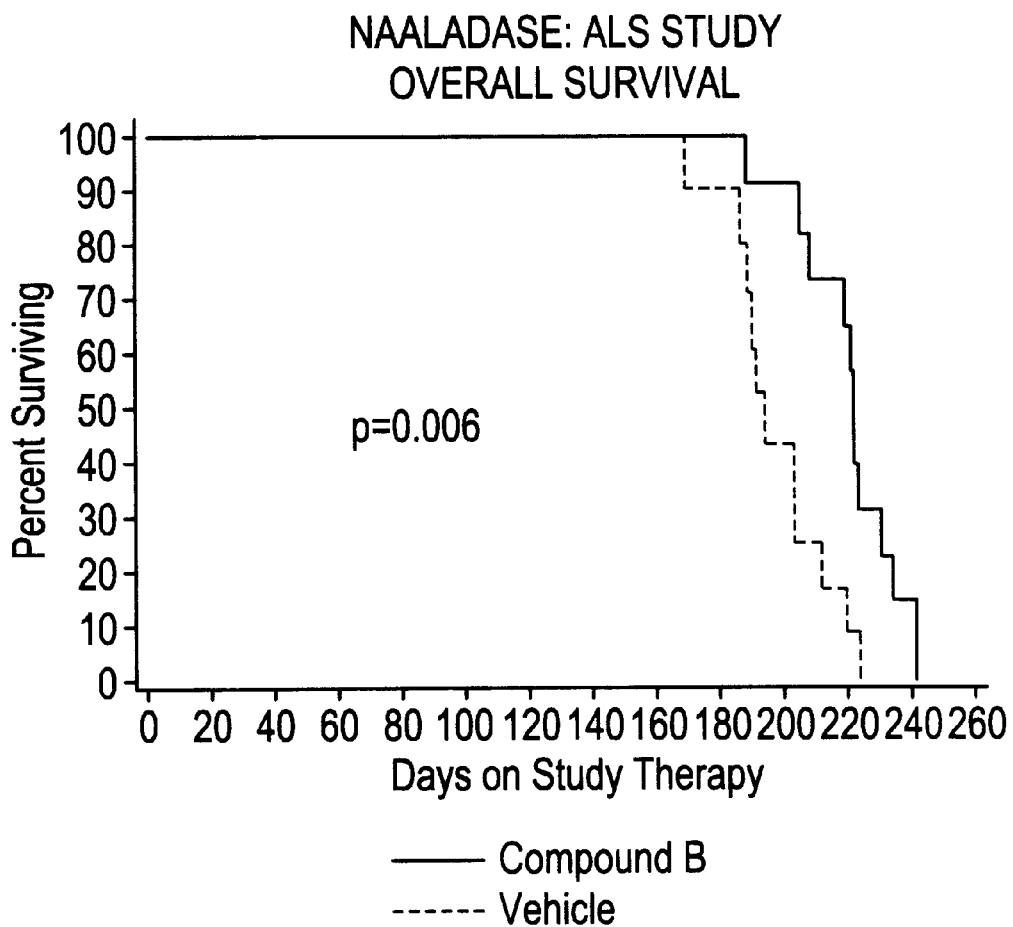
FIG. 30 is a Kaplan-Meier survival graph plotting the percent of transgenic mice treated with Compound B or a vehicle that survived against the number of days that the mice were on study therapy.

The rats were treated with either Compound 5 (50, 30, 10, 3, 1 or 0.3 mg/kg) or a vehicle for 12 (or 15) days after sciatic nerve ligation. Thermal pain responses were measured at days 0, 1, 5, 8 and 12 (and 15). The differences in scores for the rats treated with a vehicle and the rats treated with Compound 5 are graphically presented in FIGS. 17–22. The results show that treatment with Compound 5 normalized the difference in scores between the operated and unoperated paws compared to the continued hyperalgesic vehicle-treated rats. The time taken for the rats to withdraw its paw on the unoperated (sham) side are graphically presented in FIG. 23. The rats exhibited approximately equal withdrawal latencies on the sham side regardless of treatment.

Compound C

Figure 8:
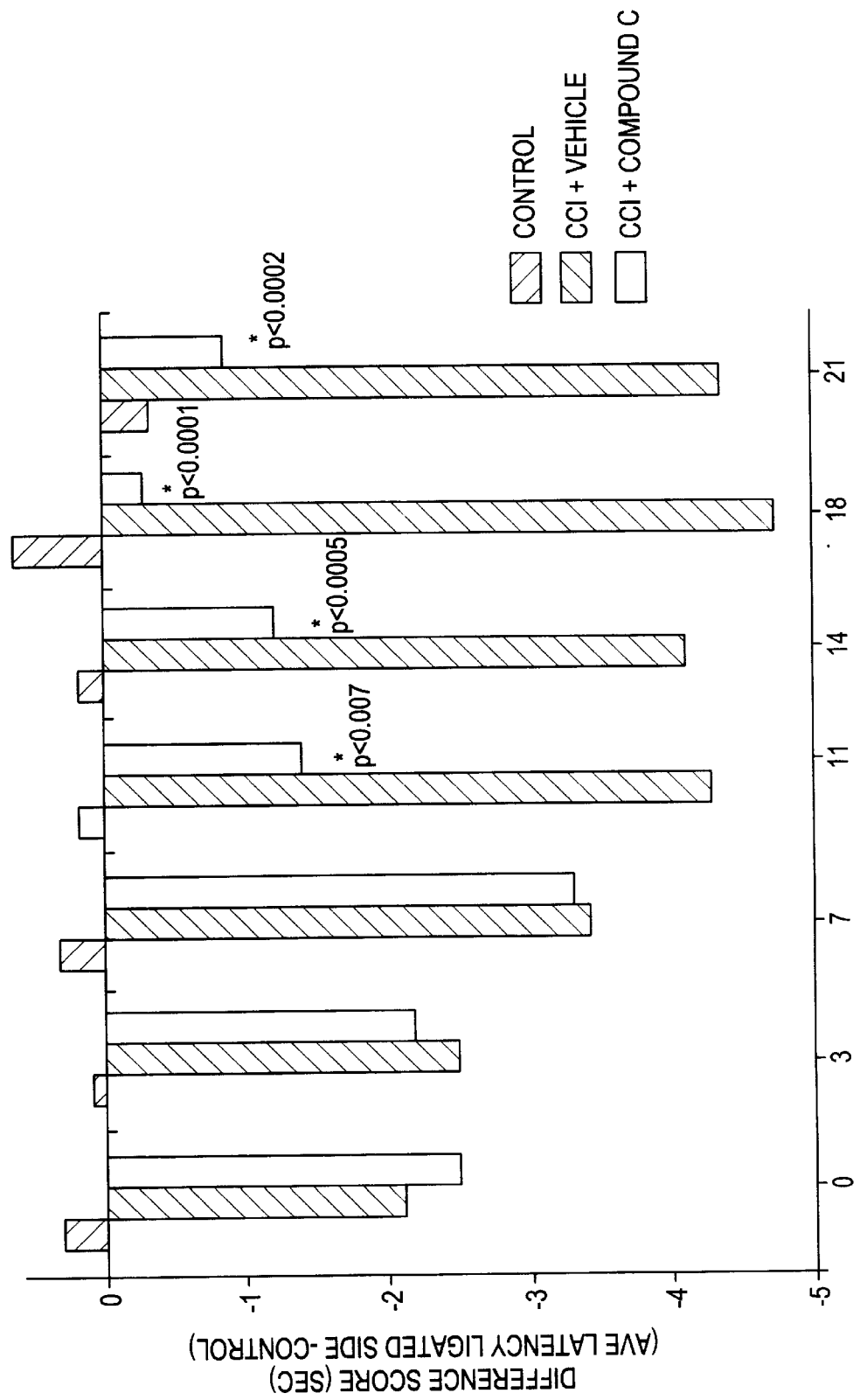
FIG. 8 is a bar graph plotting the withdrawal latency difference scores of normal (unoperated) rats and chronic constrictive injury-induced rats treated with a vehicle or Compound C, against the days following surgery.

The rats received either Compound C (50 mg/kg i.p. daily) or a vehicle starting 10 days post surgery. Treatment with Compound C dramatically normalized the difference scores between the two paws compared to the continued hyperalgesic vehicle-treated controls. Normal (unoperated) rats: had approximately equal latencies for both paws. This effect was significant starting at 11 days of drug treatment and persisted through to the end of the study (for 21 days of daily dosing). The difference scores are graphically presented in FIG. 8. The results show that NAALADase inhibition attenuates CCI-associated hyperalgesia.

Example 11

In Vivo Assay of NAALADase Inhibitors on Progression of Neuropathic Pain in BB/W Models Compounds D and A Male BB/W rats (BRI, Mass) spontaneously develop a cell mediated autoimmune destruction of pancreatic B cells, resulting in onset of insulin-dependent (Type I) diabetes (Guberski 1994). These rats have been characterized and shown to demonstrate neuropathies with accompanying neural deficits such as fiber loss and degeneration, changes which are correlative with those seen in peripheral nerve of human diabetic patients (Yagihasi 1997). This renders them valuable for experimental trials of new compounds for future treatments of this major disorder. In the present study, Compound D and Compound A were examined for their ability to alter the progression of diabetic neuropathy. The rats received daily injection of Compound D or Compound A (10 mg/kg i.p.) or vehicle, starting at the onset of diabetes (hyperglycemia) and up to 6 months thereafter. Another group of non-diabetic rats also receiving vehicle were tested. All animals were continuously monitored for body weight, urine volume, blood sugar and glycated haemoglobin. In the first month of the study, all animals were tested for thermal nociception in a Hargreaves apparatus, weekly. After the first month this was done biweekly and then monthly. The testing consists of directing an infrared heat source onto the dorsal surface of the rat hindpaw and noting the time taken for the animal to remove its paw (see Hargreaves et al., supra, for a description of the experimental method). Each animal was tested 8 times and the mean withdrawal latency noted.

Figure 11:
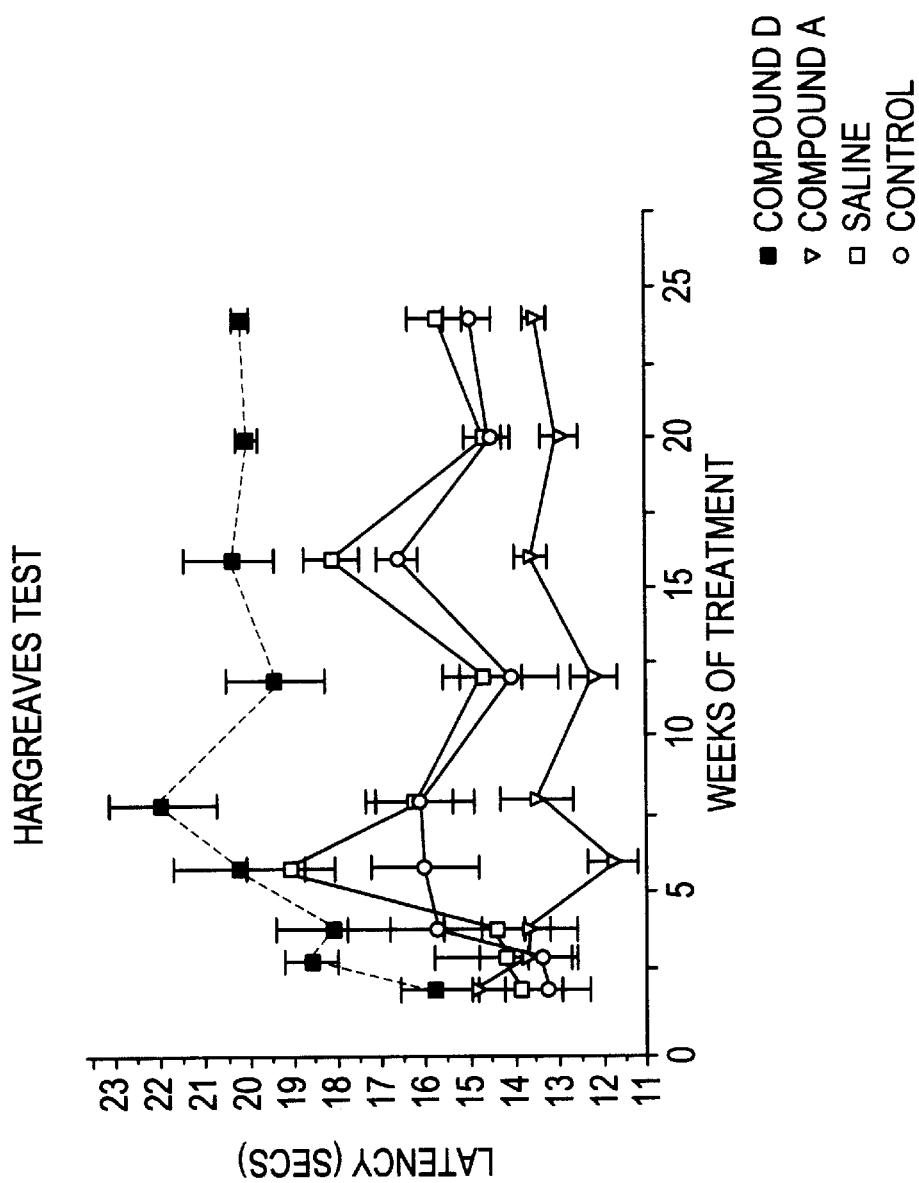
FIG. 11 is a graph plotting the withdrawal latency of non-diabetic rats and BB/W diabetic rats treated with a vehicle, Compound D or Compound A, against the weeks of treatment.

The results are graphically presented in FIG. 11. The results show that diabetic rats displayed a hyperalgesia (shorter response latency) compared to non-diabetic controls. Diabetic drug-treated rats (both Compound D and Compound A) displayed longer withdrawal latencies than diabetic vehicle-treated rats, starting after 4 weeks of treatment and persisting through the six months of treatment.

Figure 12:
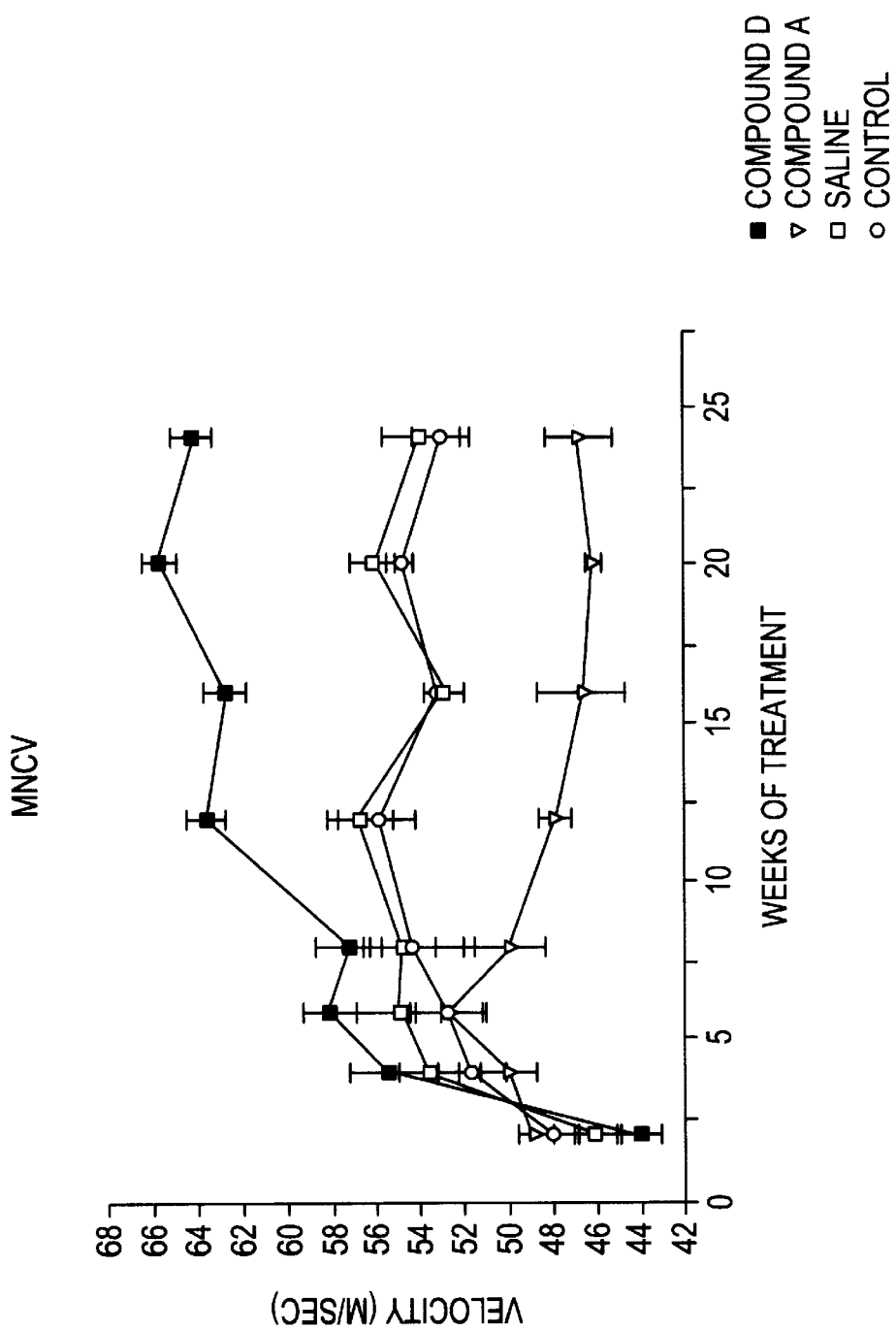
FIG. 12 is a graph plotting the nerve conduction velocity of non-diabetic rats and BB/W diabetic rats treated with a vehicle, Compound D or Compound A, against the weeks of treatment.

Nerve conduction velocity was also measured every two weeks through the first eight weeks of treatment and every month thereafter through to the six months of treatment (see De Koning et al., Peptides, Vol. 8, No. 3, pp. 415–22 (1987) for a description of the experimental method). The results are graphically presented in FIG. 12. Diabetic animals generally showed a reduction in nerve conduction velocity compared to non-diabetic controls. However, diabetic animals receiving daily injections of NAALADase inhibitor (either Compound D or Compound A at a dose of 10 mg/kg) showed significantly less severe nerve conduction deficits than did the diabetic controls receiving vehicle treatment. This was apparent starting at 8 weeks of treatment and persisted to a similar degree through to the six month termination point of the study. Diabetic vehicles, on the other hand, showed a progressive deterioration in nerve conduction velocity from 6 to 16 weeks after start of vehicle administration which was maintained through to six months.

Example 12

In Vivo Assay of NAALADase Inhibitors on Diabetic Neuropathy in STZ Model

Figure 9A:
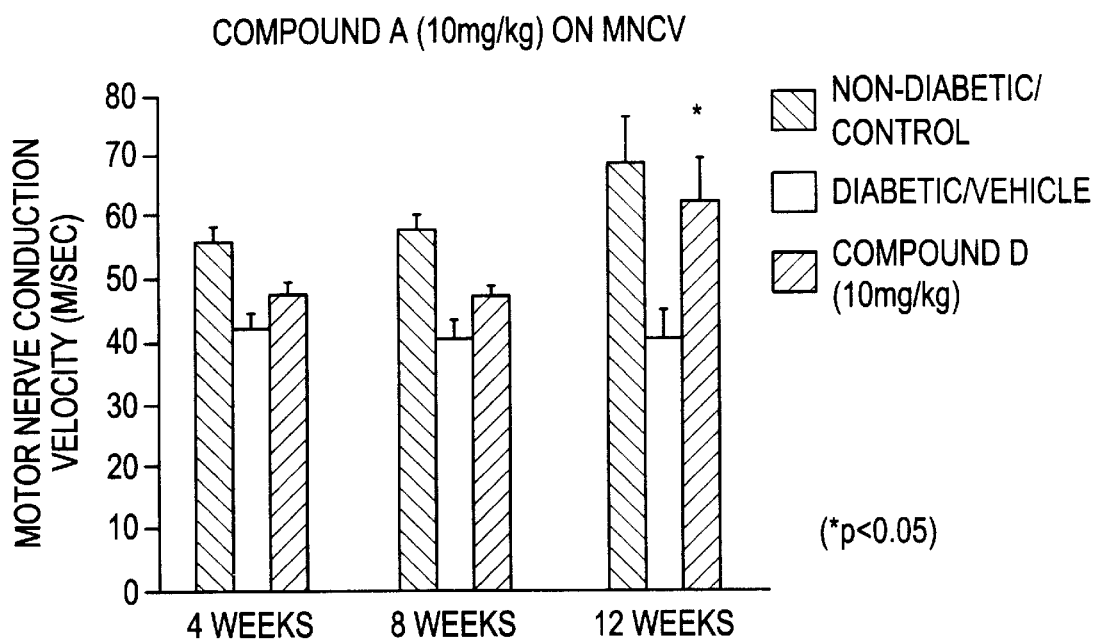
FIG. 9A is a bar graph plotting the motor nerve conduction velocity of non-diabetic rats and STZ-diabetic rats treated with a vehicle or Compound A, against the weeks post STZ.
Figure 9B:
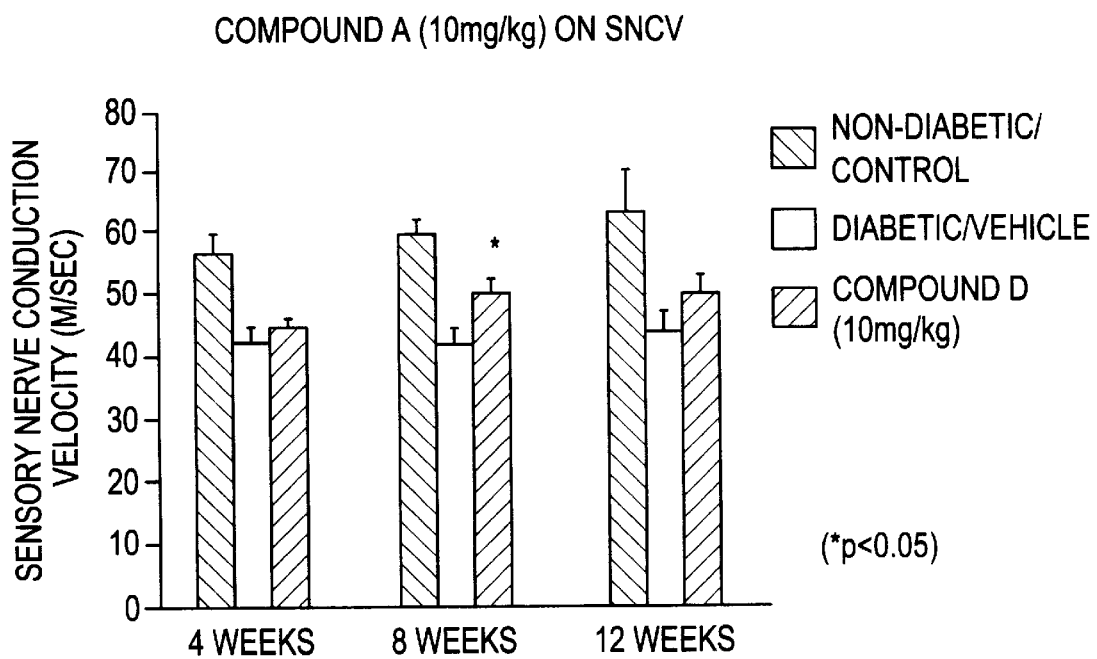
FIG. 9B is a bar graph plotting the sensory nerve conduction velocity of non-diabetic rats and STZ-diabetic rats treated with a vehicle or Compound A, against the weeks post STZ.
Figure 10A:
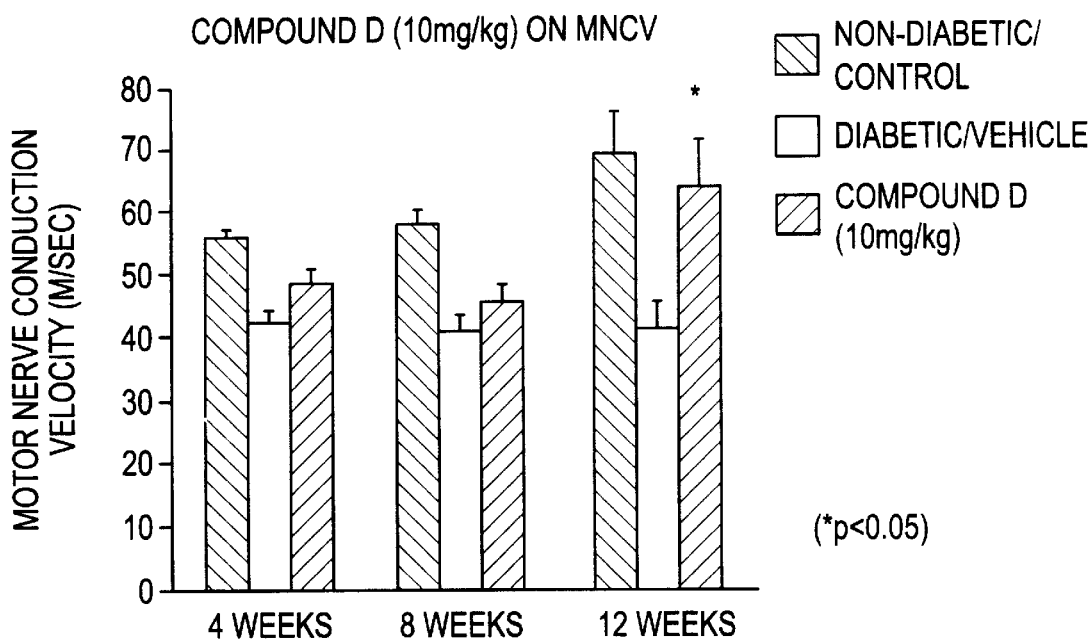
FIG. 10A is a bar graph plotting the motor nerve conduction velocity of non-diabetic rats and STZ-diabetic rats treated with a vehicle or Compound D, against the weeks post STZ.
Figure 10B:
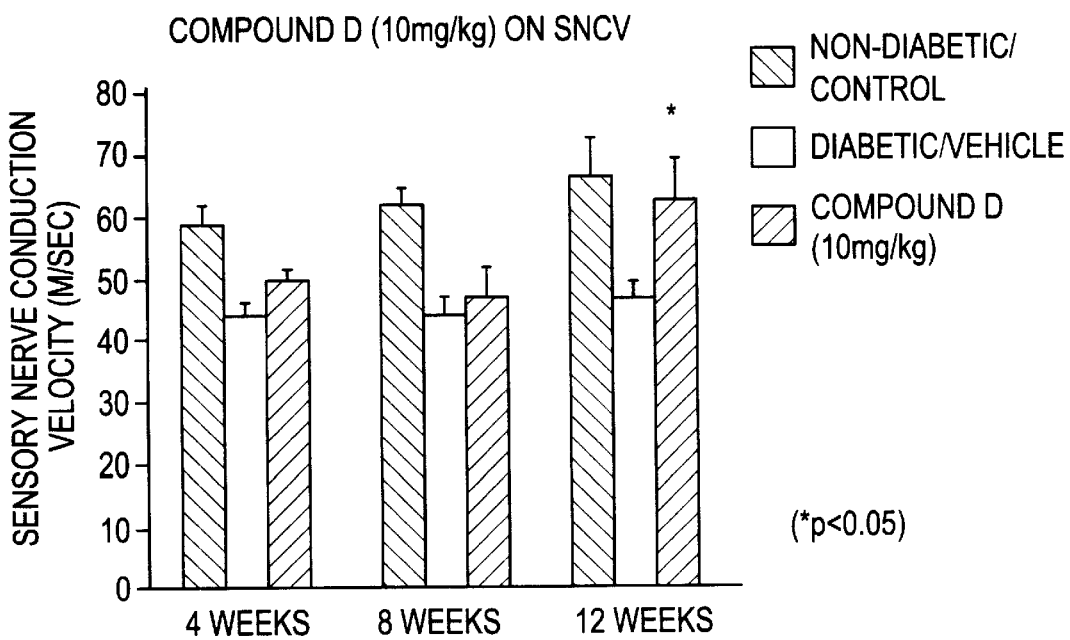
FIG. 10B is a bar graph plotting the sensory nerve conduction velocity of non-diabetic rats and STZ-diabetic rats treated with a vehicle or Compound D, against the weeks post STZ.

Motor and sensory nerve conduction velocity was also measured in STZ-diabetic animals after 4, 8 and 12 weeks of treatment (see De Koning et al., supra, for a description of the experimental method). Briefly, stimulating needle electrodes were inserted close to the sciatic and tibial nerves with recording electrodes being placed subcutaneously over the distal foot muscles, in anesthetized rats. The results are graphically presented in FIGS. 9A, 9B, 10A and 10B. Diabetic animals receiving vehicle showed a significant reduction in both motor and sensory nerve conduction compared to non-diabetic animals. Treatment with 10 mg/kg of Compound A daily for 4, 8 and 12 weeks all tended to improve (increase) both motor and sensory nerve conduction velocities, with a significant improvement being observed after 12 weeks and 8 weeks for motor and sensory nerve conduction velocity, respectively (FIGS. 9A and 9B). The lower dose of Compound A tested (1 mg/kg) had similar effects. Treatment of animals with Compound D at either dose also increased both motor and sensory nerve conduction velocities above that of diabetic controls, significantly so after 12 weeks of treatment for the 10 mg/kg treatment group (FIGS. 10A and 10B) and at the earlier time periods after treatment with the 1 mg/kg dose. Thus, the results show that NAALADase inhibition alters the progression of diabetic neuropathy.

Example 13

In Vivo Assay of NAALADase Inhibitors on Reversal of Diabetic Neuropathy in STZ Models General Method for STZ Model—Delayed Dosing Rats (200 to 225 g) were injected with STZ (70 mg/kg) into the tail vein. Diabetes (>350 mg/dl) was confirmed in all rats, 4 weeks after STZ administration. Rats were left untreated until 35 to 49 days after STZ. Compound D (1, 3, or 10 mg/kg), Compound E (10 mg/kg), or vehicle were dosed daily p.o. following confirmation of hyperalgesia and/or nerve conduction velocity deficits. In separate experiments, onset of treatment was delayed until 60 to 90 days after STZ administration. Nerve conduction velocity or withdrawal response to thermal stimulation of hind paws was measured at intervals, usually bi-weekly for thermal response and monthly for nerve conduction velocity.

General Method for db/db Mice Study

Spontaneously diabetic mice (db/db mice) and non-diabetic littermates were obtained from Jackson labs. Mice were left untreated until 7 to 8 months of age (or after 4 to 5 months of chronic diabetes) and then dosed daily with Compound F (1 mg/kg) p.o. Nerve conduction velocity was measured prior to the onset and after eight weeks of treatment.

Nerve Conduction Velocity Measurements

Sensory and motor nerve conduction velocities were evaluated using the method of De Koning and Gispen (Peptides 8: 415–422, 1987). Electrophysiological evaluation was carried out within one hour of dosing. Animals were anesthetized with isoflurane and stimulating needle electrodes were inserted close to the sciatic nerve at the sciatic notch and the tibial nerve near the ankle. Recording electrodes were placed over the foot muscles. Stimuli were applied and responses recorded. Motor and sensory nerve conduction velocities were calculated by measuring the distance between the sciatic notch and ankle sites, and the latency between the M-wave and the H-reflex.

Thermal Hyperalgesia

Animals were acclimated to the apparatus for at least 5 min. An infra-red source was placed under below the plantar surface of the rat hind-paw. The intensity of the source was adjusted so that latency for normal rats was about 10 secs. Animals were tested for thermal response latency according to the method of Hargreaves et al (*Pain* 77–88, 1988). Each animal was tested 8 times (4 each hind limb) and the latency of response recorded automatically to nearest 0.1 sec. An average of the last 4 measurements for each paw was calculated (8 total measurements) and noted for each rat.

Figure 31:
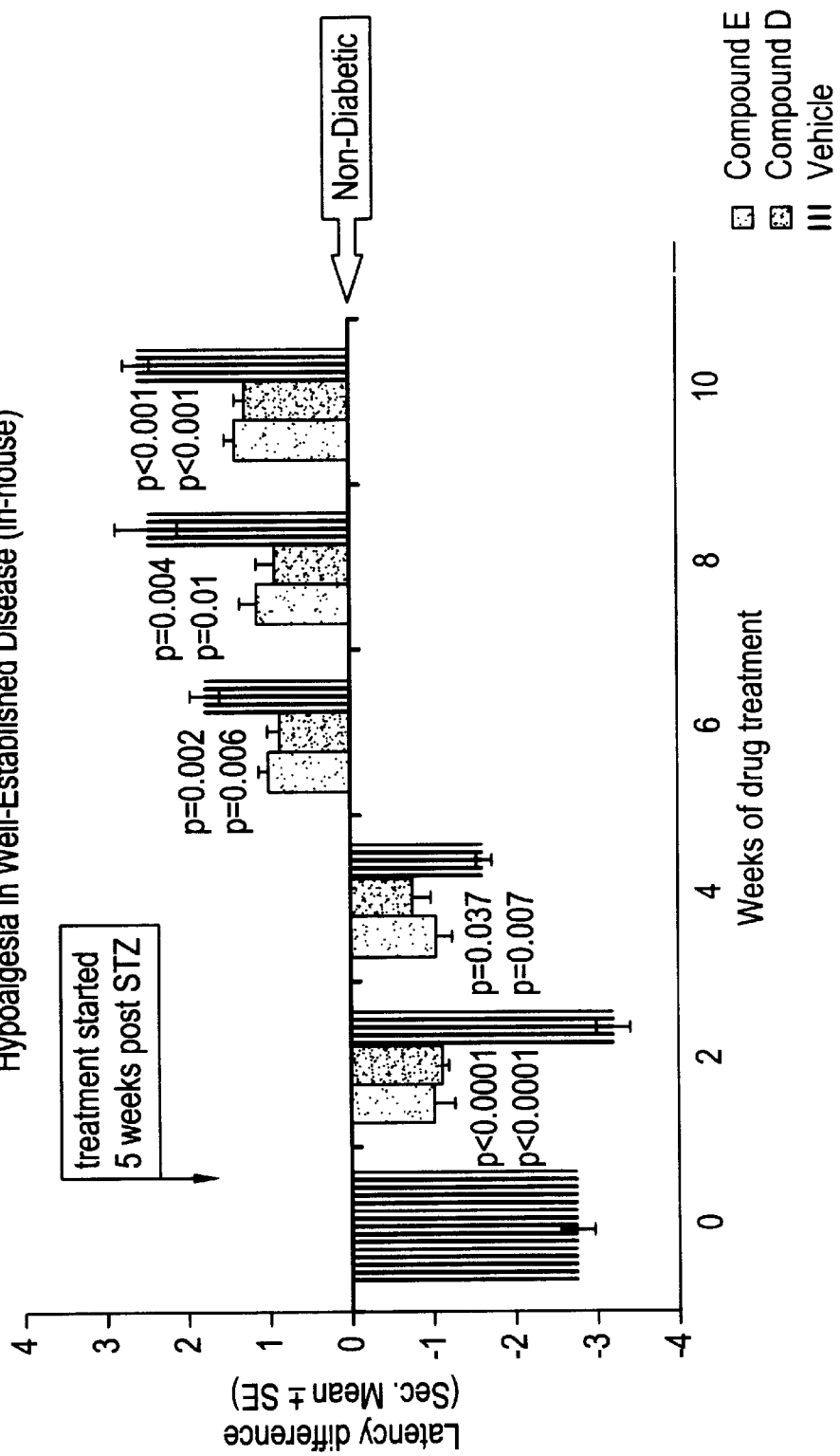
FIG. 31 is a bar graph plotting the withdrawal latency difference scores of non-diabetic rats and STZ-diabetic rats treated with a vehicle, Compound D or 3-carboxy-alpha-(3-mercaptopropyl)benzenepropanoic acid ("Compound E"), against the weeks of treatment.

FIG. 31 shows the effect of NAALADase inhibitor (Compound D and Compound E) treatment on neuropathic pain abnormalities in STZ-diabetic rats. All rats showed apparent hyperalgesia compared to non-diabetic rats prior to NAALADase inhibitor treatment (5 weeks post STZ). However, within two weeks of treatment, neuropathic hyperalgesia was reversed towards normal in both NAALADase inhibitor treated groups. This reversal persisted throughout the subsequent hypoalgesic phase usually seen in prolonged diabetic-STZ rats, with a reduced hypoalgesic phase displayed in NAALADase treated rats.

Figure 32:
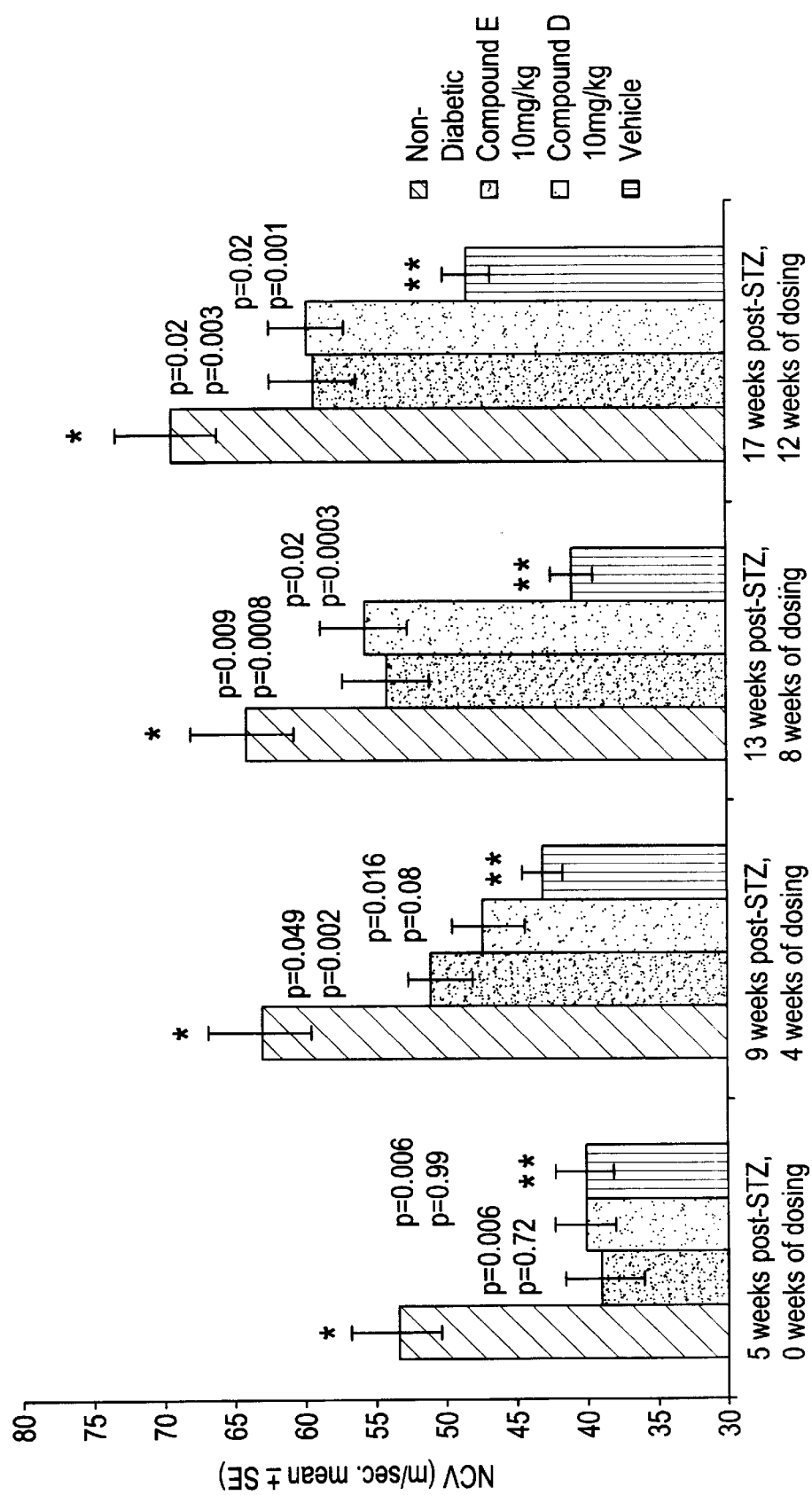
FIG. 32 is a bar graph plotting motor nerve conduction velocity of non-diabetic rats and STZ-diabetic rats- treated with a vehicle, Compound D or Compound E, against the weeks of treatment.

FIG. 32 shows the motor nerve conduction velocity measurements in STZ diabetic rats and non-diabetic controls prior to and at time periods after NAALADase inhibitor treatment. Within 8 weeks of dosing, both NAALADase inhibitors Compound D and Compound E reversed the motor nerve conduction velocity towards normal (non-diabetic values). This effect persisted through 12 weeks of treatment.

Figure 33:
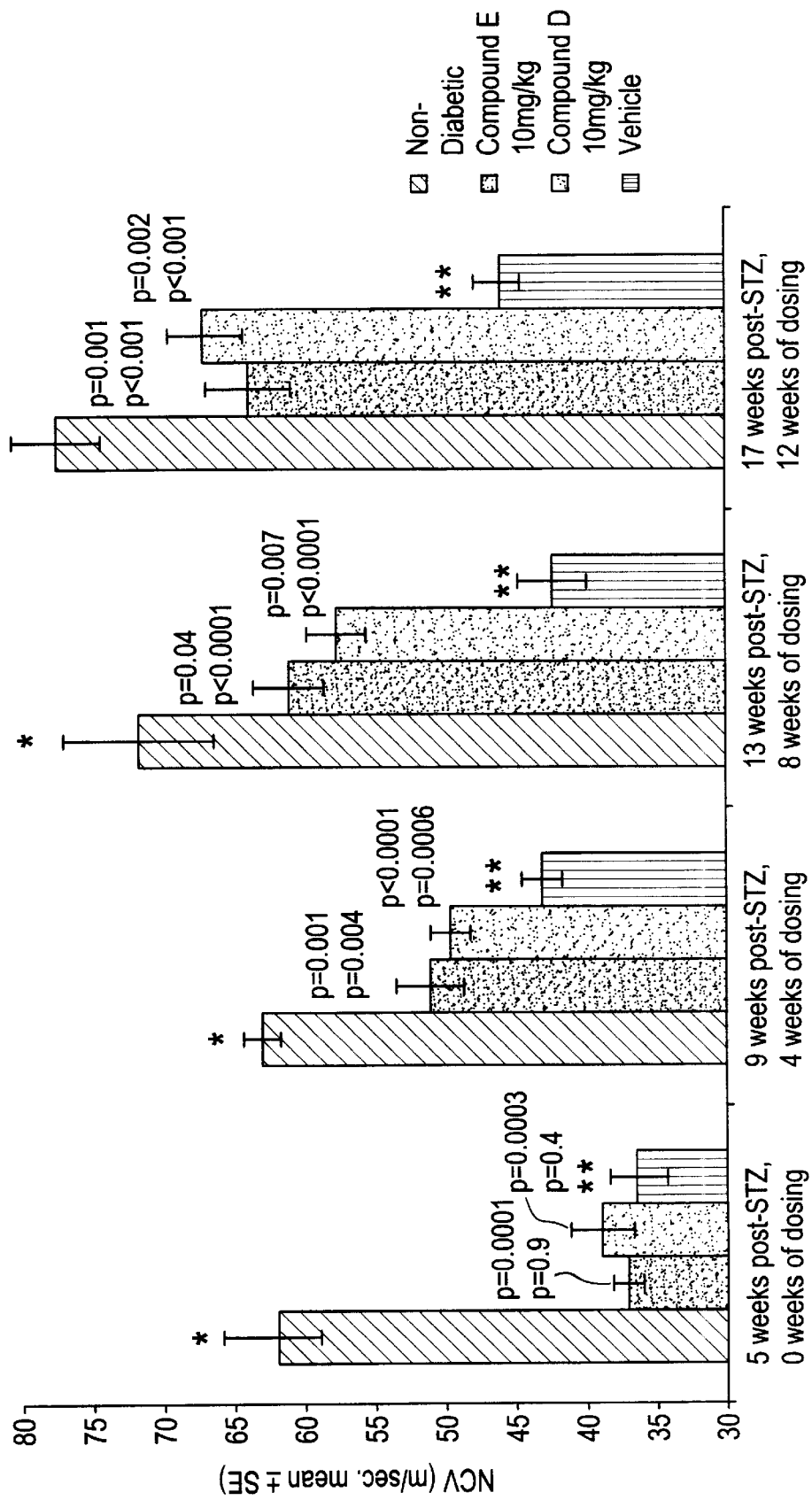
FIG. 33 is a bar graph plotting sensory nerve conduction velocity of non-diabetic rats and STZ-diabetic rats treated with a vehicle, Compound D or Compound E, against the weeks of treatment, where treatment started 5 weeks post STZ.

FIG. 33 shows sensory nerve conduction velocity deficits, similarly tested. NAALADAse inhibitor treatment similarly reversed sensory nerve conduction velocity deficits, significantly so after only 2 weeks of treatment.

Figure 34:
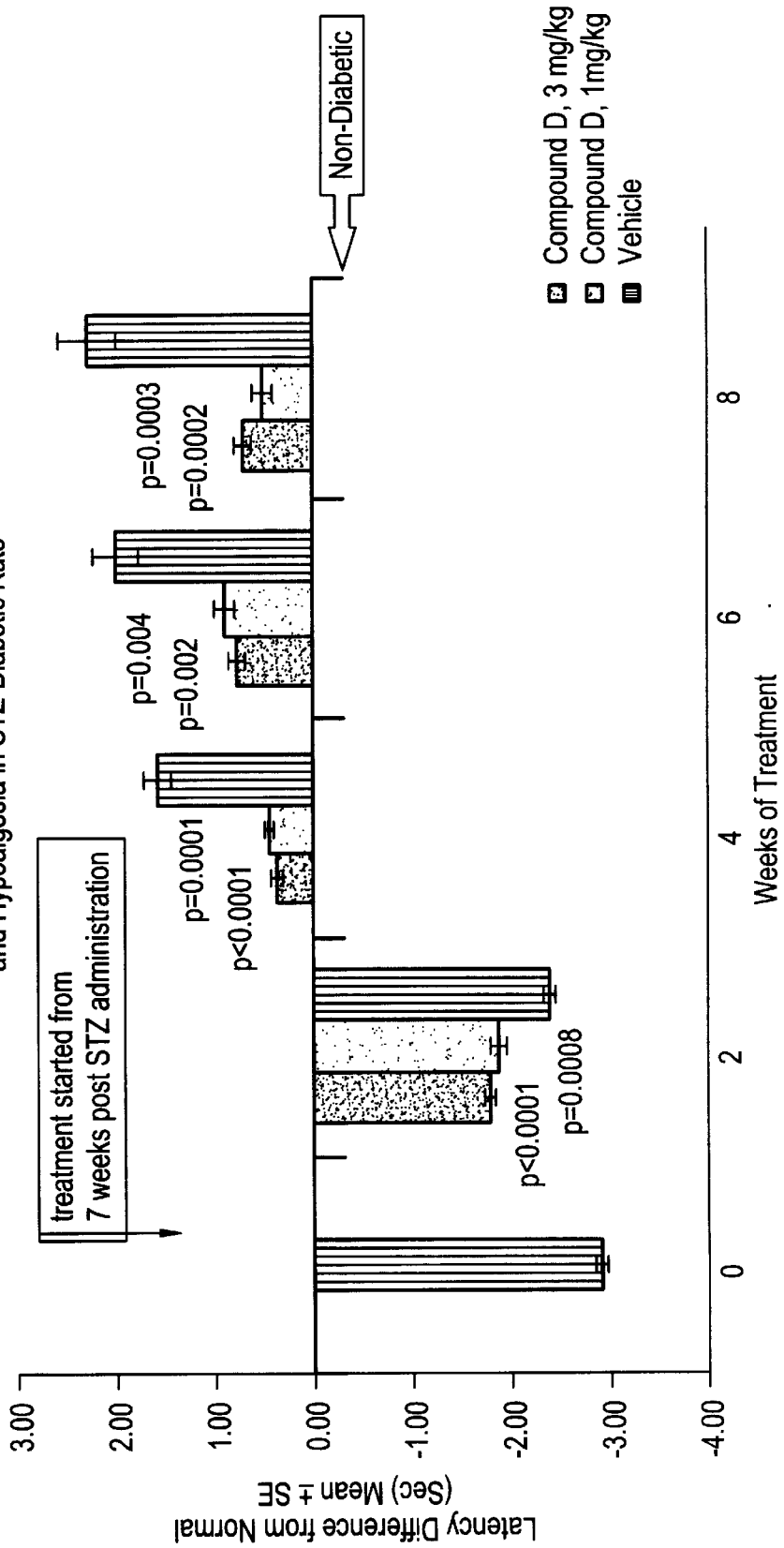
FIG. 34 is a bar graph plotting the withdrawal latency difference scores of non-diabetic rats and STZ-diabetic rats treated with a vehicle or lower doses of Compound D (1 and 3 mg/kg), against the weeks of treatment, where treatment started 7 weeks post STZ.

FIG. 34 shows neuropathic pain abnormalities in another experiment where treatment with lower doses (1 and 3 mg/kg) of the NAALADase inhibitor Compound D was initiated after 7 weeks of STZ treatment. Significant reduction in pain abnormalities were again apparent with both doses of Compound D.

Figure 35:
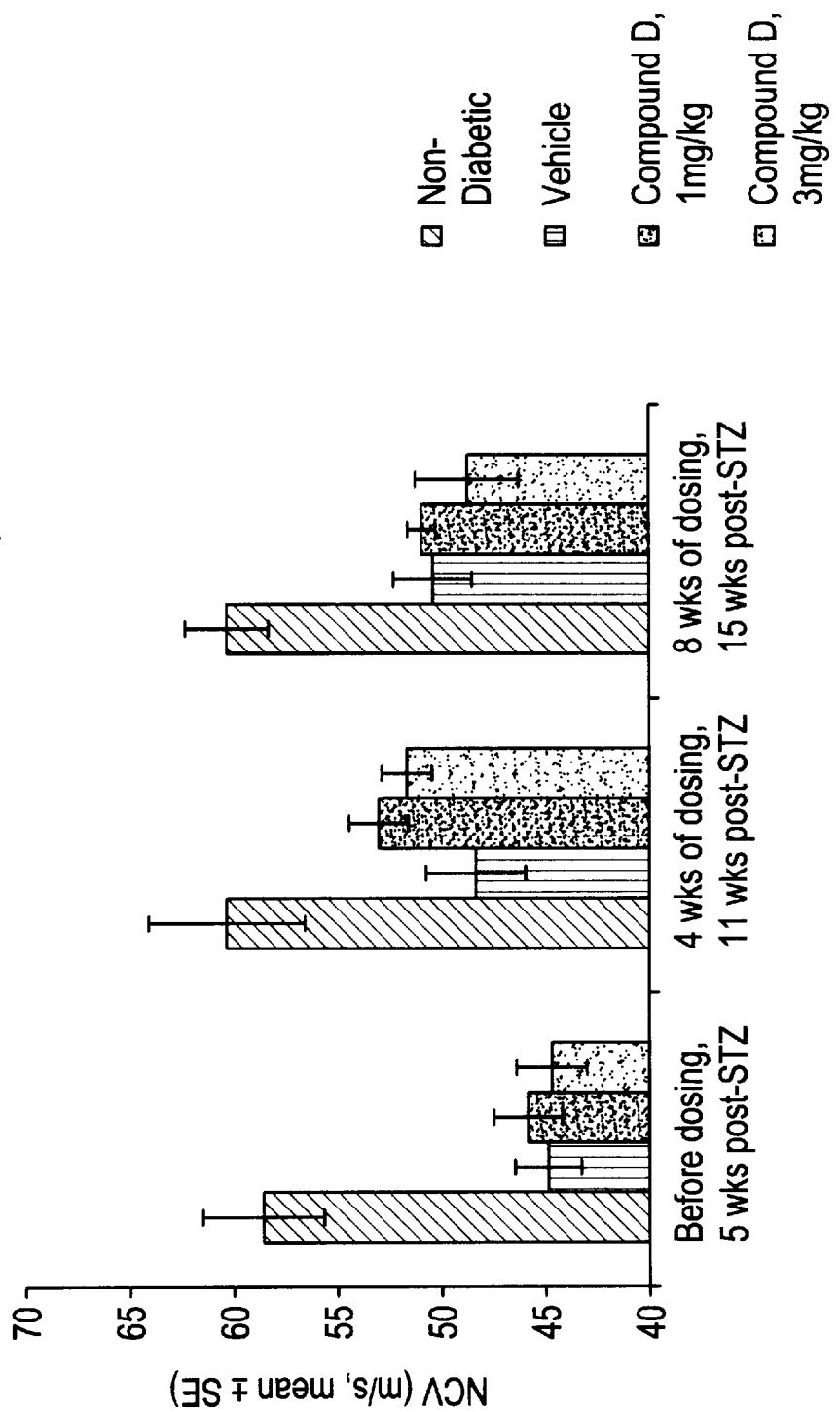
FIG. 35 is a bar graph plotting motor nerve conduction velocity of non-diabetic rats and STZ-diabetic rats treated with a vehicle or lower doses of Compound D (1 and 3 mg/kg), against the weeks of treatment, where treatment started 7 weeks post STZ.
Figure 36:
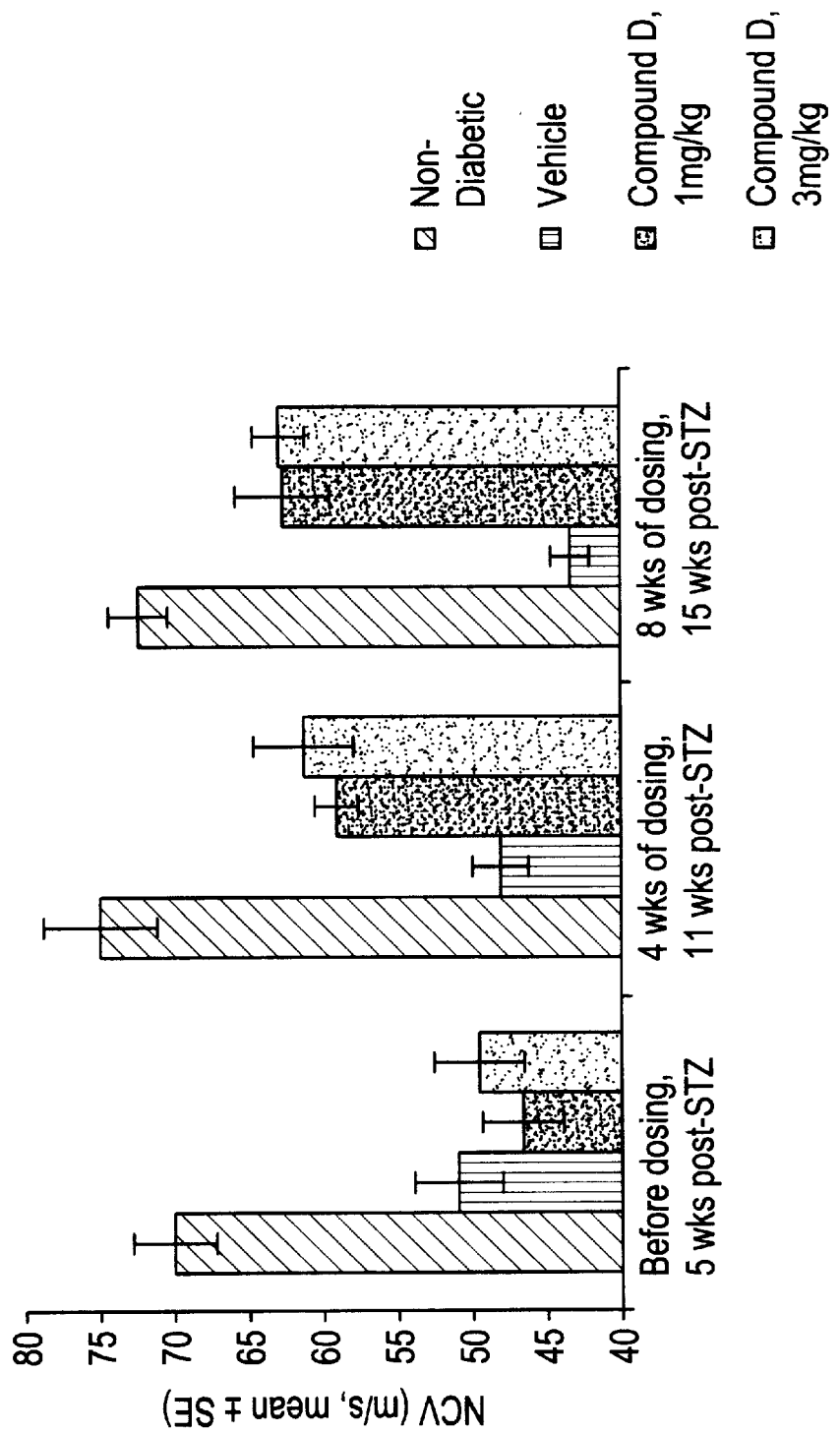
FIG. 36 is a bar graph plotting sensory nerve conduction velocity of non-diabetic rats and STZ-diabetic rats treated with a vehicle or lower doses of Compound D (1 and 3 mg/kg), against the weeks of treatment, where treatment started 7 weeks post STZ.

FIGS. 35 and 36 show sensory and motor nerve conduction velocity, respectively, in these chronically diabetic STZ rats treated with the lower doses of Compound D. Sensory nerve conduction was significantly improved towards normal within 4 weeks of treatment whereas motor nerve conduction remained unimproved by these low doses, even 8 weeks after dosing.

Figure 37:
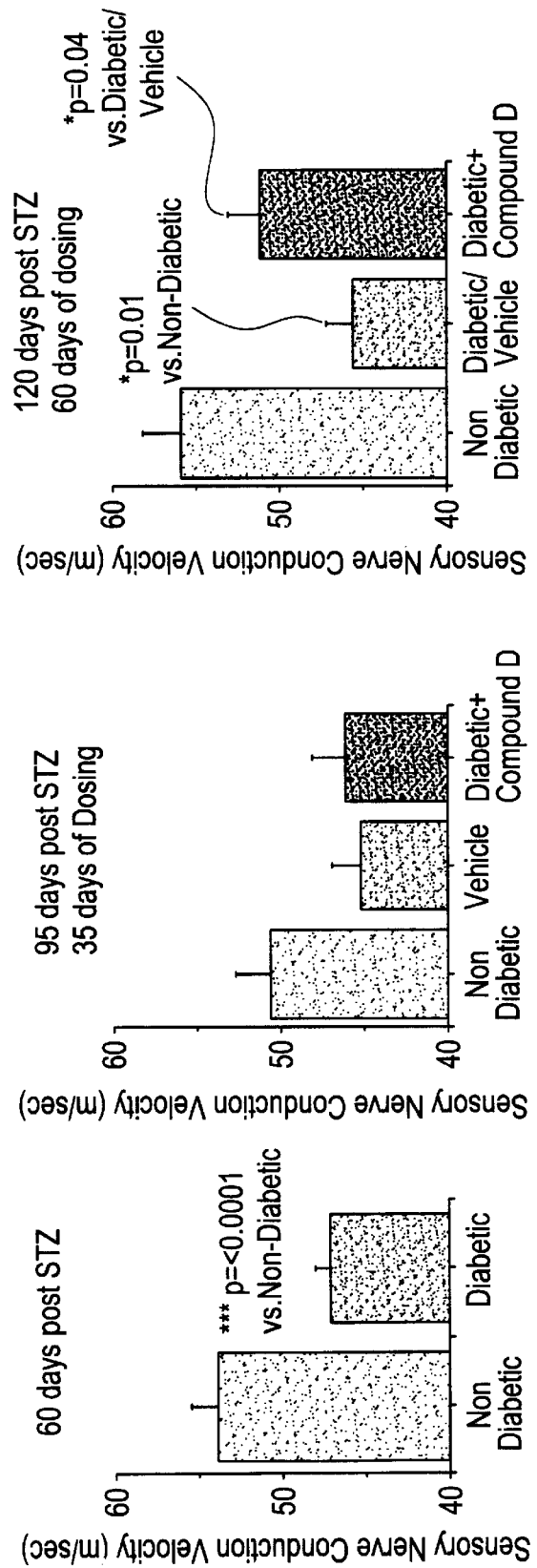
FIG. 37 are bar graphs plotting sensory nerve conduction velocity of non-diabetic rats and STZ-diabetic rats treated with a vehicle or Compound D at 35 days and 60 days after treatment, where treatment started 60 days post STZ.
Figure 38:
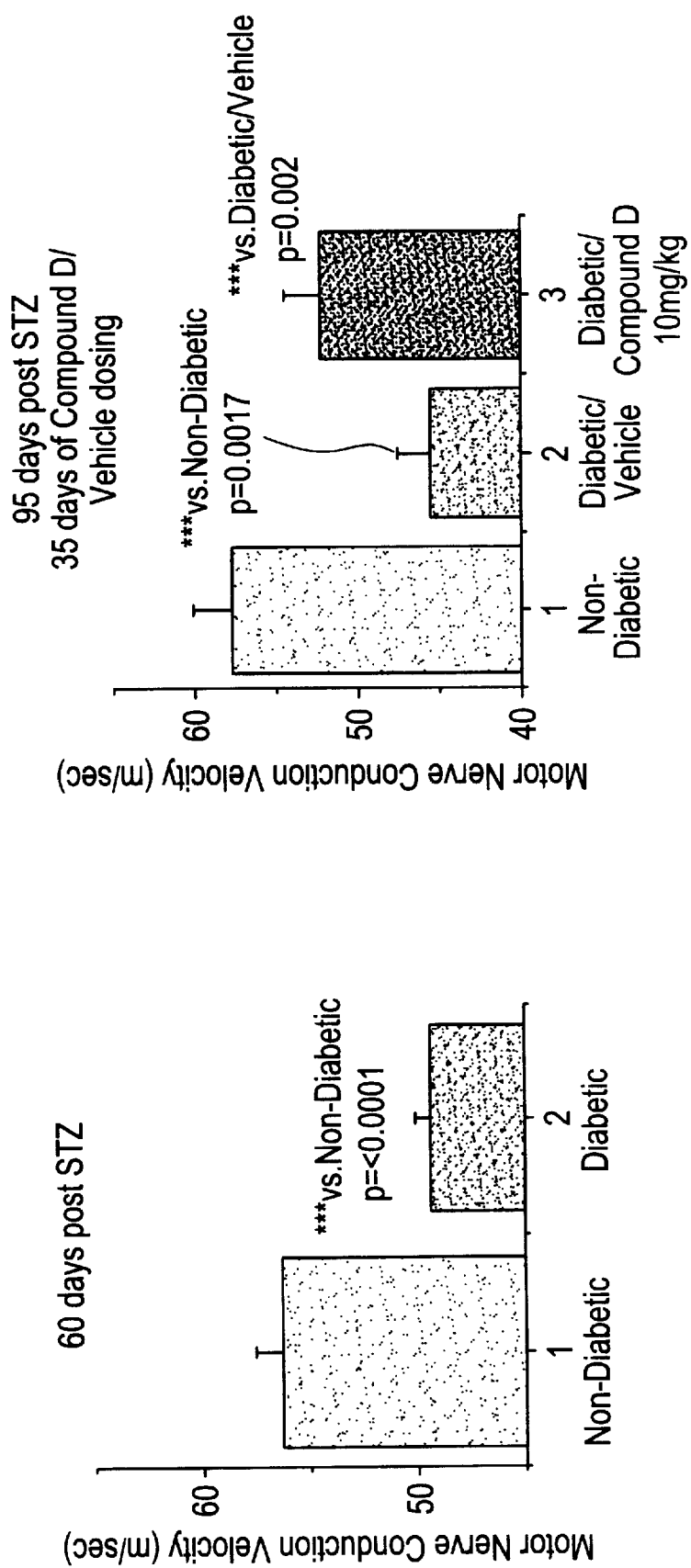
FIG. 38 are bar graphs plotting motor nerve conduction velocity of non-diabetic rats and STZ-diabetic rats treated with a vehicle or Compound D at 35 days after treatment, where treatment started 60 days post STZ.
Figure 39:
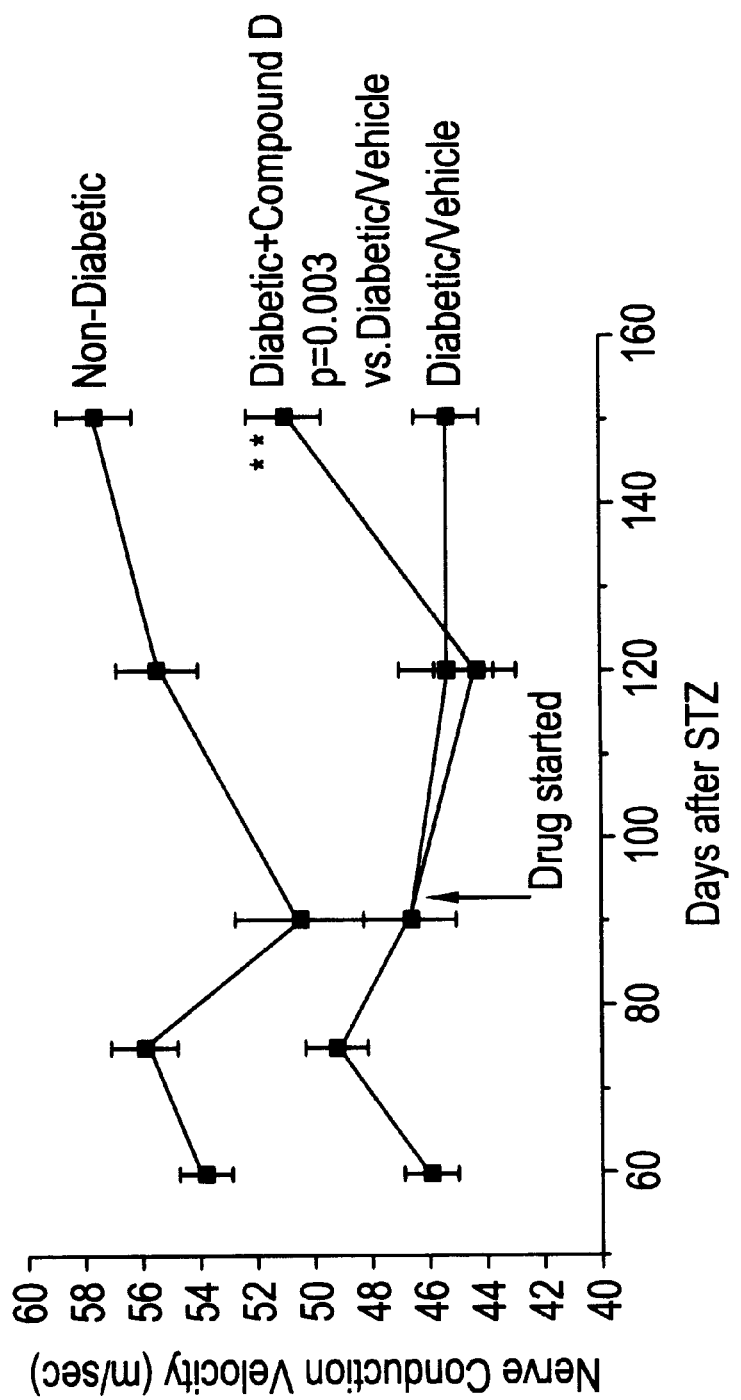
FIG. 39 is a graph plotting sensory nerve conduction velocity of non-diabetic and STZ-diabetic rats treated with a vehicle or Compound D, against the days post STZ, where treatment started 90 days post STZ.

FIGS. 37 and 38 show sensory and motor nerve conduction velocity measurements generated from an external CRO in a similar chronically diabetic STZ model, where rats were left untreated until 60 days after STZ treatment. Partial reversal of both deficits was again produced by Compound D treatment. FIG. 39 shows the same where treatment was delayed yet further, until 90 days after STZ.

Figure 40:
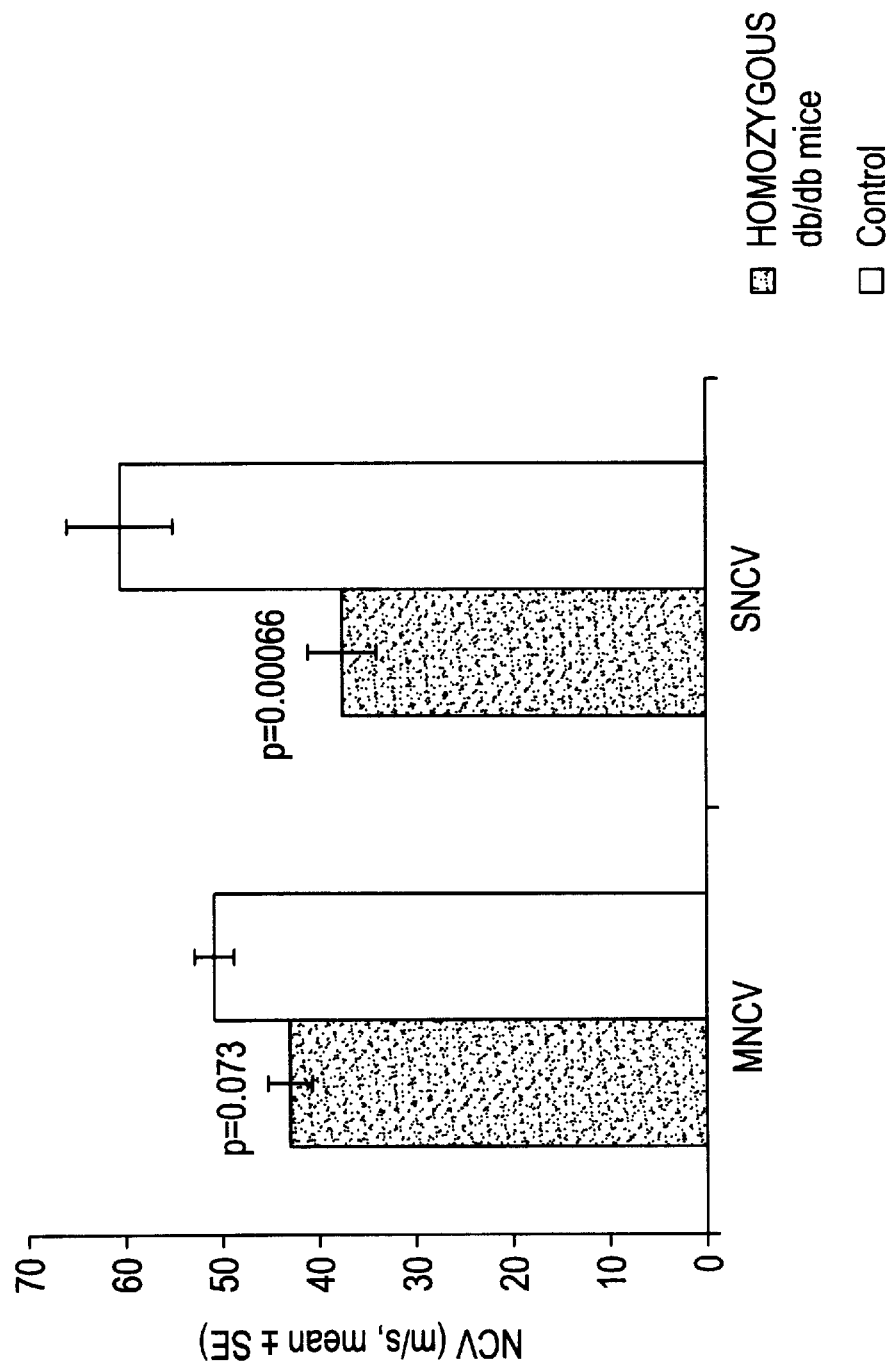
FIG. 40 is a bar graph plotting motor and sensory nerve conduction velocities of non-diabetic mice and db/db diabetic mice before treatment with a NAALADase inhibitor.
Figure 41:
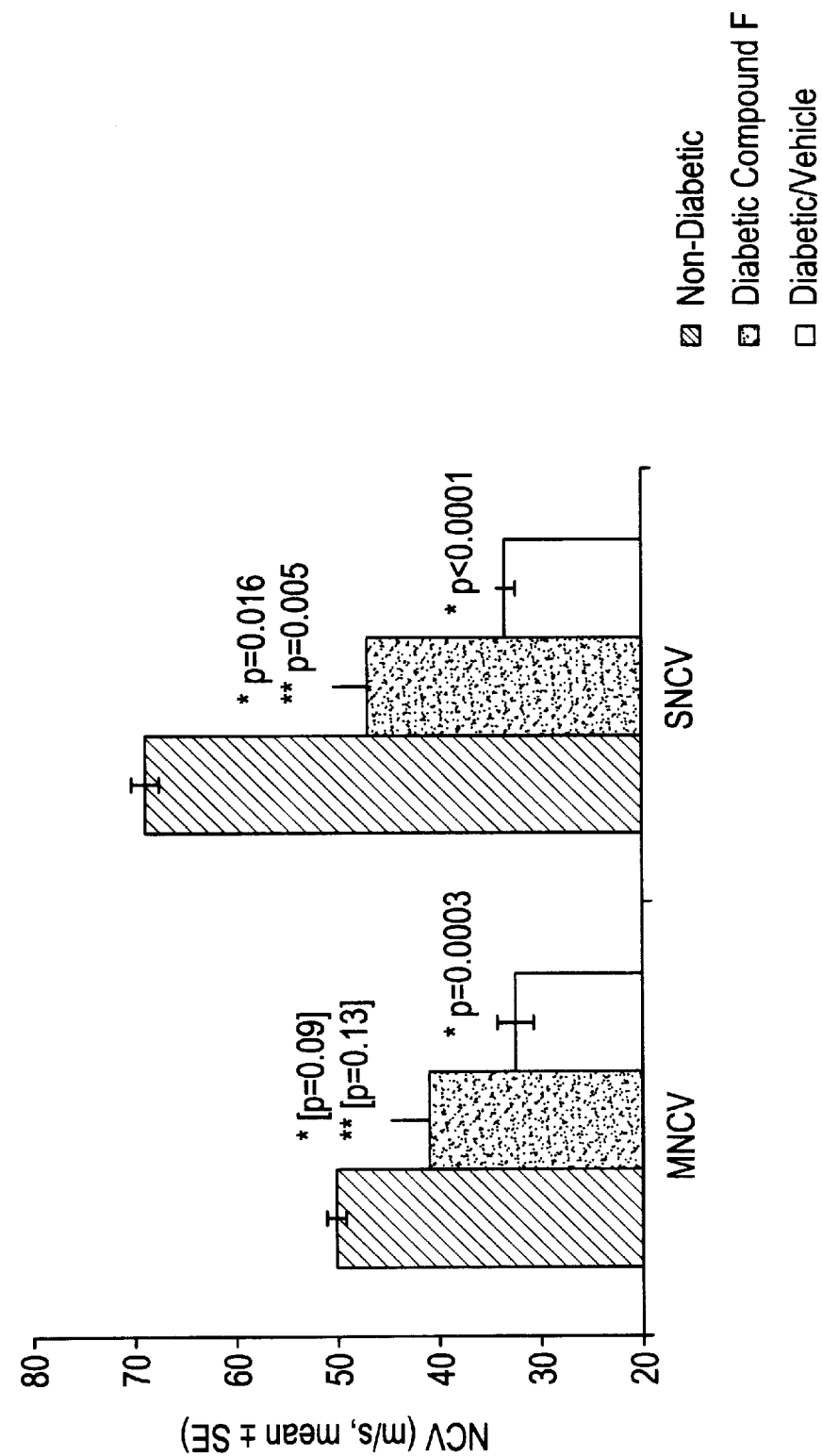
FIG. 41 is a bar graph plotting motor and sensory nerve conduction velocities of non-diabetic mice and db/db diabetic mice after treatment with 3-carboxy-5-(1,1-dimethylethyl)-alpha-(3-mercaptopropyl)benzenepropanoic acid ("Compound F").

FIG. 40 shows nerve conduction velocity measurements from a genetic mouse model of diabetes, at 6 to 7 months of age (after about 4 months of chronic diabetes). A significant impairment in sensory NCV was apparent at this time. FIG. 41 shows the nerve conduction velocity in these mice after 8 weeks of treatment with another, more potent NAALADase inhibitor administered at 1 mg/kg daily. Significant improvement in the sensory nerve conduction was apparent following drug treatment.

Example 14

Effect of NAALADase Inhibitors on Onset of ALS

The effect of NAALADase inhibitors on the onset of ALS, was tested using the transgenic mice model of, familial amyotrophic lateral sclerosis (FALS), which is detailed in Gurney, M., *Annals of Neurology* (1996) 39:147–157, and otherwise well known in the art. One month old transgenic GlH mice were treated with daily intraperitoneal injections of a vehicle (50 mM HEPES-buffered saline) or a NAALADase inhibitor (50 mg/kg Compound A). Clinical symptoms of the mice were monitored daily. The onset of clinical disease was scored by examining each mouse for its shaking of limbs when suspended in the air by its tail, cross spread of spinal reflexes, hindlimb paralysis, body weight and wheel running activity.

The results, set forth below in TABLE IV, show that disease onset was delayed in mice treated with a NAALADase inhibitor.

TABLE IV

| | EFFECT OF NAALADASE INHIBITOR ON ONSET OF CLINICAL DISEASE | | |
|---|---|---|---|
| STUDY | DISEASE ONSET FOR COMPOUND A TREATED MICE (days) | DISEASE ONSET FOR VEHICLE TREATED MICE (days) | DIFFERENCE |
| Study 1 | 221 | 189 | 32 |
| Study 2 | 166 | 141 | 25 |

Example 15

Effect of NAALADase Inhibitor on ALS Survival and Clinical Symptoms

The effect of NAALADase inhibitors on ALS survival and clinical symptoms was tested using again the transgenic mice model of FALS. One month old transgenic G1H mice were treated daily with a vehicle (50 mM HEPES-buffered saline) or a NAALADase inhibitor (30 mg/kg Compound B) p.o. (by oral administration). Clinical symptoms of the mice were monitored twice a week. Such symptoms included shaking of limbs, gait, dragging of hind limbs, crossing of limbs, righting reflex and mortality. Gait and crossing of limbs were graded on an arbitrary scale ranging from 0 to 3, with 0 representing most normal and 3 representing least normal, e.g. severest difficulty in walking or crossing limbs. Righting reflex was measured by the time (seconds) it took the mice to right themselves when placed on their sides on a flat surface.

The results, set forth in FIGS. 24–30, show that survival was prolonged and clinical symptoms were attenuated in mice treated with a NAALADase inhibitor.

Example 16

Protective Effect of NAALADase Inhibitors in Experimental Rat Glaucoma

Experimental Protocol

All experiments complied with the Association for Research in Vision and Ophthalmology Statement for the Use of Animals in Ophthalmic and Vision Research. 82 male Brown Norway rats (Rattus norvegicus), each weighing approximately 250 gm, were treated using procedures approved by the Animal Care Committee of the Johns Hopkins University School of Medicine. The rats were housed with a 12 hour light/12 hour dark cycle and fed ad libitum. EXPERIMENTAL GLAUCOMA: Unilateral elevation of intraocular pressure ("IOP") was produced in 56 rats by microinjection of hypertonic saline into episcleral veins, following procedures described in Morrison, J. et al., *IOVS* (March 1998) 39:526–531. Beginning on the day of IOP elevation, the rats were treated daily with intraperitoneal injections of either a vehicle (23 rats with 50 mM HEPES-buffered saline) or a NAALADase inhibitor (11 rats with 10 mg/kg of Compound A and 22 rats with 10 mg/kg of Compound B). 11 saline treated rats, 11 Compound A treated rats and 11 Compound B treated rats were sacrificed at 8 weeks, and the remaining rats at 12 weeks, after initial IOP elevation. OPTIC NERVE TRANSECTION: The optic nerve was transected unilaterally in 26 rats under intraperitoneal pentobarbital anesthesia. The conjunctiva was opened with scissors and the optic nerve exposed by traction on extraocular muscles. The transection was performed with microscissors 5 mm posterior to the globe, with specific attention to avoidance of injury to major ocular blood vessels. Immediately after transection, the retina was examined ophthalmoscopically to assure that the retinal arterial blood supply was not disrupted. The conjunctiva was closed with absorbable suture and the eye dressed with antibiotic ointment. Beginning on the day of transection, the rats were treated daily with intraperitoneal injections of either a vehicle (9 rats with 50 mM HEPES-buffered saline) or a NAALADase inhibitor (8 rats with 10 mg/kg of Compound A and 9 rats with 10 mg/kg of Compound B). 5 saline treated rats, 3 Compound A treated rats and 4 Compound B treated rats were sacrificed at 2 weeks, and the remaining rats at 4 weeks, after transection.

OPTIC NERVE COUNTING: The rats were sacrificed by exsanguination under deep pentobarbital anesthesia. They were perfused through the heart with 2% paraformaldehyde/2% glutaraldehyde in 0.1 M phosphate buffer, pH 7.2, and the eyes with attached optic nerves were removed. A cross-section of the optic nerve from both experimental (glaucoma or transection) and control eyes was removed 1.5 mm posterior to the globe, 1 mm in thickness, and post-fixed in 2% osmium tetroxide in buffer. These were processed into epoxy resin, sectioned at 1 micron and stained with toluidine blue.

The area of the optic nerve cross-section was measured by outlining its outer border at 10× magnification on an image analysis system (Universal Imaging Corp., Westchester, Pa.) with Synsys digital camera and Metamorph software. Three area measurements were taken and the mean value was determined. To measure the density and fiber diameter distributions, images were captured with a 100× phase contrast objective from 10 different areas of each nerve. These were edited to eliminate non-neural objects and the size of each axon internal to the myelin sheath (its minimum diameter) and the density of axons/square mm were calculated for each image and nerve. The mean density was multiplied by total nerve area to yield fiber number for each nerve. The total fiber number in glaucoma or transection nerves was compared to the normal, fellow eye of each rat to yield a percent loss value. The number of axons counted among the 10 images was an approximately 20% sample of the 80–90,000 axons in normal rat nerves. The person measuring axon number was masked to the protocol conducted on the nerves.

Results

EXPERIMENTAL GLAUCOMA: The mean fiber percent difference in the saline-treated, control rats was significantly lower in their glaucoma eyes compared to their normal eyes, with a mean fiber loss of 14.44±5.75% (n=11 rats; TABLE V) in the 8 week follow-up group, and 8.15±7.84% in the 12 week follow-up group (n=12 rats; TABLE VI).

By contrast, there was no significant loss of fibers in either the 8 week or 12 week NAALADase inhibitor-treated rats. The mean percent fiber loss in each NAALADase inhibitor-treated group was statistically less than the loss in the saline-treated, control groups (at 8 weeks, p=0.05 for Compound A and p=0.02 for Compound B).

TABLE V

EXPERIMENTAL GLAUCOMA RESULTS

| 8 WEEK GROUP | N | IOP INTEGRAL DIFFERENCE | FIBER NUMBER | PERCENT DIFFERENCE |
| --- | --- | --- | --- | --- |
| Compound A | 11 | 85 ± 37.5 | 79156 ± 2436 * | −1.82 ± 2.92 |
| Compound B | 11 | 116 ± 33.2 | 80785 ± 2121 ** | −0.82 ± 2.97 |
| Control | 11 | 104 ± 26.4 | 68295 ± 4617 | 14.44 ± 5.75 |

TABLE VI

EXPERIMENTAL GLAUCOMA RESULTS

| 12 WEEK GROUP | N | IOP INTEGRAL DIFFERENCE | FIBER NUMBER | PERCENT DIFFERENCE |
| --- | --- | --- | --- | --- |
| Compound B | 11 | 109 ± 45.2 | 90504 ± 1718 | −3.21 ± 2.86 |
| Control | 12 | 158 ± 66.5 | 79827 ± 6783 | 8.15 ± 7.84 |

IOP Integral Difference=difference in IOP exposure between glaucoma eye and normal eye in each rat (mm Hg—days). Percent Difference=mean percent difference in fiber number between glaucoma and normal eye in each rat (positive value indicates fewer fibers in the glaucoma eye). Differences in IOP Integral Difference are not significant (p>0.05).

Differences in Percent Difference between drug-treated and saline-treated, control rats at 8 weeks post insult are significant (p=0.05* and p=0.02**).

OPTIC NERVE TRANSECTION: The experimental transection data suggest a slowing or rescue of ultimate RGC death in rats treated with NAALADase inhibitors at 2 weeks after transection. At 2 weeks after transection, both drug-treated groups had more remaining RGC axons than did the saline-treated, control group, judged either by absolute number of fibers or percent difference between transected eye and normal eye in each rat (TABLE VII). Rats treated with Compound A and Compound B had, respectively, 3 times and twice as many remaining axons as the saline-treated rats. All or nearly all RGC die within the first 2 months after transection, regardless of any pharmacological treatment. Thus, by 4 weeks after transection, more than 80% of RGC axons were gone in all groups (TABLE VIII). At 4 weeks after transection, there were no significant differences between the drug-treated rats and the saline-treated rats.

TABLE VII

OPTIC NERVE TRANSECTION

| 2 WEEKS SURVIVAL | N | FIBER NUMBER | PERCENT DIFFERENCE |
| --- | --- | --- | --- |
| Compound A | 3 | 26,426 ± 23,025 | 65.3 ± 30.9 |
| Compound B | 4 | 19,550 ± 11,383 | 75.3 ± 14.8 |
| Control | 5 | 8,220 ± 9,337 | 90.2 ± 10.7 |

TABLE VIII

OPTIC NERVE TRANSECTION

| 4 WEEKS SURVIVAL | N | FIBER NUMBER | PERCENT DIFFERENCE |
| --- | --- | --- | --- |
| Compound A | 5 | 13,599 ± 7,868 | 82.4 ± 8.9 |
| Compound B | 5 | 5,162 ± 5,017 | 93.4 ± 6.2 |
| Control | 4 | 10,449 ± 8,157 | 86.9 ± 10.6 |

Percent Difference=mean percent difference in fiber number between glaucoma and normal eye in each rat (positive value indicates fewer fibers in the glaucoma eye). Differences in Percent Difference between drug-treated and saline-treated, control rats are not statistically significant (p=0.05).

Example 17

Neuroprotective Effect of NAALADase Inhibitors in Transgenic Mouse Model of Huntington's Disease Behavioral Testing (Rotarod)

Figure 42:
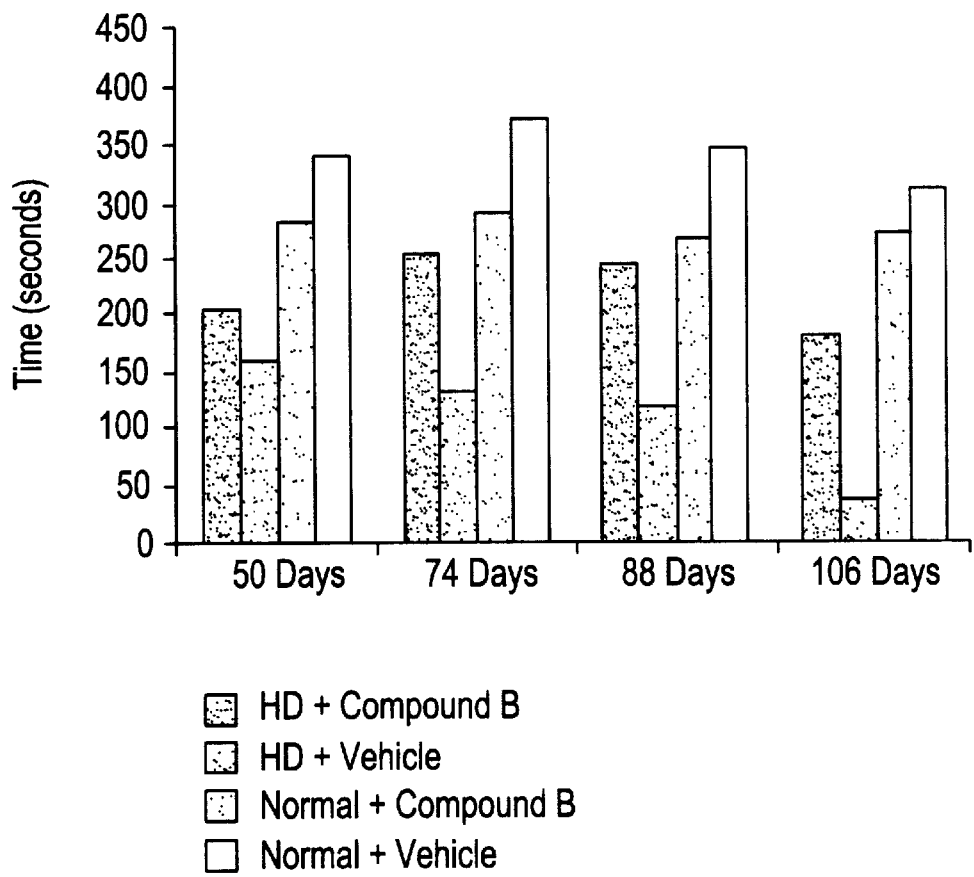
FIG. 42 is bar graph comparing the rotarod performance of transgenic HD mice and normal non-HD mice treated with Compound. B, and transgenic HD mice and normal non-HD mice treated with a vehicle.

Transgenic HD mice of the N171-82Q strain and non-transgenic littermates were treated with NAALADase inhibitor Compound B (30 mg/kg) or a vehicle from 10 weeks of age. The mice were placed on a rotating rod ("rotarod"). The length of time at which the mouse fell off the rotarod was recorded as a measure of motor coordination. FIG. 42 shows that transgenic HD mice treated with Compound B stayed longer on the rotarod than similar transgenic HD mice treated with a vehicle. The treatment with Compound B had no effect on the rotarod performance of normal non-HD mice.

Figure 43:
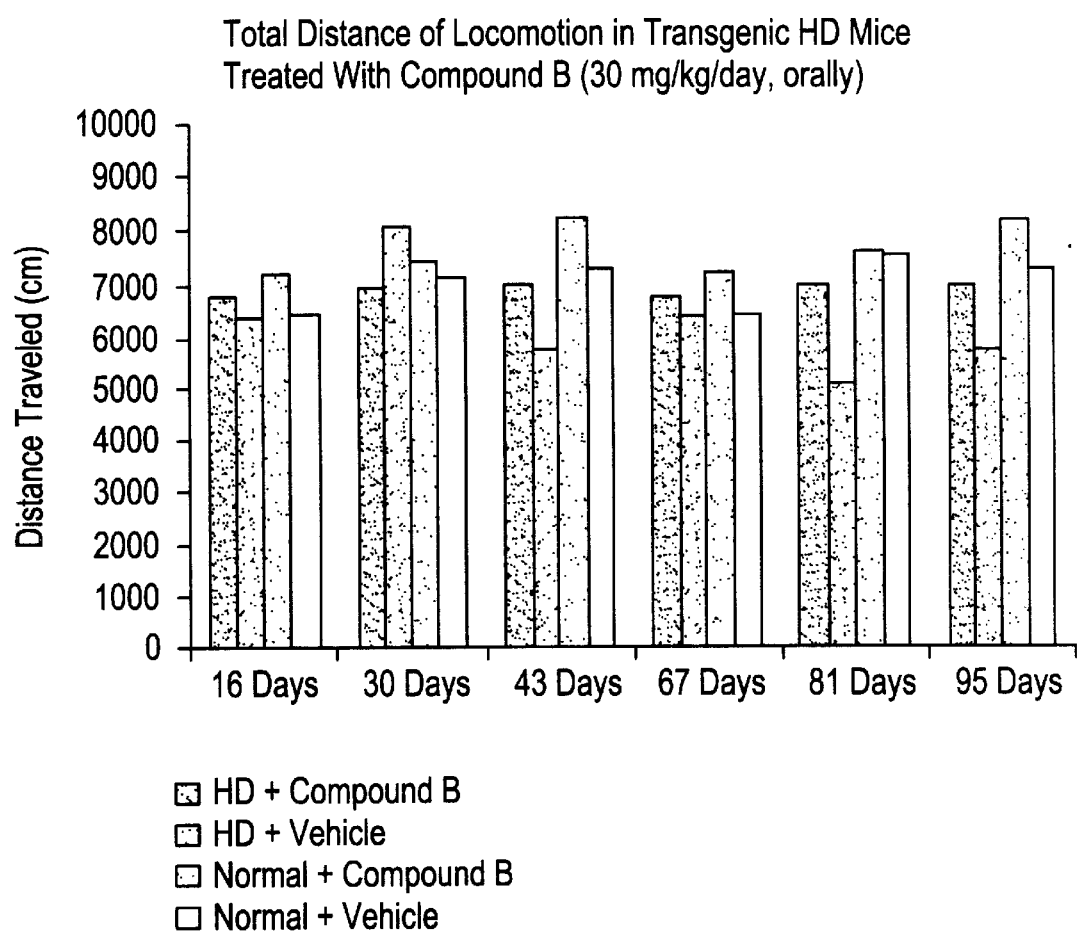
FIG. 43 is a bar graph comparing the total distance traveled by transgenic HD mice and normal non-HD mice treated with Compound B, and transgenic HD mice and normal non-HD mice treated with a vehicle.

The total distance traveled by the mice was also recorded as a measure of overall locomotion. FIG. 43 shows that while the vehicle treated HD mice demonstrated the lowest mean locomotor score, the treatment with NAALADase inhibitor had no apparent effect on overall locomotion.

Survival

The effects of Compound B and vehicle on the survival of transgenic HD mice (N171-82Q) were evaluated. Thirteen mice (six male and seven female) were assigned to the Compound B treatment group, and fourteen mice (six male and eight female) were assigned to the vehicle treatment group. Treatment was continued until all the mice died.

Figure 44:
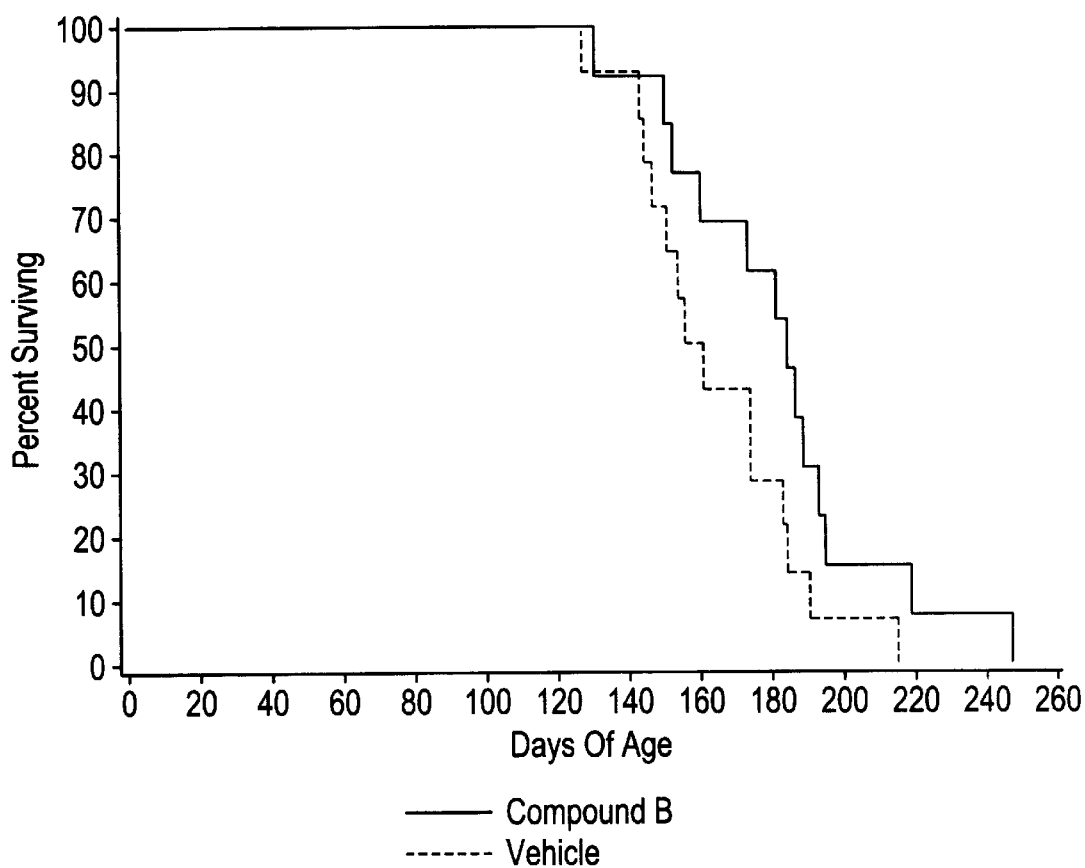
FIG. 44 is a graph plotting the survival time of transgenic D mice treated with Compound B or a vehicle.

FIG. 44 shows the survival distributions over time by treatment group. The median survival time is 184 days for the Compound B treatment group, and 158.5 days for the vehicle treatment group. Although the Compound B treatment group had a longer median survival time than the vehicle treatment group, the difference is not statistically significant (p-value=0.07).

Figure 45:
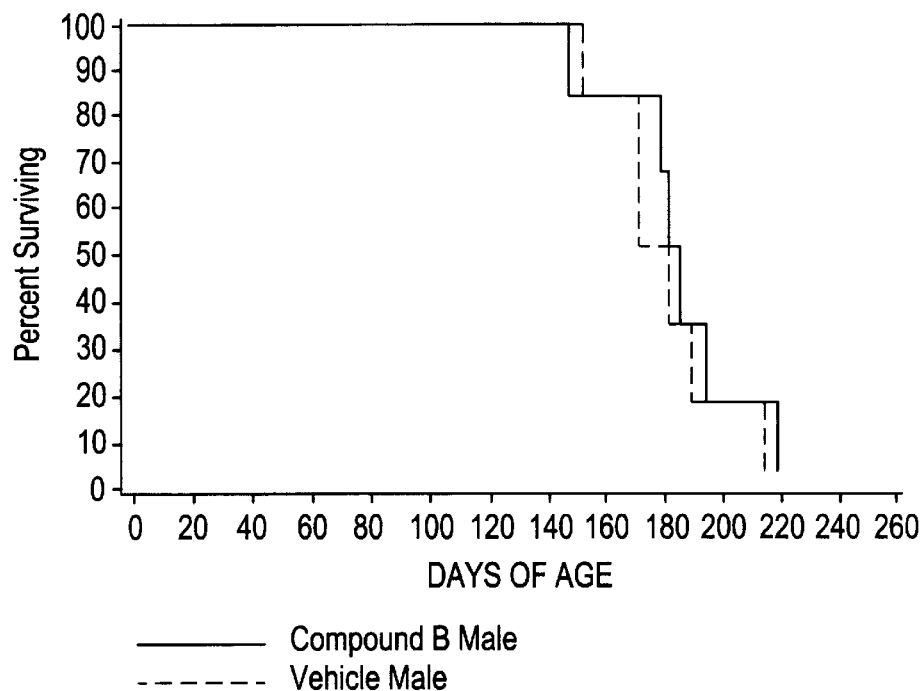
FIG. 45 is a graph plotting the survival time of male transgenic HD mice treated with Compound B or a vehicle.
Figure 46:
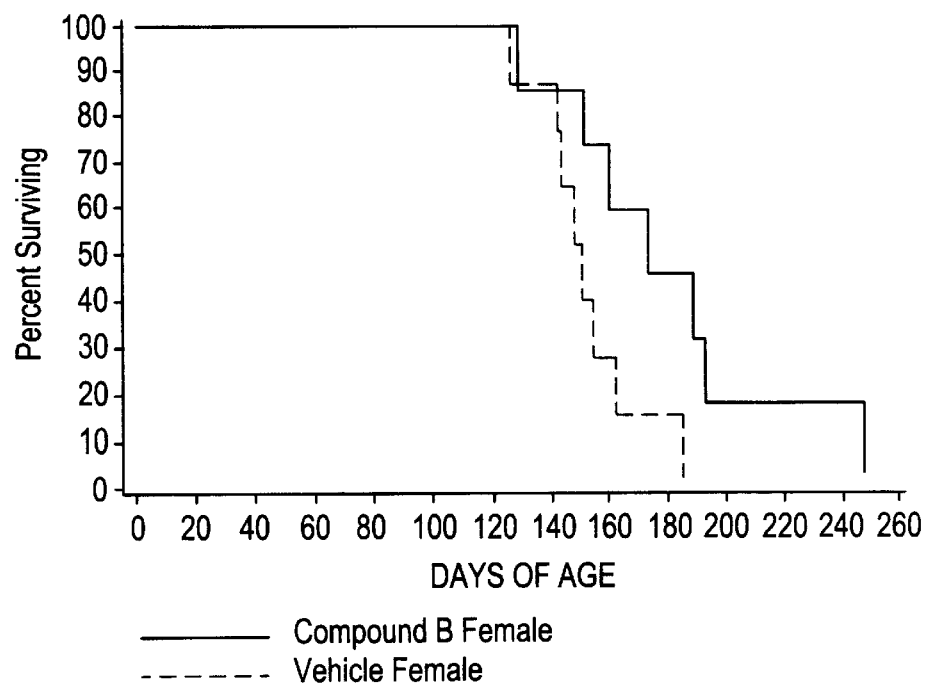
FIG. 46 is a graph plotting the survival time of female transgenic HD mice treated with Compound B or a vehicle.

FIGS. 45 and 46 show the survival distributions over time by treatment group and sex. When analyzing the results specific to sex, female mice treated with Compound B had significantly prolonged survival time (p-value=0.03) compared to their vehicle treated counterparts. Within the vehicle treatment group, the males have better survival times than the females although this trend was not observed in the Compound B treatment group. The data suggest that sex may influence survival distributions over time.

Example 18

A patient is suffering from any disease, disorder or condition where NAALADase levels are altered, including any of the diseases, disorders or conditions described above. The patient may then be administered an effective amount of a compound of the invention. It is expected that after such treatment, the patient would not suffer any significant injury due to, would be protected from further injury due to, or would recover from the disease, disorder or condition.

All publications, patents and patent applications identified above are herein incorporated by reference, as though set forth herein in full.

The invention being thus described, it will be apparent to those skilled in the art that the same may be varied in many ways without departing from the spirit and scope of the invention. Such variations are included within the scope of the following claims.

We claim:

1. A compound of formula I

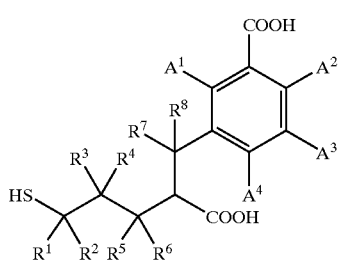

or a pharmaceutically acceptable equivalent of said compound, wherein:

$R^1$, $R^2$, $R^3$, $R^4$, $R^5$, $R^6$, $R^7$ and $R^8$ are independently hydrogen or $C_1$–$C_3$ alkyl;

$A^1$, $A^2$, $A^3$ and $A^4$ are independently hydrogen, $C_1$–$C_6$ alkyl, $C_1$–$C_6$ alkoxy, halo, nitro, phenyl, phenoxy, benzyl, benzyloxy or —COOH, or any adjacent two of $A^2$, $A^3$ and $A^4$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

2. The compound of claim 1, wherein:
$R^1$, $R^2$, $R^3$, $R^4$, $R^5$, $R^6$, $R^7$ and $R^8$ are independently hydrogen or methyl; and
$A^1$, $A^2$, $A^3$ and $A^4$ are independently hydrogen, $C_1$–$C_4$ alkyl, $C_1$–$C_2$ alkoxy, halo, nitro, phenyl, phenoxy, benzyloxy, nitro or —COOH.

3. The compound of claim 1, wherein any adjacent two of $A^2$, $A^3$ and $A^4$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

4. The compound of claim 1, wherein said compound is selected from the group consisting of:

3-carboxy-alpha-(3-mercaptopropyl)-benzenepropanoic acid;

5-(2-carboxy-5-mercaptopentyl)-1,3-benzenedicarboxylic acid;

5-carboxy-2-chloro-alpha-(3-mercaptopropyl)-benzenepropanoic acid;

3-carboxy-4-fluoro-alpha-(3-mercaptopropyl)-benzenepropanoic acid;

3-carboxy-2-chloro-alpha-(3-mercaptopropyl)-benzenepropanoic acid;

3-carboxy-4-chloro-alpha-(3-mercaptopropyl)-benzenepropanoic acid;

5-carboxy-2-fluoro-alpha-(3-mercaptopropyl)-benzenepropanoic acid;

5-carboxy-alpha-(3-mercaptopropyl)-2-methoxy-benzenepropanoic acid;

3-bromo-5-carboxy-alpha-(3-mercaptopropyl)-benzenepropanoic acid;

3-carboxy-alpha-(3-mercaptopropyl)-5-nitro-benzenepropanoic acid;

3-carboxy-5-(1,1-dimethylethyl)-alpha-(3-mercaptopropyl)-benzenepropanoic acid;

5-carboxy-alpha-(3-mercaptopropyl)-2-nitro-benzenepropanoic acid;

2-bromo-5-carboxy-alpha-(3-mercaptopropyl)-benzenepropanoic acid;

(+)-3-carboxy-alpha-(3-mercaptopropyl)-benzenepropanoic acid;

(−)-3-carboxy-alpha-(3-mercaptopropyl)-benzenepropanoic acid;

5-(2-carboxy-5-mercaptopentyl)-[1,1'-biphenyl]-3-carboxylic acid;

2-(2-carboxy-5-mercaptopentyl)-[1,1'-biphenyl]-4-carboxylic acid;

6-(2-carboxy-5-mercaptopentyl)-[1,1'-biphenyl]-2-carboxylic acid;

4-(2-carboxy-5-mercaptopentyl)-[1,1'-biphenyl]-2-carboxylic acid;

3-carboxy-alpha-(3-mercaptopropyl)-5-methoxy-benzenepropanoic acid;

3-carboxy-alpha-(3-mercaptobutyl)-benzenepropanoic acid;

3-carboxy-alpha-(3-mercaptopropyl)-5-(phenylmethoxy)-benzenepropanoic acid;

3-carboxy-alpha-(3-mercaptopropyl)-5-phenoxy-benzenepropanoic acid;

3-carboxy-5-(1,1-dimethylethyl)-alpha-(3-mercaptobutyl)-benzenepropanoic acid; and pharmaceutically acceptable equivalents.

5. The compound of claim 1, wherein said compound is an enantiomer or an enantiomer-enriched mixture.

6. A method for inhibiting NAALADase enzyme activity, treating a glutamate abnormality, effecting a neuronal activity, treating a prostate disease, treating cancer, inhibiting angiogenesis or effecting a TGF-β activity, comprising administering to a mammal in need of such inhibition, treatment or effect, an effective amount of a compound of claim 1.

7. The method of claim 6, wherein said method is for treating a glutamate abnormality selected from the group consisting of a compulsive disorder, stroke, demyelinating disease, schizophrenia, Parkinson's disease, amyotrophic lateral sclerosis, anxiety, anxiety disorder, memory impairment and glaucoma.

8. The method of claim 7, wherein the glutamate abnormality is a compulsive disorder that is alcohol, nicotine or cocaine dependence.

9. The method of claim 6, wherein said method is for effecting a neuronal activity selected from the group consisting of stimulation of damaged neurons, promotion of neuronal regeneration, prevention of neurodegeneration and treatment of a neurological disorder.

10. The method of claim 9, wherein the neuronal activity is treatment of a neurological disorder and said neurological disorder is pain, diabetic neuropathy, peripheral neuropathy caused by physical injury or disease state, traumatic brain injury, physical damage to spinal cord, stroke associated with brain damage, a demyelinating disease or a neurological disorder relating to neurodegeneration.

11. The method of claim 10, wherein said pain is diabetic neuropathic pain.

12. The method of claim 11, wherein said compound is administered in combination with an effective amount of morphine.

13. The method of claim 10, wherein the neurological disorder relating to neurodegeneration is Parkinson's disease.

14. The method of claim 10, wherein the neurological disorder relating to neurodegeneration is amyotrophic lateral sclerosis.

15. The method of claim 6, wherein said method is for treating a prostate disease that is prostate cancer.

16. The method of claim 6, wherein said method is for treating cancer.

17. The method of claim 16, wherein said cancer is of the brain, kidney or testis.

18. The method of claim 6, wherein said method is for inhibiting angiogenesis.

19. The method of claim 6, wherein said method is for effecting a TGF-β activity.

20. The method of claim 19, wherein said effecting a TGF-β activity is increasing, reducing or regulating TGF-β levels, or treating a TGF-β abnormality.

21. The method of claim 20, wherein said effecting a TGF-β activity is treating a TGF-β abnormality, and said TGF-β abnormality is neurodegenerative disorder, extracellular matrix formation disorder, cell-growth related disease, infectious disease, immune related disease, epithelial tissue scarring, collagen vascular disease, fibroproliferative disorder, connective tissue disorder, inflammation, inflammatory disease, respiratory distress syndrome, infertility or diabetes.

22. A method for detecting a disease, disorder or condition where NAALADase levels are altered, comprising:
   (i) contacting a sample of bodily tissue or fluid with an effective amount of a compound of claim 1, wherein said compound binds to any NAALADase in said sample; and
   (ii) measuring the amount of any NAALADase bound to said sample, wherein the amount of NAALADase is diagnostic for said disease, disorder or condition.

23. A method for detecting a disease, disorder or condition where NAALADase levels are altered in a mammal, comprising:
   (i) labeling a compound of claim 1 with an effective amount of an imaging reagent;
   (ii) administering to said mammal an effective amount of the labeled compound;
   (iii) allowing said labeled compound to localize and bind to NAALADase present in said mammal; and
   (iv) measuring the amount of NAALADase bound to said labeled compound, wherein the amount of NAALADase is diagnostic for said disease, disorder or condition.

24. A diagnostic kit for detecting a disease, disorder or condition where NAALADase levels are altered, comprising a compound of claim 1 labeled with a marker.

25. A pharmaceutical composition comprising:
   (i) an effective amount of a compound of claim 1; and
   (ii) a pharmaceutically acceptable carrier.

* * * * *